(12) United States Patent
Thompson et al.

(10) Patent No.: US 9,113,535 B2
(45) Date of Patent: Aug. 18, 2015

(54) FUSING PORPHYRINS WITH POLYCYCLIC AROMATIC HYDROCARBONS AND HETEROCYCLES FOR OPTOELECTRONIC APPLICATIONS

(75) Inventors: Mark E. Thompson, Anaheim, CA (US); Viacheslav Diev, Los Angeles, CA (US); Kenneth Hanson, Carrboro, NC (US); Stephen R. Forrest, Ann Arbor, MI (US)

(73) Assignees: The University of Southern California, Los Angeles, CA (US); The Regents of the University of Michigan, Ann Arbor, MI (US)

( * ) Notice: Subject to any disclaimer, the term of this patent is extended or adjusted under 35 U.S.C. 154(b) by 616 days.

(21) Appl. No.: 12/985,439

(22) Filed: Jan. 6, 2011

(65) Prior Publication Data

US 2012/0001155 A1    Jan. 5, 2012

Related U.S. Application Data

(60) Provisional application No. 61/360,026, filed on Jun. 30, 2010.

(51) Int. Cl.
*C07D 487/22* (2006.01)
*H05B 33/10* (2006.01)
*C09B 47/00* (2006.01)
*H01L 51/00* (2006.01)

(52) U.S. Cl.
CPC .............. *H05B 33/10* (2013.01); *C07D 487/22* (2013.01); *C09B 47/00* (2013.01); *H01L 51/0072* (2013.01); *H01L 51/0077* (2013.01); *C09K 2211/1007* (2013.01); *C09K 2211/1011* (2013.01); *C09K 2211/1029* (2013.01); *C09K 2211/188* (2013.01); *H01L 51/0092* (2013.01); *Y02E 10/549* (2013.01)

(58) Field of Classification Search
CPC .................................................... C07D 487/22
USPC ......................................................... 540/145
See application file for complete search history.

(56) References Cited

U.S. PATENT DOCUMENTS

| | | | |
|---|---|---|---|
| 5,703,230 A | 12/1997 | Boyle et al. | |
| 2003/0187252 A1 | 10/2003 | Osuka | |
| 2007/0152189 A1 | 7/2007 | Li et al. | |
| 2008/0311304 A1 | 12/2008 | Thompson et al. | |
| 2009/0256141 A1 | 10/2009 | Thompson et al. | |

FOREIGN PATENT DOCUMENTS

| | | |
|---|---|---|
| EP | 1 318 151 B1 | 3/2007 |
| JP | 2008248134 | 10/2008 |
| WO | 96/16966 A1 | 6/1996 |
| WO | 2008157118 A1 | 12/2008 |
| WO | 2009049273 A2 | 4/2009 |
| WO | 2011/028610 | 8/2010 |

OTHER PUBLICATIONS

Sooambar et al. Synthesis, photophysical, electrochemical, and electrochemiluminescent properties of 5,15-bis(9-anthracenyl)porphyrin derivatives, Organic & Biomolecular Chemistry (2009), 7(11), 2402-2413.*
International Search Report and Written Opinion issued on Feb. 24, 2012 for PCT Application No. PCT/US2011/041992 filed Jun. 27, 2011.
Wasielewski, Michael R., "Photoinduced Electron Transfer in Supramolecular Systems for Artifical Photosynthesis", Chem. Rev. 1992, 92, pp. 435-461.
Harriman, Anthony, et al, "A Strategy for Constructing Photosynthetic Models: Porphyrin-containing Modules Assembled Around Transition Metals", Chemical Society Reviews, 1996, pp. 41-48.
Murakami, Yukito, et al, "Artificial Enzymes", Chem. Rev. 1996, 96, pp. 721-758.
Perez, M. Dolores, et al, "Organic Photovoltaics Using Tetraphenylbenzoporphrin Complexes as Donor Layers", Adv. Mater. 2009, 21, pp. 1517-1520.
Imahori, H., "Large π-Aromatic Molecules as Potential Sensitizers for Highly Efficient Dye-Sensitized Solar Cells", Accounts of Chemical Research, vol. 42, No. 11, Nov. 2009, pp. 1809-1818.
Liu, Yijiang, et al, "Thiophene-linked porphyrin derivatives for dye-sensitized solar cells", Chem. Commun., 2009. pp. 2499-2501.

(Continued)

*Primary Examiner* — Brian McDowell
(74) *Attorney, Agent, or Firm* — Duane Morris LLP

(57) ABSTRACT

A compound that can be used as a donor material in organic photovoltaic devices comprising a non-activated porphyrin fused with one or more non-activated polycyclic aromatic rings or one or more non-activated heterocyclic rings can be obtained by a thermal fusion process. The compounds can include structures of Formula I:

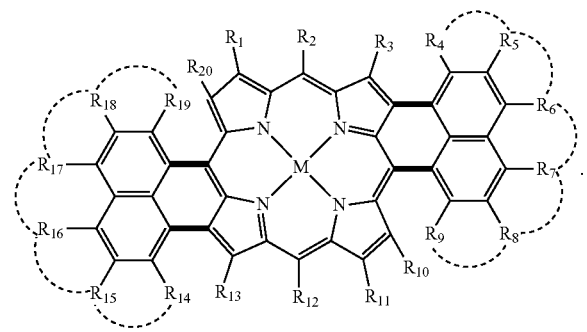

By heating the reaction mixture of non-activated porphyrins with non-activated polycyclic aromatic rings or heterocyclic rings to a fusion temperature and holding for a predetermined time, fusion of one or more polycyclic rings or heterocyclic rings to the non-activated porphyrin core in meso,β fashion is achieved resulting in hybrid structures containing a distorted porphyrin ring with annulated aromatic rings. The porphyrin core can be olygoporphyrins.

9 Claims, 36 Drawing Sheets

(56) References Cited

OTHER PUBLICATIONS

Che, Chi-Ming, et al, "A High-Performance Organic Field-Effect Transistor Based on Platinum(II) Porphyrin: Peripheral Substituents on Porphyrin Ligand Significantly Affect Film Structure and Charge Mobility", Chem. Asian J. 2008, 3, pp. 1092-1103.

Peumans, Peter, et al, "Small molecular weight organic thin-film photodetectors and solar cells", Journal of Applied Physics, vol. 93, No. 7, Apr. 1, 2003, pp. 3693-3723.

Huijser, Annemarie, et al, "The Mechanism of Long-Range Exciton Diffusion in a Nematically Organized Porphyrin Layer", J. AM. Chem. Soc. 2008, 130, pp. 12496-12500.

Winters, Mikael U., et al, "Probing the Efficiency of Electron Transfer through Porphyrin-Based Molecular Wires", J. AM. Chem. Soc. 2007, 129, pp. 4291-4297.

Siebbeles, Laurens D.A., et al, "Effect of molecular organization on exiton diffusion in thin films of bioinspired light-harvesting molecules", J. Mater. Chem., 2009, 19, pp. 6067-6072.

Huijser, Annemarie, et al, "Efficient Exciton Transport in Layers of Self-Assembled Porphyrin Derivatives", J. AM. Chem. Soc. 2008, 130, pp. 2485-2492.

Ikeda, Toshiaki, et al, "Meso-β Doubly Linked Zn(II) Porphyrin Trimers: Distinct anti-versus-syn Effects on Their Photophysical Properties", Organic Letters 2009, vol. 11, No. 14, pp. 3080-3083.

Bonifazi, Davide, et al, Exceptional Redox and Photophysical Properties of a Triply Fused Diporphyrin-C60 Conjugate: Novel Scaffolds for Multicharge Storage in Molecular Scale Electronics, Angew. Chem. Int. Ed. 2003, 42, pp. 4966-4970.

Ahn, Tae Kyu, et al, Comparative Photophysics of [26]- and =[28]Hexaphyrins (1.1.1.1.1.1): Large Two-Photon Absorption Cross Section of Aromatic [26]Hexaphrins (1.1.1.1.1.1), J. AM. Chem. Soc. 2005, 127, pp. 12856-12861.

Rozhkov, Vladimir V., et al, "Luminescent Zn and Pd Tetranaphthaloporphyrins", Inorganic Chemistry, vol. 42, No. 14, 2003, pp. 4253-4255.

Finikova, Olga S., et al, "Synthesis of Symmetrical Tetraaryltetranaphtho[2,3]porphyrins", J. Org. Chem. 2005, 70, pp. 4617-4628.

European Search Report issued Aug. 29, 2014, in counterpart EP Patent Application No. 11810088.2.

Davis, N. et al., "Expanding the Porphyrin π-System by Fusion with Anthracene", Organic Letters, Sep. 2008, 10(18);3945-3947.

Hayashi, S. et al., "Napthyl-Fused π-Elongated Porphyrins for Dye-Sensitized TiO2 Cells", Journal of Physical Chemistry, Oct. 2008, 112(39):15576-15585.

Yamane, O. et al., "Pyrene-Fused Porphyrins: Annulation Reactions of meso-Pyrenylporphyrins", Chemistry Letters, Jan. 2004, 33(1):40-41.

Fox, S. et al., "Synthetic routes to porphyrins bearing fused rings", Tetrahedron, Oct. 2006, 62 (43):10039-10054.

Diev, V. et al., "Fused-Pyrine-Diporphyrins: Shifting Near-Infrared Absorption to 1.5 μm and Beyond", Angew. Chem. Int. Ed., Wiley-VCH Verlag GMBH&Co., KGAA,DE, Jul. 2010, 49(32):5523-5526.

Spence, J.D. et al., "Synthesis and Bergman cyclization of a β-extended porphyrenediyne", Chem. Commun. 2004, pp. 180-181.

Official Action issued Jul. 25, 2014 in counterpart CN patent application No. 201180032125.7.

Davis, Nicola K.S. et al., "Bis-Anthracene Fused Porphyrins: Synthesis, Crystal Structure, and Near-IR Absorption", Organic Letters, 2010, 12(9):2124-2127.

Sooambar, C. et al., "Synthesis, photophysical, electrochemnical, and electrochemiluminescent properties of 5,15-bis(9-anthracenyl)porphyrin derivatives", Organic & Biomolecular Chemistry, 2009, 7:2402-2413.

Official Action issued Dec. 22, 2014 in counterpart Taiwan patent application No. 100122013.

Aihara, H. et al., "Multicarbocycle Formation Mediated by Arenoporphyrin 1,4-Diradicals: Synthesis of Picenoporphyrins", Angew. Chem. Int. Ed. 2001, 40(18):3439-3441.

Tanaka, Masanobu, et al. "Novel unsymmetically Π-elongated porphyrin for dye-sensitized TiO2 cells," Chem Commun., 2007, pp. 2069-2071.

* cited by examiner

Absorption spectra of ZnQFTPP in pyridine solution and in the thin film

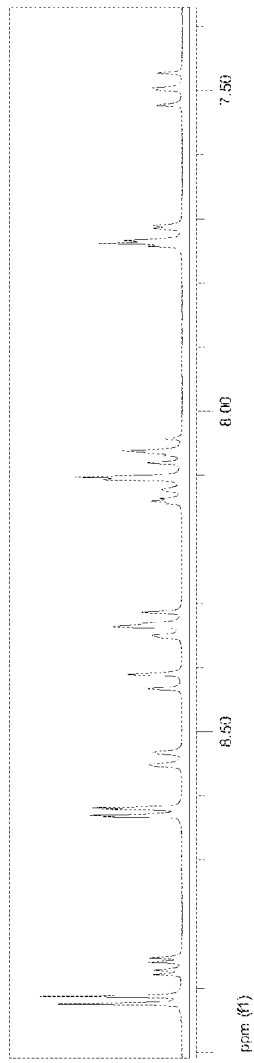
FIG. 26(a) 1H NMR spectrum of ZnBPP
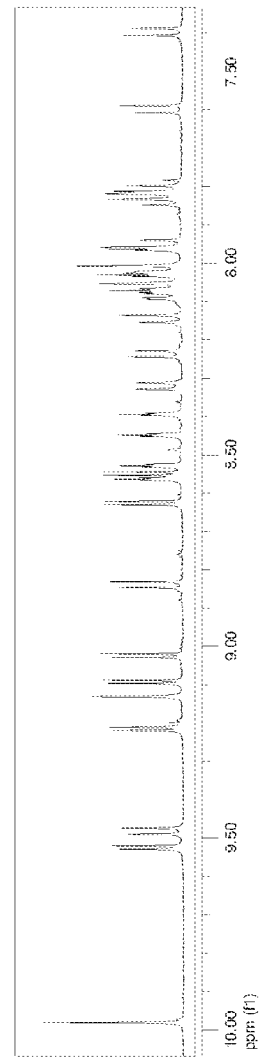
FIG. 26(b) 1H NMR spectrum of ZnMFBPP
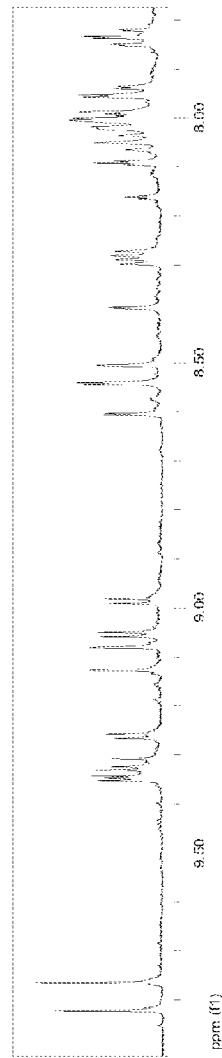
FIG 26(c) 1H NMR spectrum of ZnDFBPP

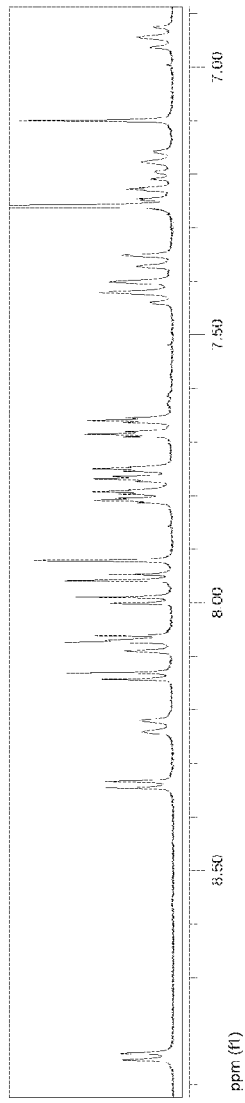
FIG. 26(d) ¹H NMR spectrum of ZnFBTP
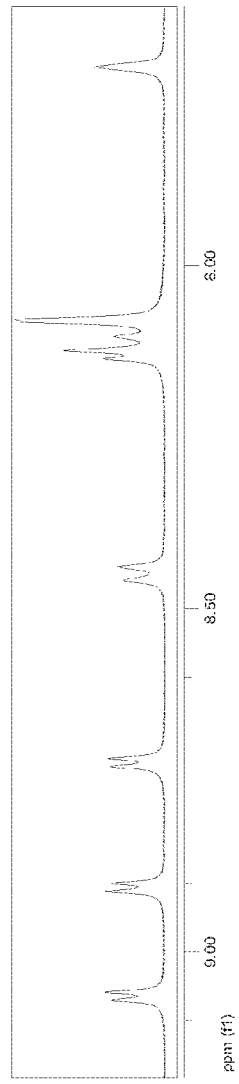
FIG. 26(e) ¹H NMR spectrum of cyano-phenyl porphyrin dimer
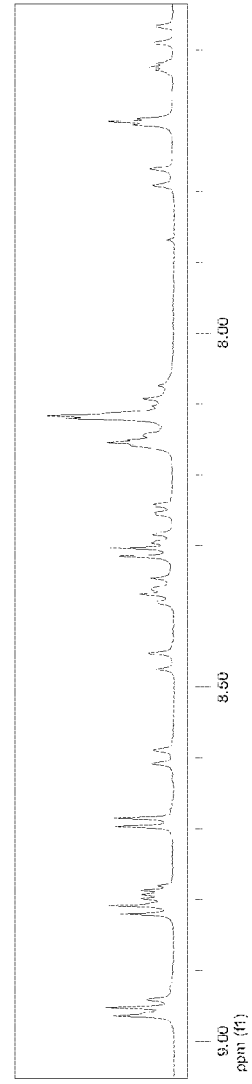
FIG. 26(f) ¹H NMR spectrum of pyrene porphyrin trimer.

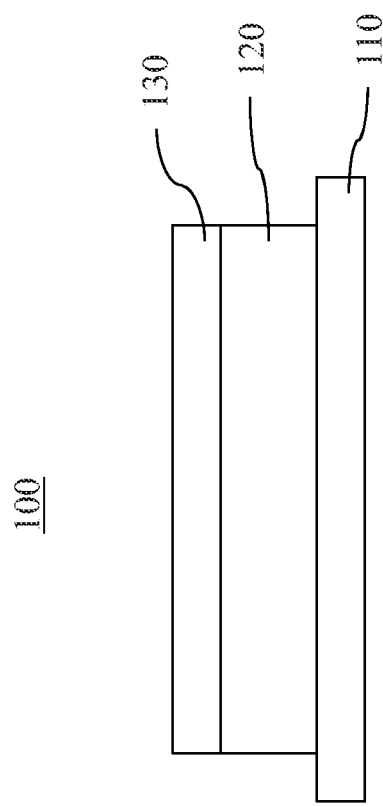

FUSING PORPHYRINS WITH POLYCYCLIC AROMATIC HYDROCARBONS AND HETEROCYCLES FOR OPTOELECTRONIC APPLICATIONS

CROSS-REFERENCE TO RELATED APPLICATIONS

This application claims the benefit under 35 U.S.C. §119 (e) of U.S. Provisional Application Ser. No. 61/360,026, filed on Jun. 30, 2010, the disclosure of which is incorporated herein by reference in its entirety.

GOVERNMENT RIGHTS

This invention was made with United States Government support under grant number W15P7T-08-C-P409 awarded by the United States Department of Defense; grant number FA9550-10-1-0399 awarded by the Air Force Office of Scientific Research; and grant number DE-SC000957 awarded by the United Stated Department of Energy. The government has certain rights in the invention.

PARTIES TO A JOINT RESEARCH AGREEMENT

The claimed invention was made by, on behalf of, and/or in connection with one or more of the following parties to a joint university corporation research agreement: Regents of the University of Michigan, Princeton University, University of Southern California, Global Photonic Energy Corporation, and Universal Display Corporation. The agreement(s) was in effect on and before the date the claimed invention was made, and the claimed invention was made as a result of activities undertaken within the scope of the agreement(s).

TECHNICAL FIELD

The present disclosure relates to organic films for use in organic electronic devices.

BACKGROUND

Porphyrins are one of the most important biological molecules essential for life and responsible in nature for such oxidation-reduction reactions as photosynthesis in plants and respiration in animals. Synthetic porphyrins have broad applications as useful opto-electronic materials in different fields of organoelectronics, such as solar cells, photodetectors, and as catalysts in a variety of reactions. Advantages of using porphyrins as opto-electronic materials include efficiency of charge separation and charge transport even in thick films of assembled porphyrins, strong absorbance in the visible region, high chemical stability, and ability to tune opto-electronic properties. However, there are some problems associated with application of porphyrins in organoelectronics. Porphyrins have a modest spectral overlap with solar spectrum and the material preparation and isolation is difficult. Additionally, fluorescence of porphyrinoids in the near infrared (NIR) is quite rare. For a number of potential opto-electronic applications strong absorption in NIR spectral region is desired. One of the approaches to get absorption in NIR spectral region is by extending the size of π-conjugation in the porphyrin system. The conjugation of porphyrins can be extended through several modes of substitution involving the (meso), (β,β, (β,meso) and (β,meso, β) positions. It has been shown previously that some aromatic rings can be fused with porphyrins in (β,meso) and (β,meso,β) modes. These reactions require activation of porphyrin rings by metalation with nickel(II) or activation of aromatic rings by multiple alkoxy-substitution. Nickel(II) porphyrins have rapid decay of the excited state due to nickel centered (d,d) quenching and at the same time demetalation of such porphyrins does not have synthetic potential since it requires harsh conditions not suitable with the presence of alkoxy groups (for example, concentrated sulfuric acid). Nickel(II) porphyrinoids have not found any applications in photovoltaics and no emission has been reported for such porphyrins containing nickel atom or donor alkoxy groups. Additionally, this usually causes difficulties with synthesis, and isolation is possible only in small amounts. One of the most limiting factors in use in organoelectronics of many derivatives of porphyrins with extended conjugation is both their very low solubility and inability to sublime.

Almost all porphyrins, phthalocyanines and subphthalocyanines have a metal or heteroatom in the center. The ability of metals to coordinate with different ligands may provide a new way to tune properties of macrocycles and, thus, enhance organoelectronic device performance. Literature data shows that at least for some systems consisting of macrocycles such supramolecular organization through coordination by metal centers can enhance conductivity and charge transport. Although coordination chemistry of metalated macrocycles are very well established, application of this strategy to change and improve optoelectronic devices with use of such macrocycles as porphyrins, phthalocyanines, etc. still remains unrealized.

SUMMARY

According to an aspect of the present disclosure, a compound comprising a non-activated porphyrin fused with one or more non-activated polycyclic aromatic rings or one or more non-activated hetrocyclic rings is disclosed. In one embodiment, the compound comprises a non-activated porphyrin fused with one or more non-activated polycyclic aromatic rings and has a formula selected from the group consisting of:

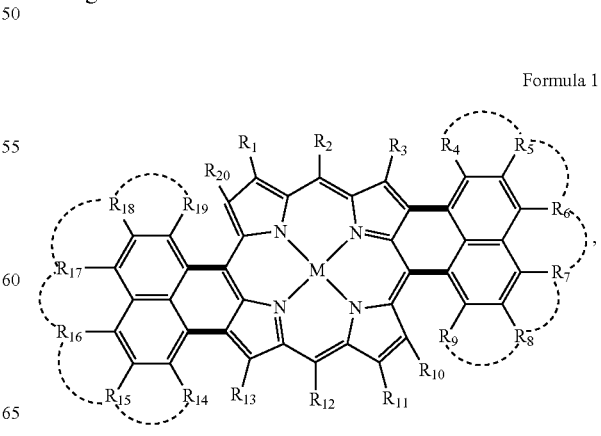

Formula 1

-continued
Formula II
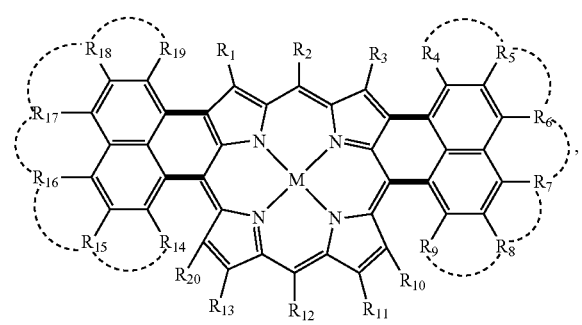
Formula III
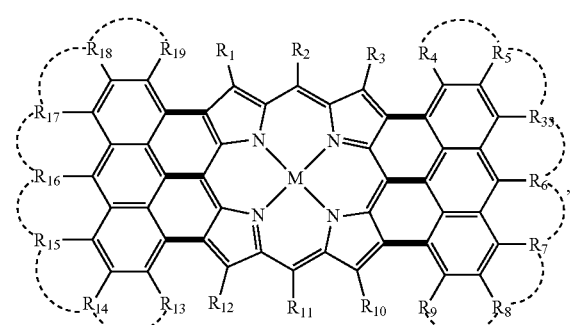
Formula IV
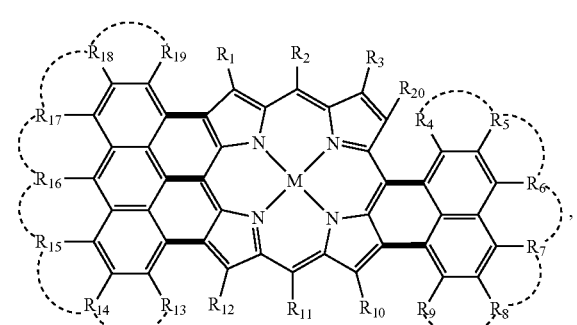
Formula V
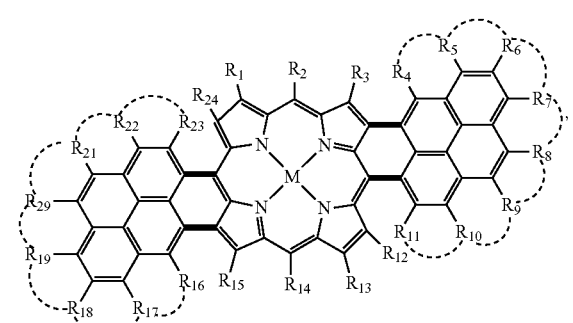
Formula VI
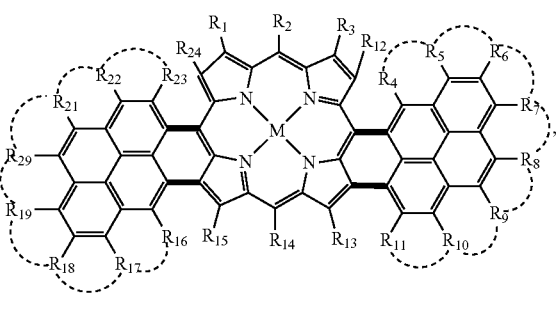
Formula VII
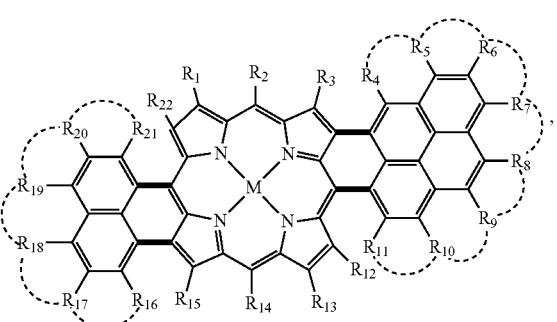
Formula VIII
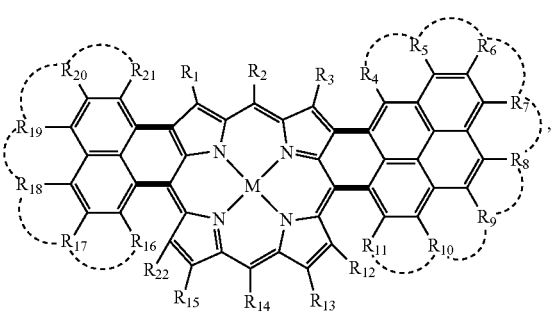
Formula IX
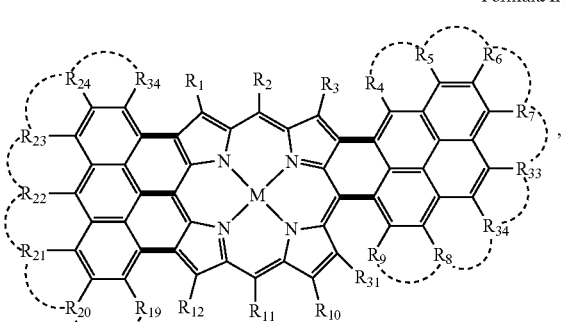

Formula X
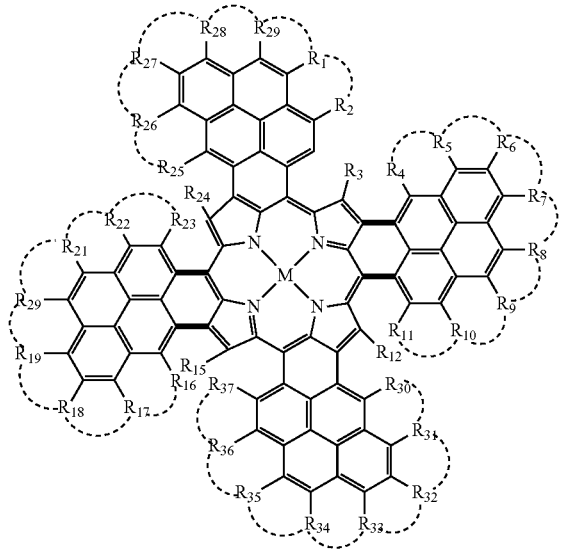
Formula XI
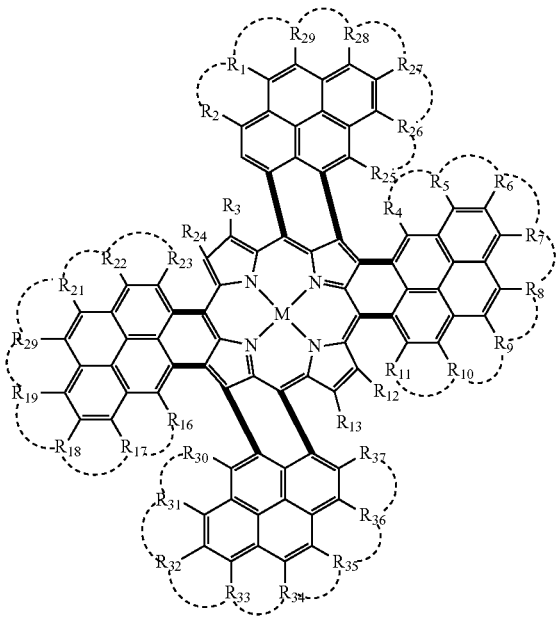
Formula XII
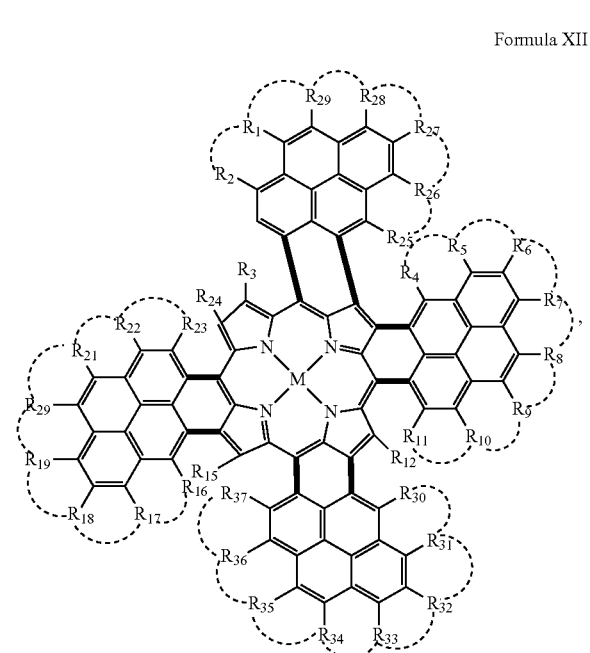
Formula XIII
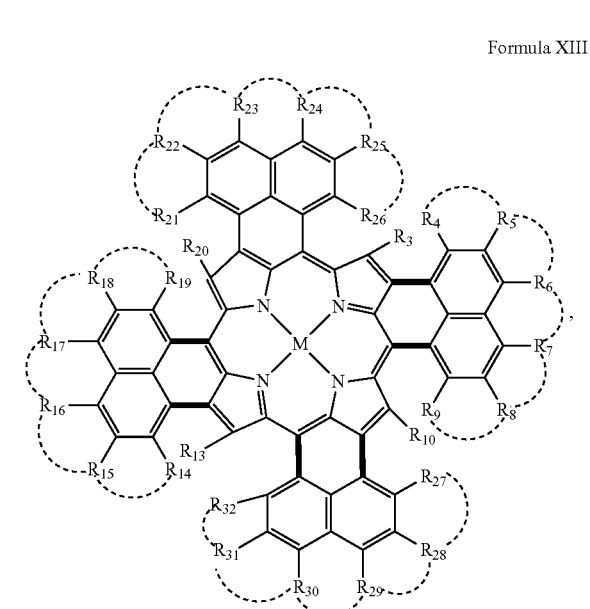

-continued

Formula XIV

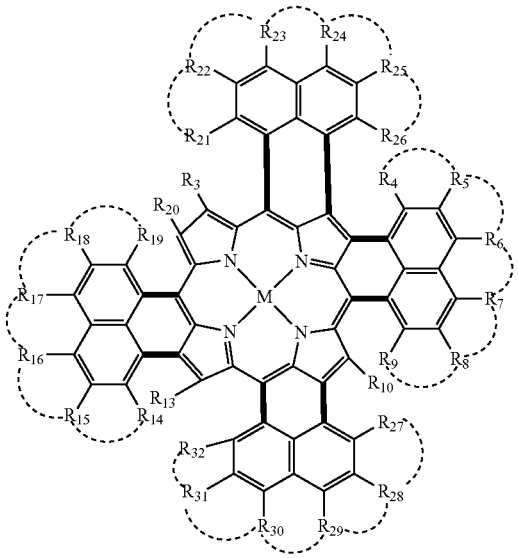

Formula XV

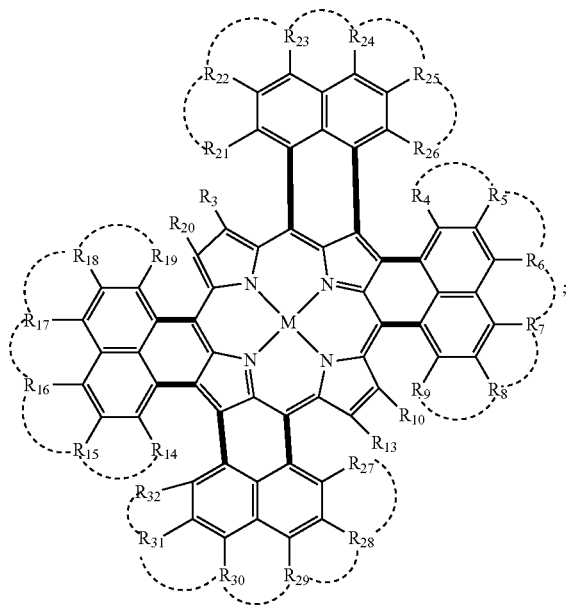

wherein M is two hydrogen atoms or any element selected from the group consisting of Mg, Ca, Sr, Ba, Sc, Y, La, Ce, Ti, Nb, Ta, Cr, Mo, W, Mn, Tc, Re, Fe, Ru, Os, Co, Rh, Tr, Ni, Pd, Pt, Cu, Ag, Au, Zn, Cd, Hg, Al, Ga, In, Tl, Si, Ge, Sn, Pb, P, As, Sb, Bi, Pr, Nd, Sm, Eu, Gd, Tb, Dy, Ho, Er, Tm, Yb, Lu, Th, and U; wherein $R_1$-$R_{37}$ are independently selected from the group consisting of electron donors and acceptors, such as hydrogen, alkyl, fluoroalkyl, hydroxyl, alkoxy, halo (Cl, Br, I), chalcogens (S, Se, Te), mercapto group, amino, cyano, alkenyl, alkynyl, and aryl; and each dotted arc is all possible combinations of fused rings, both aromatic and unsaturated or combination of both aromatic and unsaturated rings including four, five, six, seven, eight, or nine-membered rings, and all possible combination of fused heterocyclic rings with one or more heteroatoms, including all possible combinations of all heteroatoms in all possible arrangement.

In another embodiment, the compound comprises a non-activated porphyrin fused with one or more non-activated heterocyclic rings and the compound, has a formula selected from the group consisting of:

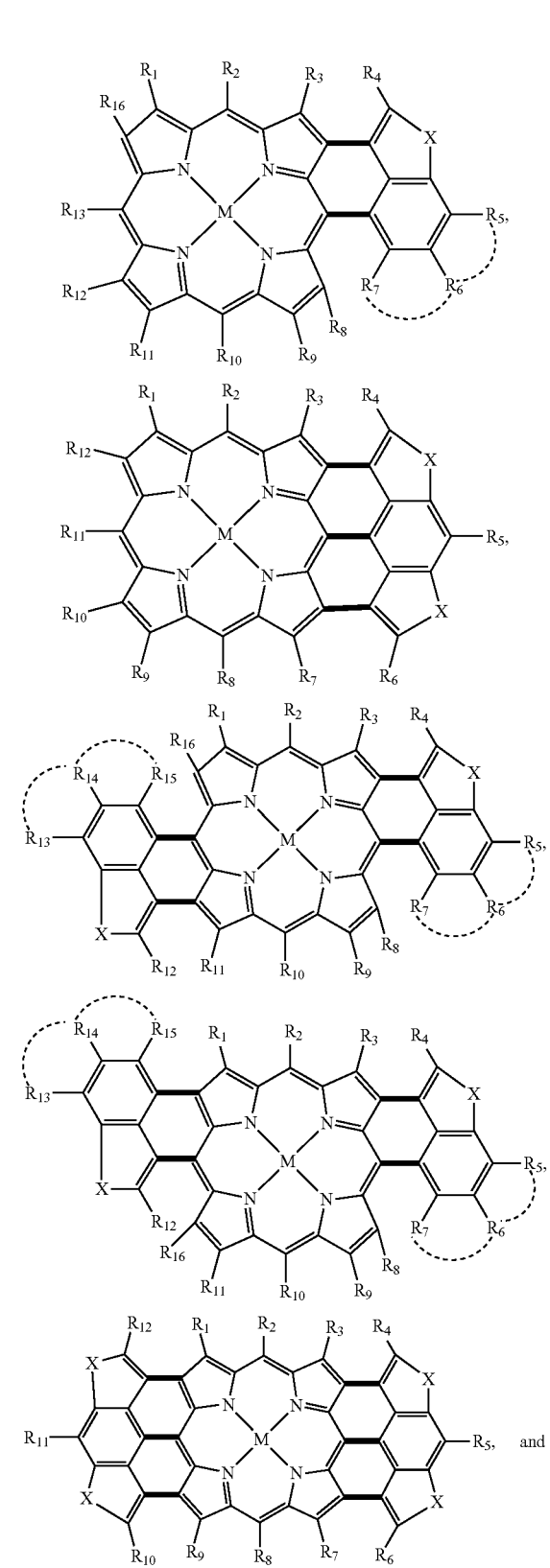

-continued

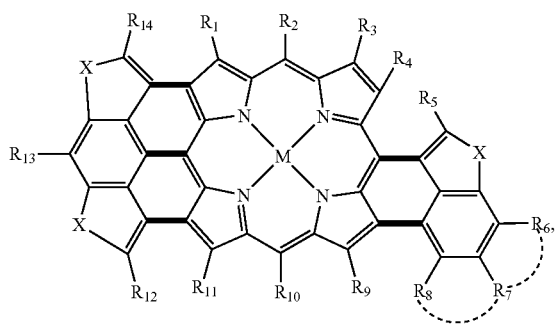

wherein M is two hydrogen atoms or any element selected from the group consisting of Mg, Ca, Sr, Ba, Sc, Y, La, Ce, Ti, Nb, Ta, Cr, Mo, W, Mn, Tc, Re, Fe, Ru, Os, Co, Rh, Ir, Ni, Pd, Pt, Cu, Ag, Au, Zn, Cd, Hg, Al, Ga, In, Tl, Si, Ge, Sn, Pb, P, As, Sb, Bi, Pr, Nd, Sm, Eu, Gd, Tb, Dy, Ho, Er, Tm, Yb, Lu, Th, and U; wherein $R_1$-$R_{14}$ are independently selected from the group consisting of electron donors and acceptors, such as hydrogen, alkyl, fluoroalkyl, hydroxyl, alkoxy, halo (Cl, Br, I), chalcogens (S, Se, Te), mercapto group, amino, cyano, alkenyl, alkynyl, and aryl, X is a heteroatom selected from the following list: O, S, Se, Te, N, P, As, Si, Ge, B; and each dotted arc is all possible combinations of fused rings, both aromatic and unsaturated or combinations of both aromatic and unsaturated rings including four, five, six, seven, eight, or nine-membered rings, and all possible combinations of fused heterocyclic rings with one or more heteroatoms, including all possible combinations of all heteroatoms in all possible arrangements.

According to an implementation of the present disclosure, a process for fusing one or more non-activated, polycyclic rings to a non-activated porphyrin core comprises heating a quantity of precursor porphyrins to a fusion temperature in an inert gas environment; holding the precursor porphyrins at the fusion temperature for a predefined period of time until the precursor porphyrins melt and form a mixture of fused porphyrins; cooling the mixture of fused porphyrins to room temperature; and separating the mixture of fused, porphyrins into various fused porphyrin compounds. Presumably, the fusion takes places when the prophyrins are in the melted phase. Thus, generally, the fusion temperature is above the melting point of the precursor porphyrins.

The fusion of the non-activated porphyrins and one or more non-activated polycyclic aromatic rings or non-activated heterocyclic rings is achieved by thermal fusion. These fused, porphyrins are not available by using other methods reported for similar fusion reactions in literature ($FeCl_3$, FeCl/AgOTf, Sc(OTf)$_3$/DDQ, DDQ, PhI(OTf)$_2$/BF$_3$OEt$_2$, (p-BrPh)$_3$NSbCl$_6$, K/Na, F$_4$TCNQ). Thermal fusion of one or more polycyclic rings to a porphyrin core in meso,β fashion is carried, out to obtain hybrid, structures containing distorted porphyrin ring with annulated aromatic rings. This ring fusion causes a significant distortion of the porphyrin away from planarity. The non-planar structure leads to broadening and red shifting of absorption bands and an enhanced solubility in organic solvents. Such meso,β fused porphyrins represent a new family of dyes with strong absorption across the solar spectrum and emission in NIR region. Suitable substituted meso,β substituted porphryins also have significant absorption in both the visible and NIR part of the spectrum. These materials make excellent candidates for active materials in solar cells and photodetectors, where strong absorption in the visible and NIR are crucial. They also have significant benefits for application in NIR light emitting diodes. Fusion of polycyclic rings with a diprophyrin or porphyrin tape has been previously disclosed in the art, but fusion of polycyclic rings with single porphyrin cores or fusion by thermal treatment without activating agents have not been achieved previously. The preparation and use effusing polycyclic aromatic hydrocarbons and heterocycles to porphyrins extend and broaden absorption, and help to modify the solubility, crystallinity, and film forming properties of pophyrins.

The method of the present disclosure enables fusion of porphyrin rings to one or more polycyclic aromatic rings or heterocyclic rings without activation of the porphyrin rings or activation of the aromatic rings or heterocyclic rings.

According to another aspect of the present disclosure an organic photosensitive device incorporating the fused porphyrin material disclosed herein and a method for fabricating such organic photosensitive device are also disclosed. Such organic photosensitive devices include photovoltaic devices which convert light into photocurrent and thereby supply electrical power to a circuit and other embodiments such as photodetectors, for example.

BRIEF DESCRIPTION OF THE DRAWINGS

FIG. 26(a)-(f) shows $^1$H NMR spectra of ZnBPP, ZnMFBPP, ZnDFBPP, ZnFBTP, cyano-phenyl porphyrin dimer and pyrene porphyrin trimer, respectively.

FIG. 27 is a schematic illustration of the architecture of an example of a photosensitive device incorporating the compounds disclosed herein.

Except where noted, all drawings are schematic and are not drawn to scale and are not intended to necessarily convey actual dimensions.

DETAILED DESCRIPTION

I

According to an aspect of the present disclosure, mono-, doubly-, triply-, and tetra-fused porphyrins with aromatic rings in meso,β mode and a method of their preparation by thermal ring closure of the singly substituted porphyrins with appropriate polycyclic aromatic rings (e.g. naphthalene, pyrene, phenanthrene, etc) is described. The use of these thermally fused porphyrins in donor/acceptor configuration devices typical with common organic solar cells (i.e. copper phthalocyanine/C$_{60}$) is also described.

Thermal fusion of one or more polycyclic rings to a porphyrin core in meso,β fashion to obtain hybrid, structures containing a distorted porphyrin ring with annulated aromatic rings is schematically shown below for pyrene fused porphyrins.

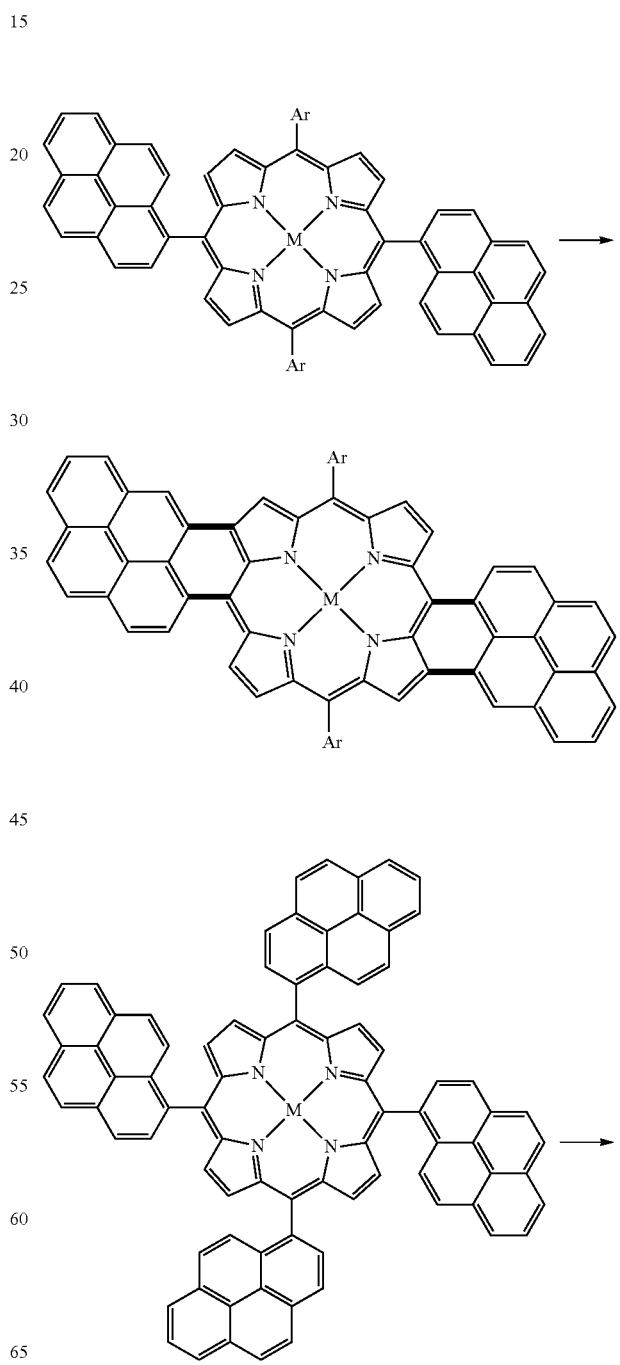

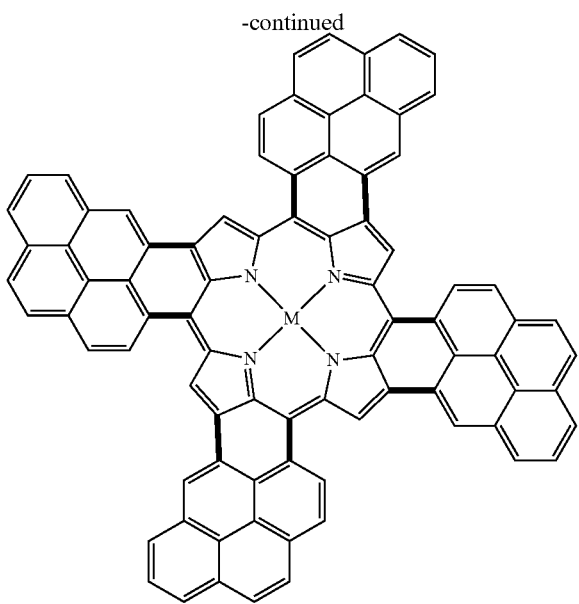

One of the ways to overcome problems with solubility in extended aromatic systems is to introduce out-of-plane distortion. Fusion in (meso,β mode with polycyclic aromatic rings (PAHs—rings, consist of several condensed benzene rings, such as naphthalene or pyrene rings) should cause such distortion due to unfavorable interactions between β pyrrolic protons of porphyrin ring and protons at the α-position of aromatic rings. In contrast, fusion in (β,meso, β) mode with anthracene rings leads to the formation of planar fused porphyrins with extremely low solubility even by placing multiple solubilizing alkoxy groups. In other (β,meso) fused systems, the distance between two mentioned hydrogen atoms may not lead to large distortion and, therefore, such systems as azulene-fused porphyrins display modest solubility. For the fusion of pyrene rings, all previous attempts to fuse unsubstituted pyrene ring were unsuccessful and is possible only as fusion of one alkoxy-activated pyrene ring. The obtained, pyrene-fused products were not reported to have emission.

Figure 1:
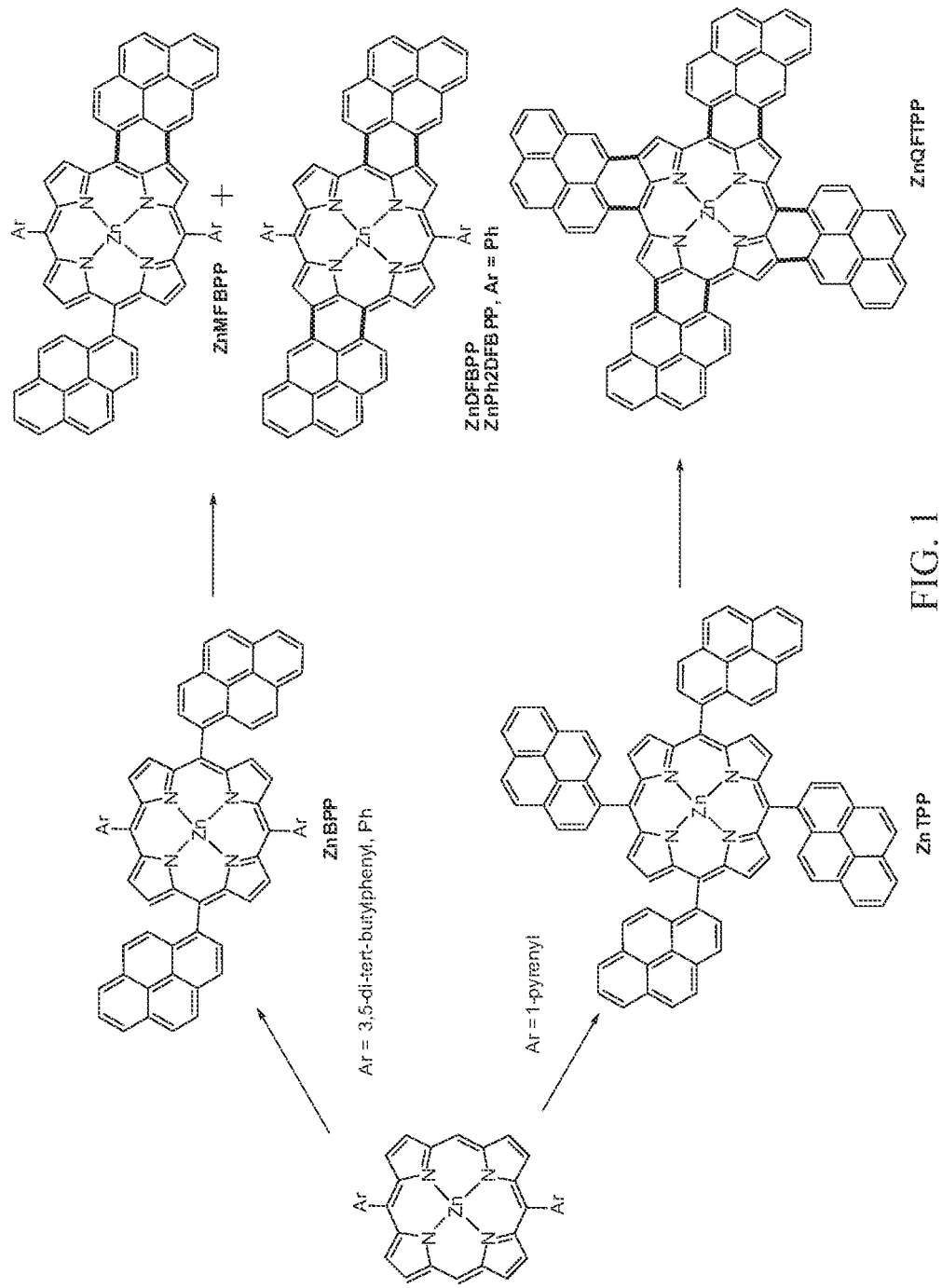
FIG. 1 illustrates the synthesis of mono (ZnMFBPP), doubly (ZnDFBPP) and quardruply (ZnQFTPP) fused pyrene-porphyrins.

The present disclosure describes a new method of preparation of multiply fused aromatic rings with a porphyrin core which does not require any activation and is possible without any solvents and reagents by previously unknown flash pyrolysis of porphyrins singly connected with the corresponding aromatic ring at high temperatures. At elevated temperatures (500-530° C. under nitrogen), d/s-pyrenyl substituted porphyrin ZnBPP undergoes a thermal ring closure yielding the desired, mono-ZnMFBPP and regioisomeric doubly-fused porphyrins ZnDFBPP (FIG. 1). The product ratio (ZnMFBPP:ZnDFBPP) and reaction yield can be controlled by varying the reaction time. The inventors have found that thermal annealing thin films or small amounts (50-100 mg) of bis-pyrenyl-porphyrin ZnBPP yields ZnDFBPP nearly quantitatively. This reaction has also proven to be scalable, in excess of several grams, although with smaller isolated yields of ZnDFBPP of about 25-35%.

The major byproduct in large scale reactions, comprising 35-40% of the porphyrinic product, involves the loss of one di-tert-butylphenyl group from ZnDFBPP. While this byproduct affects yields of ZnDFBPP, the loss of a di-tert-butylphenyl groups does not affect, the optical properties of the compound, such that the yield of NIR absorbing and emitting material remains high. All meso-porphyrinic positions appear to be exhaustively fusible, such that fusion is achievable even for tetrakis-pyrenyl-porphyrin ZnTPP to form the quadruply fused product ZnQFTPP therefore, the number of fusion sites of the substituents at meso-porphyrinic positions does not have a limit.

Pyrene ring fusion is verified by the mass spectra of the obtained products, that clearly indicate the loss of two (for ZnMFBPP; $[M]^+=1146.4581$), four (for ZnDFBPP; $[M]^+=1144.4418$) and eight protons (for ZnQFTPP; $[M]^+=1164.32$) relative to the parent compounds ZnBPP ($[MH]^+=1149.4834$) and ZnTPP $[MH]^+1173.2915$). Both regioisomers of doubly fused porphyrin anti-ZnDFBPP and syn-ZnDFBPP (1:1 ratio) were observed, and can be separated using column chromatography (anti-ZnDFBPP is shown in FIG. 1). Structure assignment for both regioisomers can be done by NMR spectroscopy based on the number of equivalent di-tert-butyl-phenyl groups, since regioisomers anti-ZnDFBPP has only one set and syn-ZnDFBPP has two independent sets of signals of protons for the di-tert-butylphenyl groups. Unlike regioisomeric fused porphyrin tapes with strong shape dependence of their photophysical properties, anti-ZnDFBPP and syn-ZnDFBPP have quite similar properties.

Figure 28:
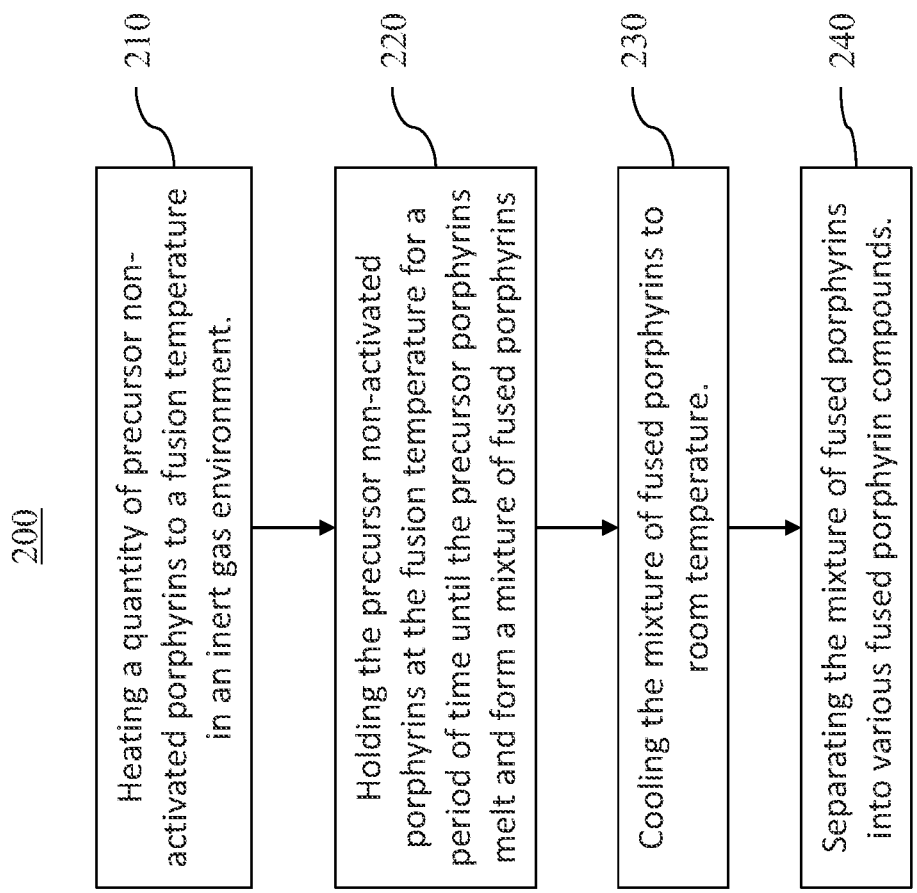
FIG. 28 is a flowchart showing the method of fusing non-activated, porphyrins with one or more non-activated aromatic rings according to the present disclosure.

Referring to the flowchart 200 in FIG. 28, the process for fusing one or more non-activated polycyclic rings to a non-activated porphyrin core according to an implementation of the present disclosure comprises heating a quantity of precursor porphyrins to a fusion temperature in an inert gas environment (block 210) and holding the precursor porphyrins at the fusion temperature for a predefined period of time until the precursor porphyrins melt and form a mixture of fused porphyrins (block 220). The mixture of fused, porphyrins is then cooled to room temperature (block 230) and separated into various fused porphyrin compounds (block 240). The fused porphyrin can be separated using column chromatography then further purified by recrystallization.

An example of the thermal fusion process for thermally fusing non-activated porphyrins with one or more non-activated polycyclic aromatic rings will now be described using the fusion process conducted by the inventors using bis-pyrenyl-porphyrin ZnBPP as the precursor non-activated porphyrin material. A quantity of bis-pyrenyl-porphyrin ZnBPP*MeOH (1 g, 0.845 mmol) was placed into a glass tube (directly or in an appropriate container such as a glass boat). The glass tube was placed into a furnace preheated to a fusion temperature in an inert gas environment (nitrogen, neon, or argon, for example) and held at the fusion temperature for a predefined time period until the precursor material melt and form a mixture of fused porphyrins.

The fusion takes places when the prophyrins are in the melted phase. However, potentially, an appropriate porphyrin may be fused without melting. Thus, generally, the fusion temperature will depend on the melting (or transition) point of the starting porphyrin material to be fused. For porphyrins with lower melting point, the fusion temperature can be lower than 500° C. For porphyrins with higher melting point, the fusion temperature could be higher than 530° C. Preferably, the fusion temperature is above the melting (or transition) point of the precursor porphyrins.

For the quantity of bis-pyrenyl-porphyrin ZnBPP*MeOH (1 g, 0.845 mmol), the fusion temperature was between 500° C.-530° C. The furnace was preheated, to a fusion temperature of 530° C. and held at that temperature for about 5 minutes. First, the furnace temperature rose to 530° C. in 1-2 minutes and after additional approx. 1-2 minutes, the precursor non-activated, porphyrin material melted. The precursor material turned into a brown color and bubbles appeared.

After about 0.5 minutes, the glass tube was removed, from the furnace and the mixture of fused porphyrins was cooled to room temperature while under the inert gas environment. Prolonged heating causes reduced yields of the doubly fused product ZnDFBPP.

In general, the optimal dwell time at the fusion temperature is the duration which results in the maximum amount of the desired fused product in the reaction mixture. This dwell time can be found experimentally. The fusion dwell time will depend on the nature of the polycyclic aromatic rings and stability of the products at high temperature. If the fusion dwell time is short, a significant amount of the starting porphyrin material may be present in the reaction mixture. If the fusion dwell time is too long, already formed fused porphyrins can decompose (for example, with the loss of one or two aryl substituents such as di-tert-butyl-phenyl group).

The amount of desired fused products will increase until all starting material is converted into fused products. After that, if competing reactions exist, such as decomposition, the amount of fused product will decrease. Therefore, one can determine the fusion dwell time that, would produce the maximum amount of the fused, product experimentally.

The inventors repeated the process five additional times with new 1 g batches of the precursor non-activated porphyrin material resulting in a total of about 6 g of the mixture of fused porphyrin ZnBPP. The scalable process however can be done in larger amounts of starting porphyrin, this would, lead to the final fused products, however, with smaller yields.

The crude mixture of fused porphyrins was dissolved in dichloromethane (100 ml) with addition of hexanes (300 ml) and pyridine (5 ml) and separated into various fused porphyrin compounds by graduated elution on an alumina column chromatograph (400 g). An elution of the mixture of fused porphyrins with dichloromethane gave first fraction which contained compound ZnMFBPP. Next, an elution with hexanes:dichloromethane:pyridine=700:300:5 mixture gave crude doubly fused, porphyrin ZnDFBPP which was purified by recrystallization from dichloromethane by layered, addition of methanol to give ZnDFBPP (about 93-95% purity 1.80 g, 30%). An elution with dichloromethane:pyridine=1000:5 mixture gave doubly fused porphyrin with the loss of one di-tert-butyl-phenyl group which was purified by recrystallization from dichloromethane-pyridine by layered addition of methanol (2.3 g, 38%). Higher purity doubly fused porphyrin ZnDFBPP can be obtained by column chromatography on silica gel (gradient elution with hexanes:dichloromethane mixtures 1000:50 to 800:200). The first fraction containing compound ZnMFBPP was additionally purified by silica gel column (gradient elution with hexanes:ethyl acetate mixtures 1000:5 to 1000:15) and crystallized from dichloromethane by layered addition of methanol to give compound ZnMFBPP (0.54 g, 9%).

According to another aspect of the present disclosure, the process for fusing non-activated porphyrins can be incorporated into a process for fabricating a photosensitive device such that the non-activated porphyrins in the donor material can be fused in the device form factor. When carried out in the device form factor, the thermal fusion is conducted with the precursor porphyrins in thin films by spin-coating the precursor porphyrins from appropriate solution on glass, indium tin oxide or other surfaces.

One such method for fabricating a photosensitive device forms a planar donor-acceptor heterojunction device. The method, comprises depositing a first electrode layer on a suitable substrate and depositing a layer of organic donor material over the first electrode, thus forming an interim structure, wherein the organic donor material comprises a precursor porphyrin material. The interim structure is then heated to a fusion temperature for the particular precursor porphyrin material. The heating is conducted in an inert gas environment (e.g. nitrogen or other inert gas) and held at the fusion temperature for a predefined period of time until the precursor porphyrin material melts and forms a layer of mixture effused porphyrins. A layer of an organic acceptor material is then deposited, over the layer of the organic donor material, wherein the organic acceptor material layer is in direct contact with the organic donor material layer, whereby the organic donor material layer and the organic acceptor material layer form a photoactive region. A second electrode layer is then deposited over the organic acceptor material layer. The first electrode and the second electrodes can be anode and cathode, respectively and the suitable electrode materials are well known to the art. For example, the anode can be formed using a transparent electrode material such as ITO (indium tin oxide) and the cathode can be formed using a metal such as silver. The device may further comprise a layer of bathocuproine (BCP) disposed between the acceptor material layer and the second electrode, the BCP functioning as an exciton blocking layer in the device.

According to another aspect, a method for fabricating a photosensitive device having a bulk donor-acceptor heterojunction is disclosed. The method comprises depositing a first electrode layer on a suitable substrate and depositing a layer of a mixture of an organic donor material and an organic acceptor material over the first electrode, thus forming an interim structure, wherein the organic donor material comprises a precursor porphyrin material. The interim structure is then heated to a fusion temperature for the particular precursor porphyrin material for fusing the porphyrins. The heating is conducted in an inert gas environment and held at the fission temperature for a predefined period of time until the precursor porphyrin material in the mixture of the organic donor and acceptor materials melts and forms fused porphyrins. The fused porphyrins and the organic acceptor material form a photoactive region having a bulk heterojunction. Subsequently, other layers of the photosensitive device, such as a second electrode layer, is deposited over the photoactive region. The device may further comprise a layer of BCP disposed between the photoactive region and the second electrode, the BCP functioning as an exciton blocking layer in the device.

According to another aspect, a quantity of fused porphyrin compounds can be used to form a donor layer of a photoactive region in a photosensitive device. The examples of PV devices whose JV characteristics are plotted in FIGS. 8-12, discussed below, were fabricated in such manner.

As described above, the donor materials of the present disclosure can be used to form a bulk heterojunction configuration of a photosensitive device. Using solution processing, more than one component can be mixed or blended for deposition including donor and acceptor materials together. The donor materials can be mixed with a soluble acceptor, such as PCBM or PTCDI, to spin-coat or spin-cast the photoactive region having a bulk heterojunction configuration. The fused non-activated porphyrin donor materials disclosed herein can be co-deposited, with other materials, such as another donor material or an acceptor material.

There are several major differences between the porphyrins fused in (meso,β) mode with aromatic rings as disclosed in the present disclosure compared to previously reported fused, porphyrins in (meso,β) and (β,meso,β) modes, (1) First, the fusion of one or two pyrene rings in (meso,β) mode with a porphyrin molecule leads to a product with substantially higher solubility. In contrast, even the presence of several alkoxy groups in porphyrins fused with anthracene rings in (β,meso,β) mode gives compounds with very limited solubility. Thus, distortion in (meso,β) mode is an important structural factor for the control of different properties of porphyrinoids. (2) Next, using the thermal fusion method disclosed herein, a direct fusion is possible without any activation of porphyrins (e.g. porphyrin rings with nickel(II) metalation and PAHs with alkoxy groups) for unsubstituted PAHs rings with different metalated porphyrins (Zn, Pt, Pd, Cu, Pb, etc). Moreover, fusion of unactivated aromatic rings with unactivated porphyrin rings cannot be achieved by known methods for similar fusions.

The thermal fusion process does not require any solvents and reagents. Thus, because of its efficiency, the thermal fusion can be described, as "click" chemistry reaction, which can be used for generating different fused products in situ by annealing thin films of starting non-fused porphyrins directly on electrodes (e.g., ITO) during manufacture of optoelectronic devices. (3) The fused non-activated porphyrins of the present disclosure exhibit emission in NIR spectral region with one of the highest, efficiencies reported in literature with quantum yields of emission gradually increasing with the number of fused sites in going into NIR from 3.3% for the starting non-fused porphyrin ZnBPP at 590 and 640 nm to 8% for the mono-fused porphyrin ZnMFBPP at 716 nm and 10% for the doubly fused porphyrin ZnDFBPP at 816 nm. This trend is quite different from the effect of extending conjugation in other porphyrins. Thus, porphyrinoids in general are very poor emitters in NIR spectral region and NIR emission beyond 720 nm from other fused systems involving meso position have not been reported.

Figure 2:
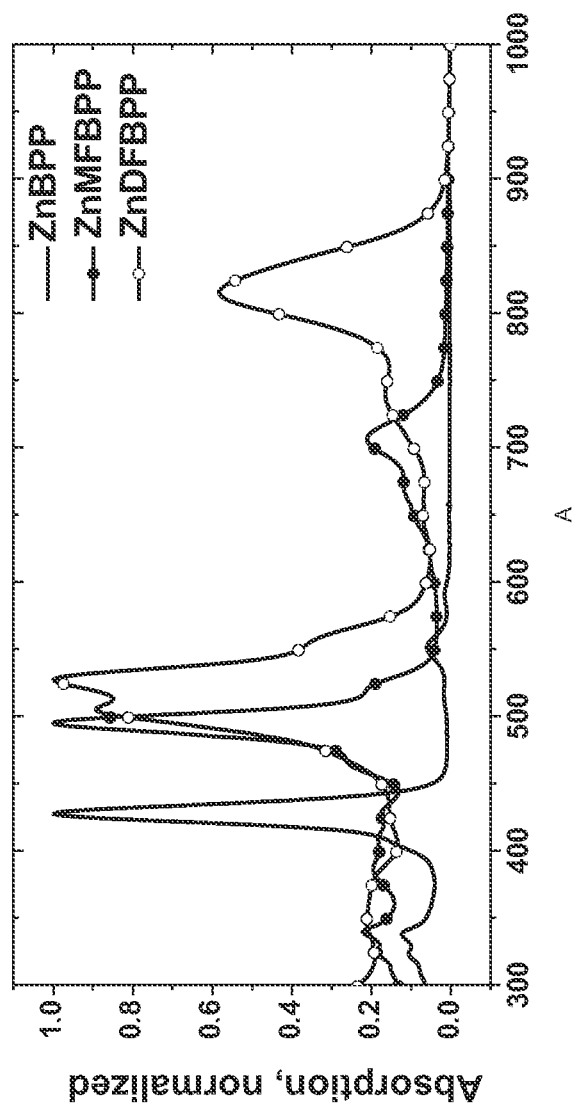
FIG. 2 shows the absorption spectra of ZnBPP, ZnMFBPP, ZnDFBPP in dichloromethane solution.
Figure 3:
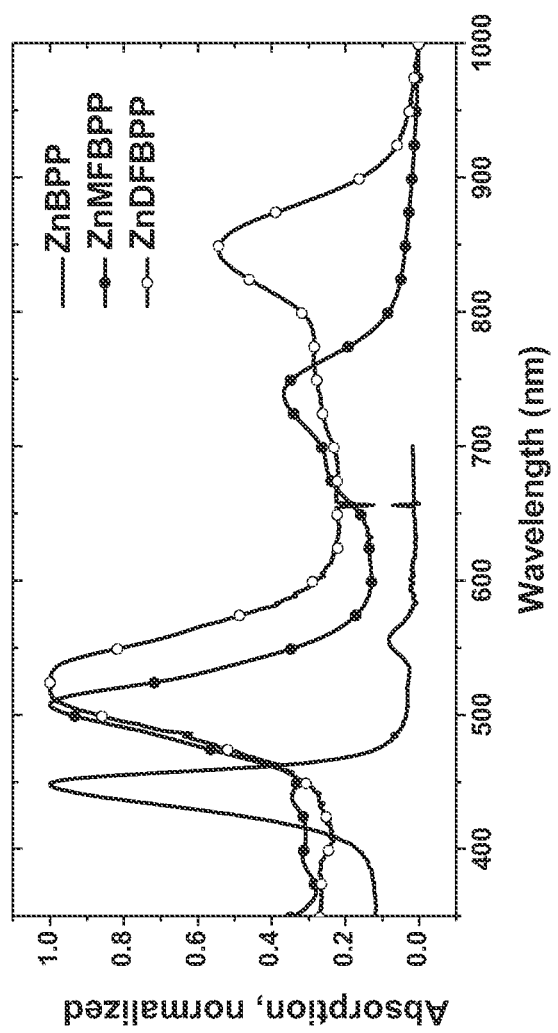
FIG. 3 shows the absorption spectra of ZnBPP, ZnMFBPP, ZnDFBPP in the thin film.
Figure 4:
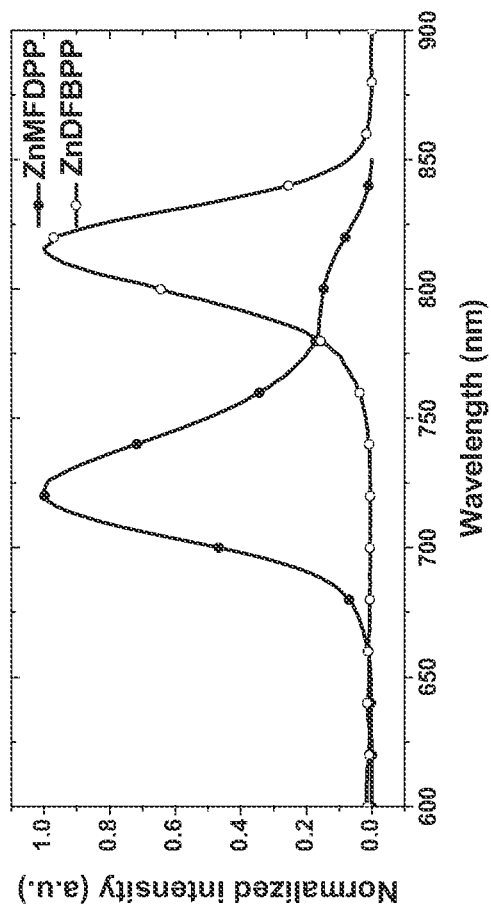
FIG. 4 shows room temperature emission spectra of ZnMFBPP, ZnDFBPP in dichloromethane.
Figure 5:
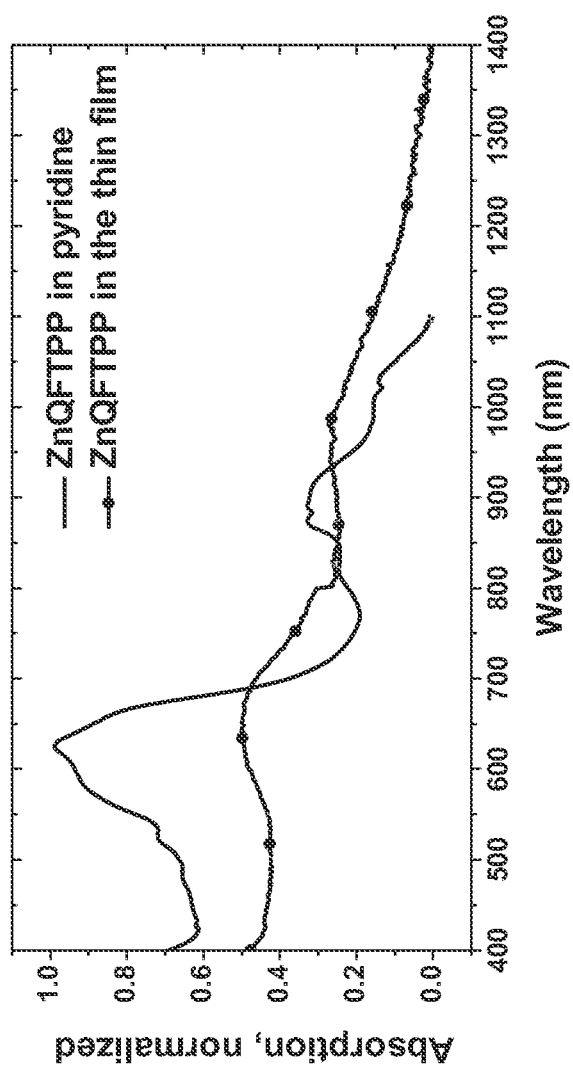
FIG. 5 shows the absorption spectra of ZnQFTPP in pyridine solution and in the thin film

FIG. 1 shows the synthesis of mono (ZnMFBPP), doubly (ZnDFBPP) and quardruply (ZnQFTPP) fused pyrene-porphyrins. FIG. 2 shows the absorption spectra of ZnBPP, ZnMFBPP, ZnDFBPP in dichloromethane solution. FIG. 3 shows the absorption spectra of ZnBPP, ZnMFBPP, ZnDFBPP in the thin film. FIG. 4 shows the room temperature emission spectra of ZnMFBPP, ZnDFBPP in dichloromethane. FIG. 5 shows the absorption spectra of ZnQFTPP in pyridine solution and in the thin film.

Fusion with heterocyclic rings is also potentially interesting reaction to get heterocyclic-fused porphyrins. No reactions of direct fusion of heterocyclic rings with porphyrins have been reported so far. Thiophenes and thiophene-containing compounds represent one of the most useful heterocyclic system for organoelectronics and the inventors were able to achieve direct fusion of 3-substituted thiophene ring to porphyrins in (meso,β) mode with the formation of fused thiophene-porphyrin hybrid, which can be done both by thermal flash pyrolysis and by iron(III) chloride mediated ring closure.

Figure 6:
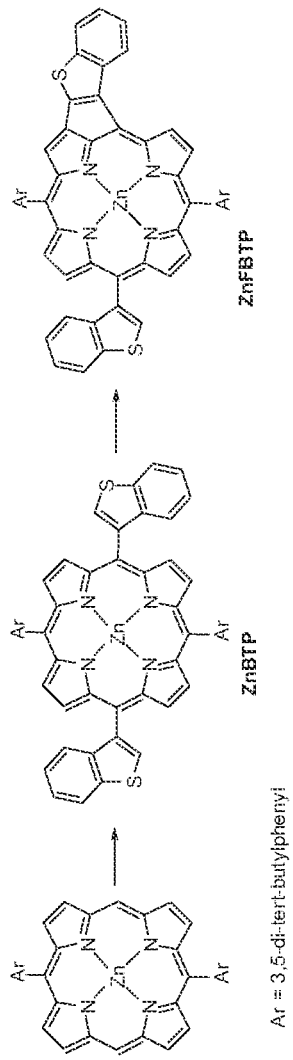
FIG. 6 illustrates the synthesis of ZnBTP and ZnFBTP.
Figure 7:
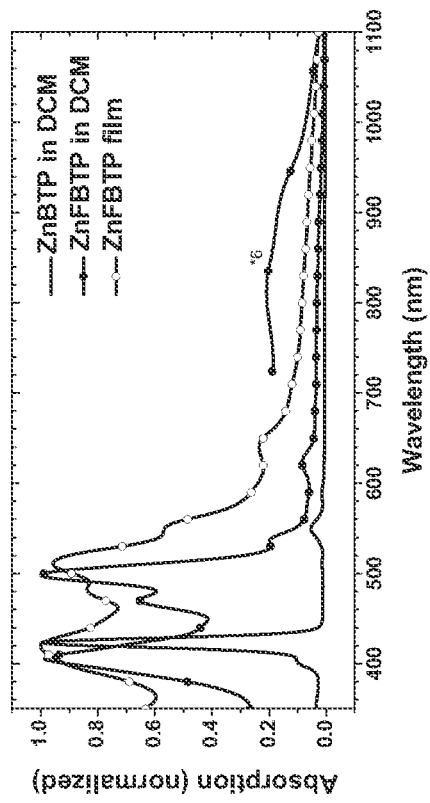
FIG. 7 shows the absorption spectra of ZnBTP and ZnFBTP in dichloromethane solution and in the thin film.

FIG. 6 shows synthesis of ZnBTP and ZnFBTP. FIG. 7 shows the absorption spectra of ZnBTP and ZnFBTP in dichloromethane solution and in the thin film.

Figure 8:
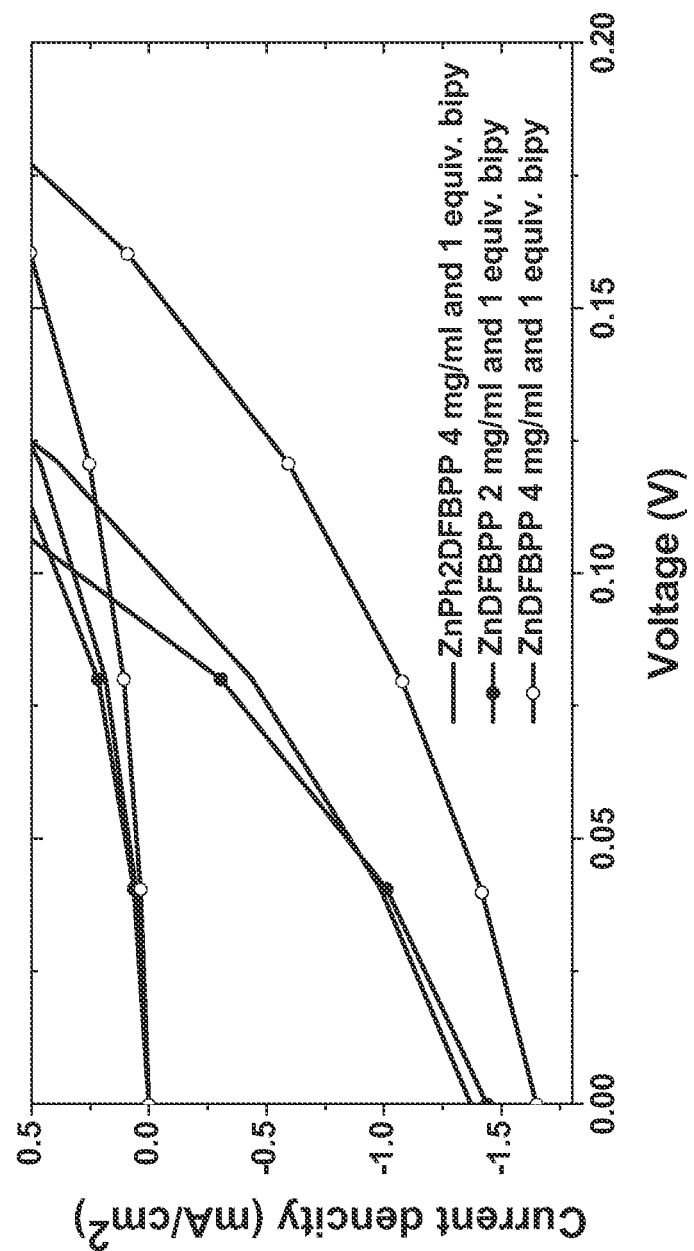
FIG. 8 shows the JV characteristics for ZnDFBPP and ZnPh2DFBPP in ITO/spin-cast porphyrin layer (100 Å)/C$_{60}$ (400 Å)/BCP (100 Å)/Al(1000 Å) devices.
Figure 8A:
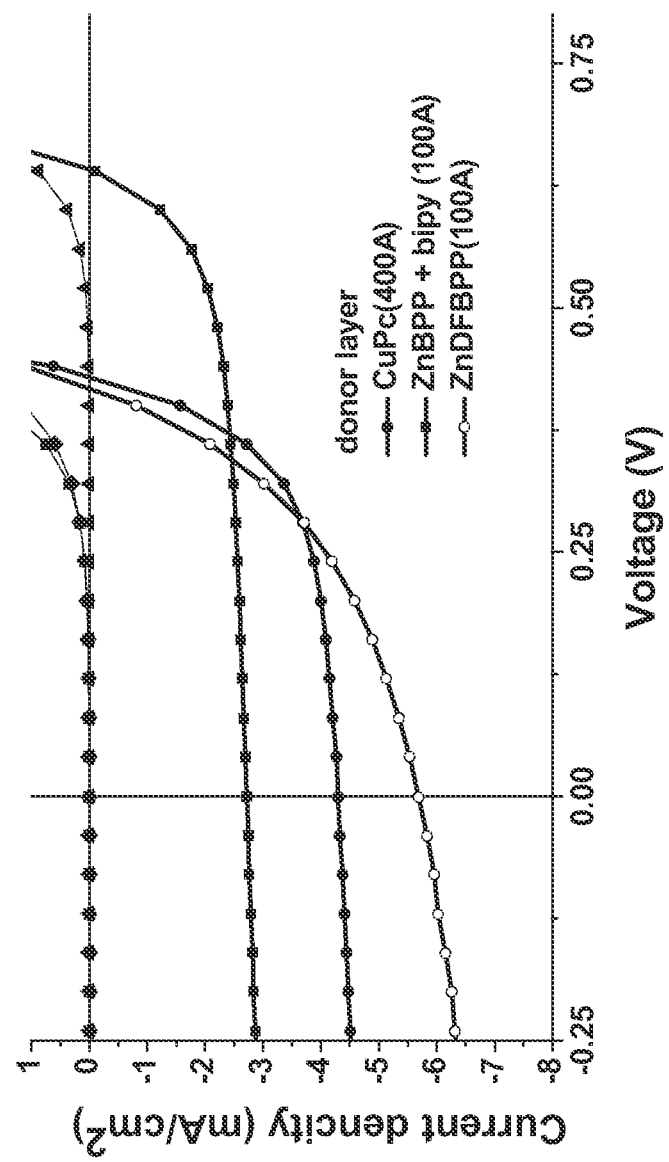
FIG. 8a shows the JV characteristics for ZnDFBPP in ITO/ZnDFBPP(100 Å)/C$_{60}$ (400 Å)/BCP (100 Å)/Al(1000 Å) devices. Conventional reference device using 400 Å copper phthalocyanine (CuPc) as donor layer and device using spin-cast donor layer of ZnBPP with addition of 4,4'-bipyridine also shown for reference.

The fused non-activated porphyrins have absorption shifted to deep red and NIR spectral regions and are promising materials to get high efficiency solar cells and for other applications, where NIR spectral region is critically important for device performance. These materials can provide better exciton diffusion length and better charge transport. FIGS. 8-12 show various measured performance characteristics of some examples of photovoltaic devices fabricated with fused porphyrins as the organic donor material. FIG. 8 shows the JV characteristics for ZnDFBPP and ZnPh2DFBPP in ITO/spin-cast porphyrin layer(100 Å)/C$_{60}$ (400 Å)/BCP (100 Å)/Al(1000 Å) devices as measured by the inventors. FIG. 8a shows the JV characteristics for ZnDFBPP in ITO/ZnDFBPP(100 Å)/C$_{60}$(400 Å)/BCP (100 Å)/Al(1000 Å) devices as measured by the inventors. The IV characteristics of conventional devices, one using 400 Å copper phthalocyanine (CuPc) as the donor layer and another using the spin-cast donor layer of ZnBPP (see FIG. 1) with addition of 4,4'-bipyridine are also shown in FIG. 8a for reference.

The π-systems of the fused pyrene moieties in ZnDFBPP are not sterically hindered and are, therefore, suitable for intermolecular attractive pyrene-pyrene interactions. This leads to significant red-shifted absorption in the thin films (up to 90 nm in some cases, for example by spin-casting from toluene). Conversely, porphyrin ZnDFBPP has two bulky di-tert-butyl phenyl groups at the meso positions of the porphyrin ring, limiting direct overlap with the π-system of the porphyrin chromophore. Control of such intermolecular interactions has been implicated as an important factor in kinetically suppressing losses to open circuit voltage ($V_{oc}$), which is thermodynamically limited by the interfacial energy level offset ($\Delta E_{DA}$) between HOMO$_{donor}$-LUMO$_{acceptor}$. where HOMO is highest occupied molecular orbital and LUMO is lowest unoccupied molecular orbital FIG. 8 illustrates the performance of solar cells (the current density vs. voltage (J-V) characteristics) incorporating fused pyrene porphyrin ZnDFBPP as a donor by using spin-casting technique. FIG. 8a illustrates the performance of solar cells (the current density vs. voltage (J-V) characteristics) incorporating fused pyrene porphyrin ZnDFBPP as a donor and reference copper phthalocyanine (CuPc) cell by thermal evaporation, and reference ZnBPP/4,4'-bipyridyl cell by using spin-casting technique. The cell structure is ITO/ZnDFBPP(100 Å)/C$_{60}$(400 Å)/BCP(100 Å)/Al(1000 Å), similar to that used for the copper phthalocyanine (CuPc) reference cell and related porphyrin donor based cells. The current density vs. voltage (J-V) characteristics were measured in the dark and under simulated 1 sun (1 kW/m$^2$) AM1.5G illumination. Efficiencies were determined after correction for spectral mismatch between Xe source lamp and ASTM G173-03 global. Overall, thin layers (100 Å) of thermally evaporated, porphyrin ZnDFBPP yield a power conversion efficiency (PCE)>1%, which is close to that of the reference (CuPc, 400 Å/C$_{60}$) device. The open circuit voltage of porphyrin ZnDFBPP and CuPc are comparable, even though $\Delta E_{DA}$ for CuPc/C$_{60}$ couple is larger (1.7 eV) than that for porphyrin ZnDFBPP/C$_{60}$ (1.1 eV). This underscores the importance of attending to molecular structure when considering materials to suppress losses in $V_{oc}$. The short circuit current-density of $J_{sc}$=5.69 mA/cm$^2$ obtained for the porphyrin ZnDFBPP device is among the highest values reported for porphyrin solar cells and 32% higher than for standard CuPc cell. This enhancement appears to be due to panchromatic response up to 950 nm, with peak values of >7% in the 850-900 nm region (FIG. 9a). The relatively high EQE demonstrates the utility of employing intense broadband absorption throughout the visible and NIR for achieving enhanced solar energy conversion efficiency.

Figure 9:
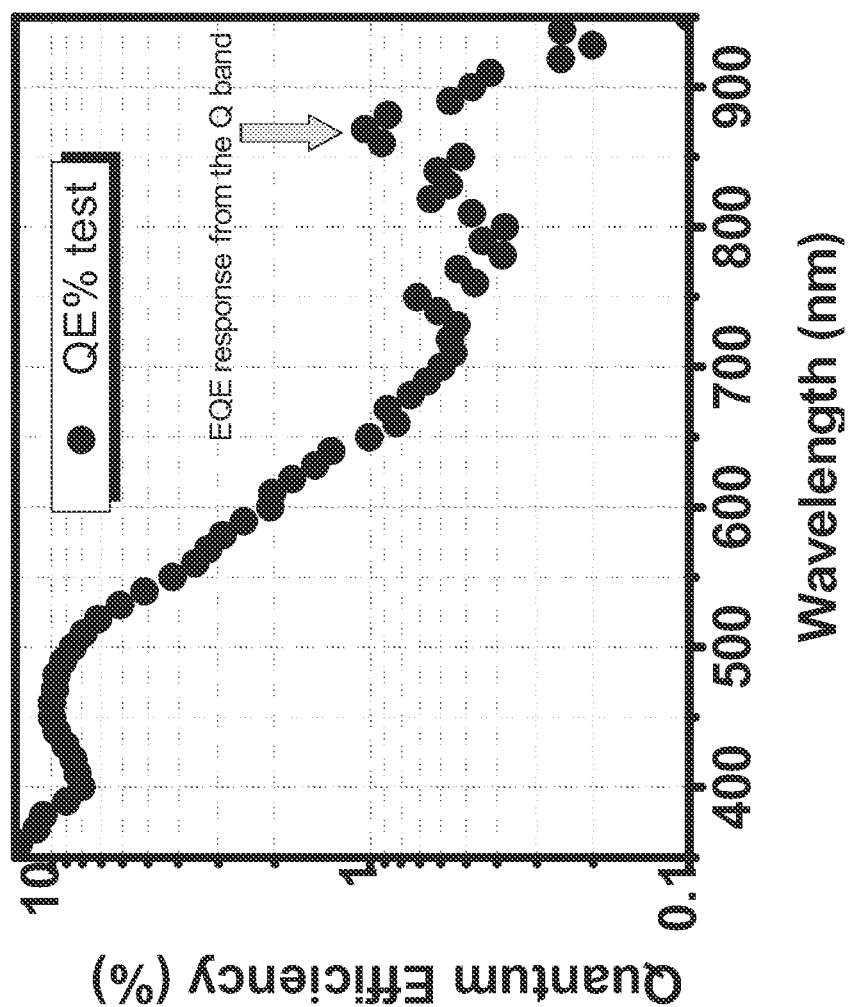
FIG. 9 shows the EQE response for ZnDFBPP in ITO/spin-cast porphyrin layer(100 Å)/C$_{60}$(400 Å)/BCP (100 Å)/Al (1000 Å) devices.
Figure 9A:
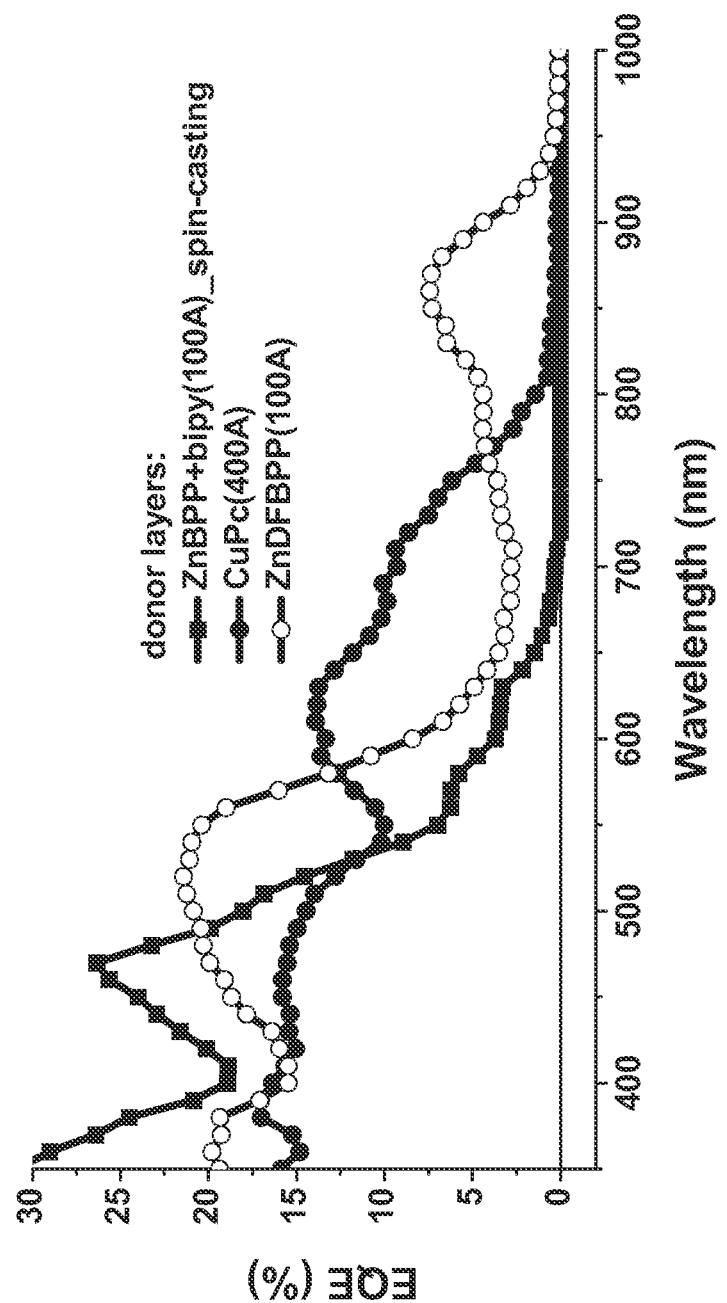
FIG. 9a shows the EQE response for ZnDFBPP in ITO/donor layer(100 Å)/C$_{60}$(400 Å)/BCP (100 Å)/Al(1000 Å) device, a reference device using 400 ÅCuPc as the donor layer and another reference device using spin-cast donor layer of ZnBPP with addition of 4,4'-bipyridine also shown for reference.

FIG. 9 illustrates the performance of solar cells (EQE response) incorporating fused pyrene porphyrin ZnDFBPP as a donor by using spin-casting technique. FIG. 9a illustrates the performance of solar cells (EQE; response) incorporating fused, pyrene porphyrin ZnDFBPP as a donor and reference copper phthalocyanine (CuPc) cell by thermal evaporation, and reference ZnBPP/4,4'-bipyridyl cell by using spin-casting technique. The cell structure is ITO/ZnDFBPP(100 Å)/C$_{60}$(400 Å)/BCP(100 Å)/Al(1000 Å), similar to that used for the copper phthalocyanine (CuPc) reference cell and related porphyrin donor based cells. FIG. 9a shows one of the best NIR EQE response for organic dyes of 7.5% at peak max=860 nm.

Figure 10:
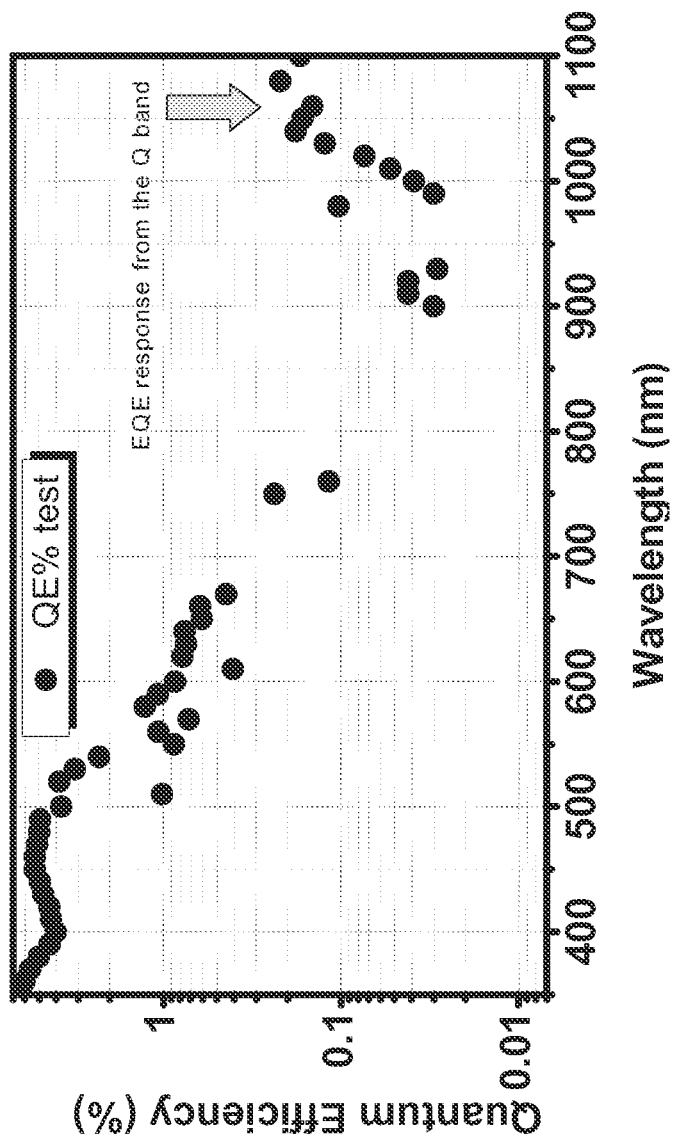
FIG. 10 shows the EQE response for in situ generated by thermal annealing at 530° C. ZnQFTPP in ITO/porphyrin (100 Å)/C$_{60}$(400 Å)/BCP (100 Å)/Al(1000 Å) devices.
Figure 11:
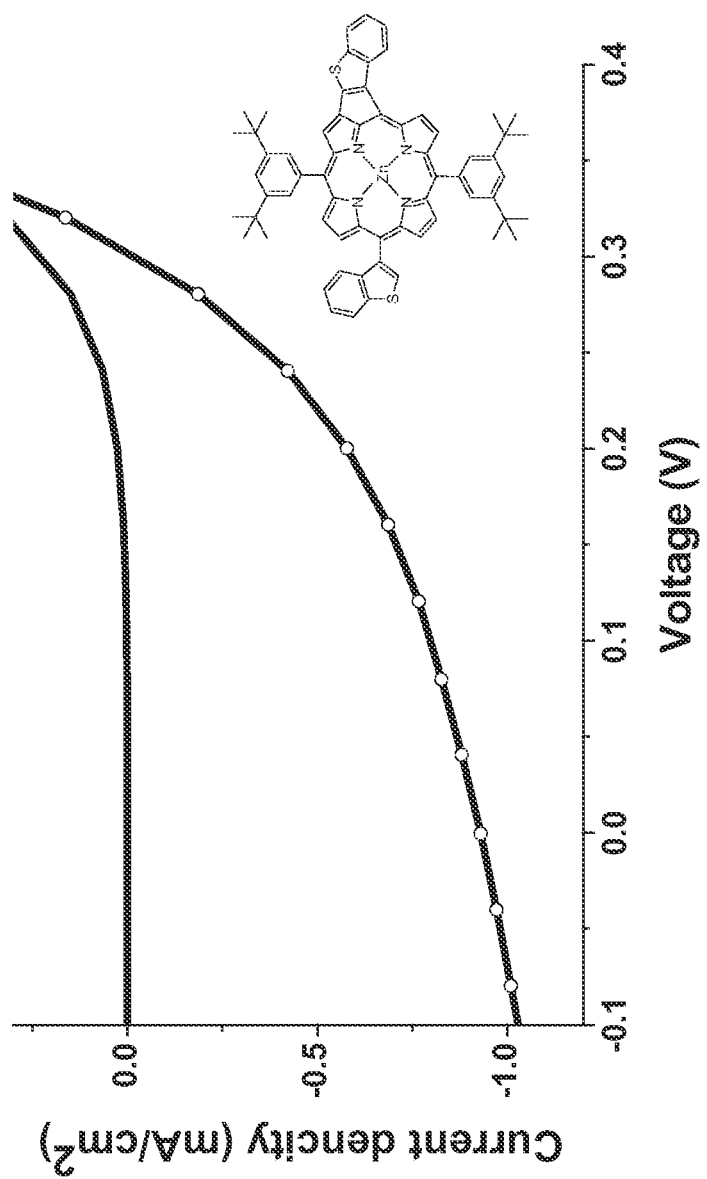
FIG. 11 shows the JV characteristics for ZnFBTP in ITO/porphyrin(100 Å)/C$_{60}$(400 Å)/BCP (100 Å)/Al(1000 Å) devices.
Figure 12:
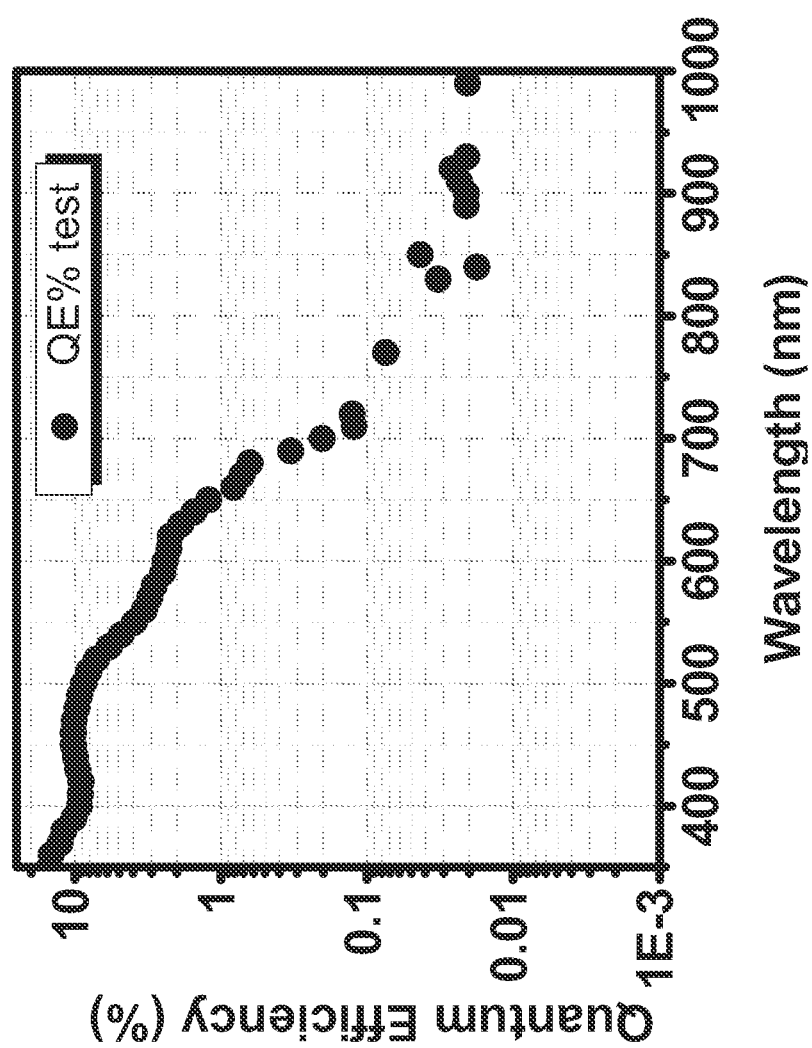
FIG. 12 shows the EQE response for ZnFBTP in ITO/porphyrin(100 Å)/C$_{60}$(400 Å)/BCP (100 Å)/Al(1000 Å) devices.

FIG. 10 shows the EQE response for ZnQFTPP in ITO/porphyrin(100 Å)/$C_{60}$(400 Å)/BCP (100 Å)/Al(1000 Å) devices generated in situ by thermal annealing at 530° C. Thermal annealing of starting porphyrins can be done in situ on ITO or other transparent electrode just by spin-casting of non-fused, porphyrins (e.g. ZnBPP, ZnTPP) and annealing at 530° C. under nitrogen for 5 minutes, these films can be used for device fabrication directly without further processing the donor layer. FIG. 11 shows the JV characteristics for ZnFBTP in ITO/ZnFBTP(100 Å)/$C_{60}$(400 Å)/BCP (100 Å)/Al(1000 Å) devices as measured by the inventors, FIG. 12 shows the EQE response for ZnFBTP in ITO/porphyrin(100 Å)/$C_{60}$ (400 Å)/BCP (100 Å)/Al(1000 Å) devices as measured by the inventors. This data shows that porphyrins fused with heterocyclic rings can also be used as donor layers for organic solar cells. FIG. 12 illustrates the performance of solar cells (EQE response) incorporating benzothienyl-fused porphyrin ZnFBTP as a donor by thermal evaporation with photovoltaic response from porphyrin extended, up to 1100 nm.

Figure 13:
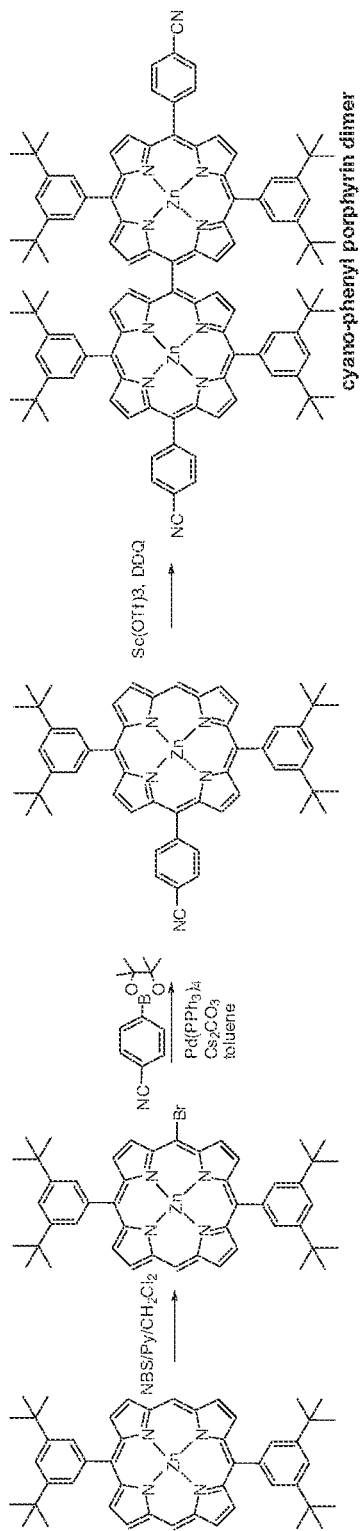
FIG. 13 illustrates the synthesis of cyanophenyl porphyrin dimer.
Figure 14:
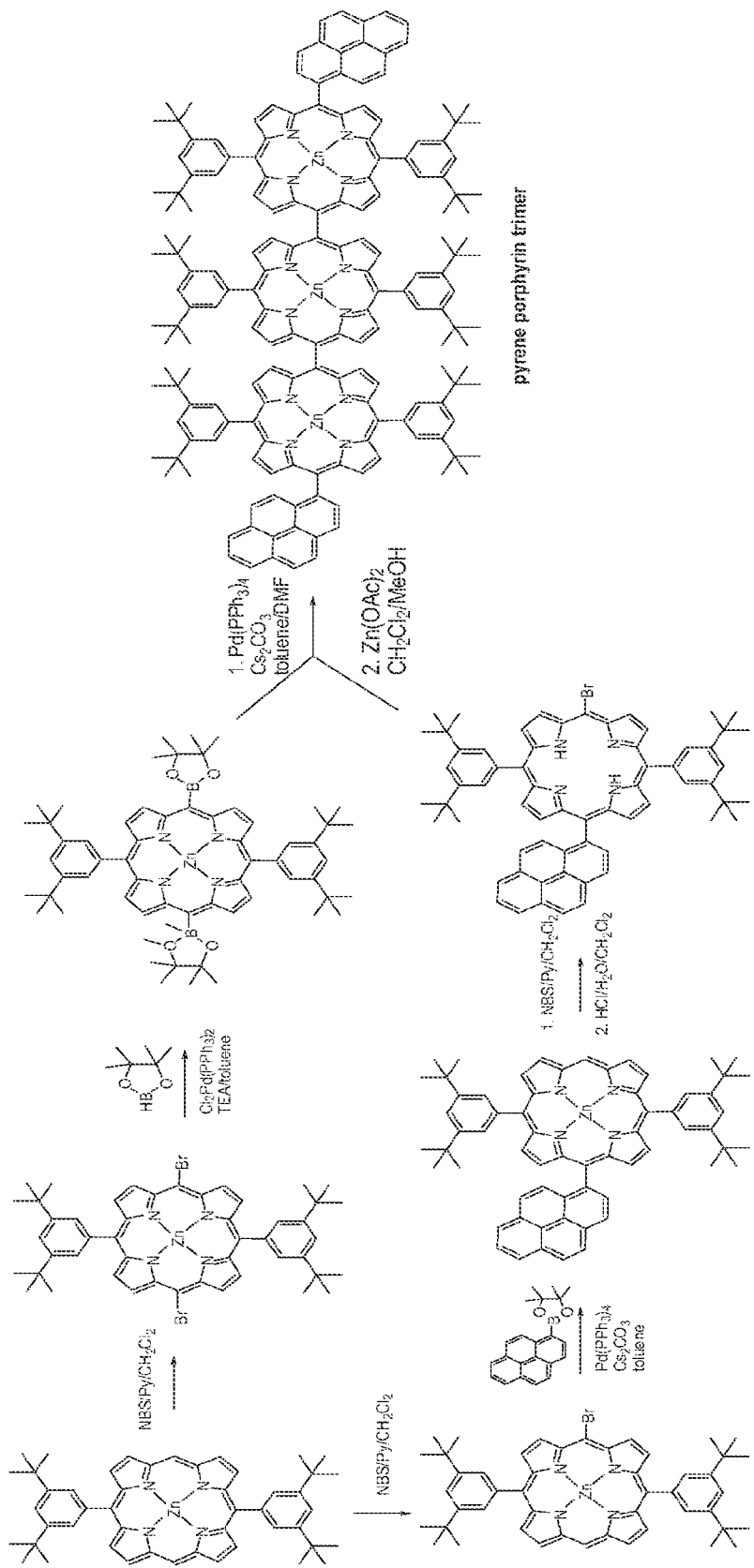
FIG. 14 illustrates the synthesis of pyrene porphyrin trimer.
Figure 15:
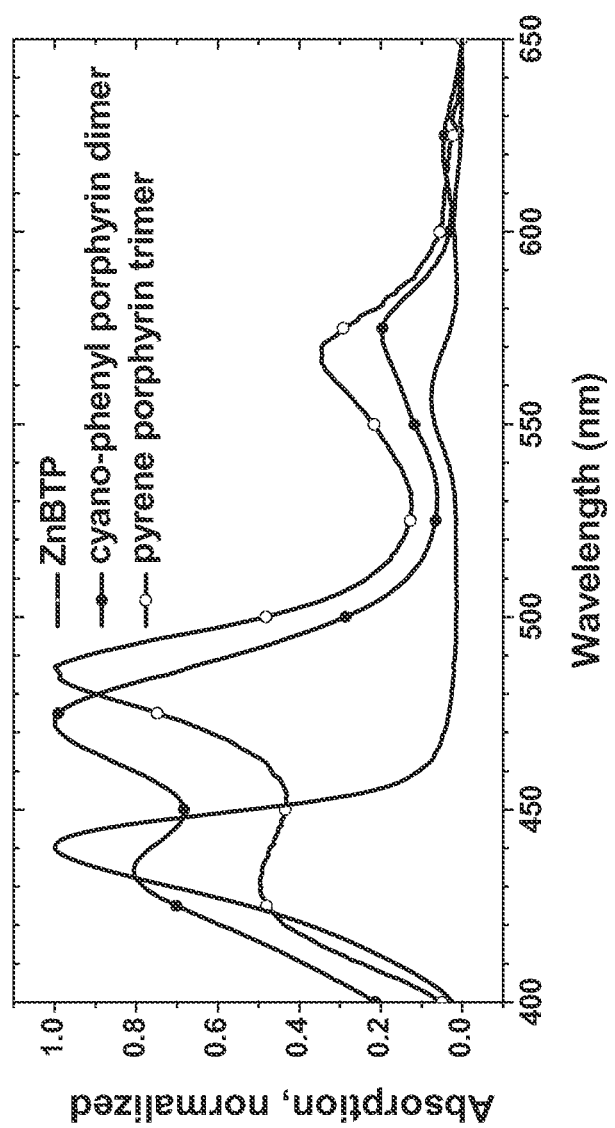
FIG. 15 shows the UV/VIS spectra of ZnBTP, cyano-phenyl porphyrin dimer and pyrene porphyrin trimer in the thin film.
Figure 16:
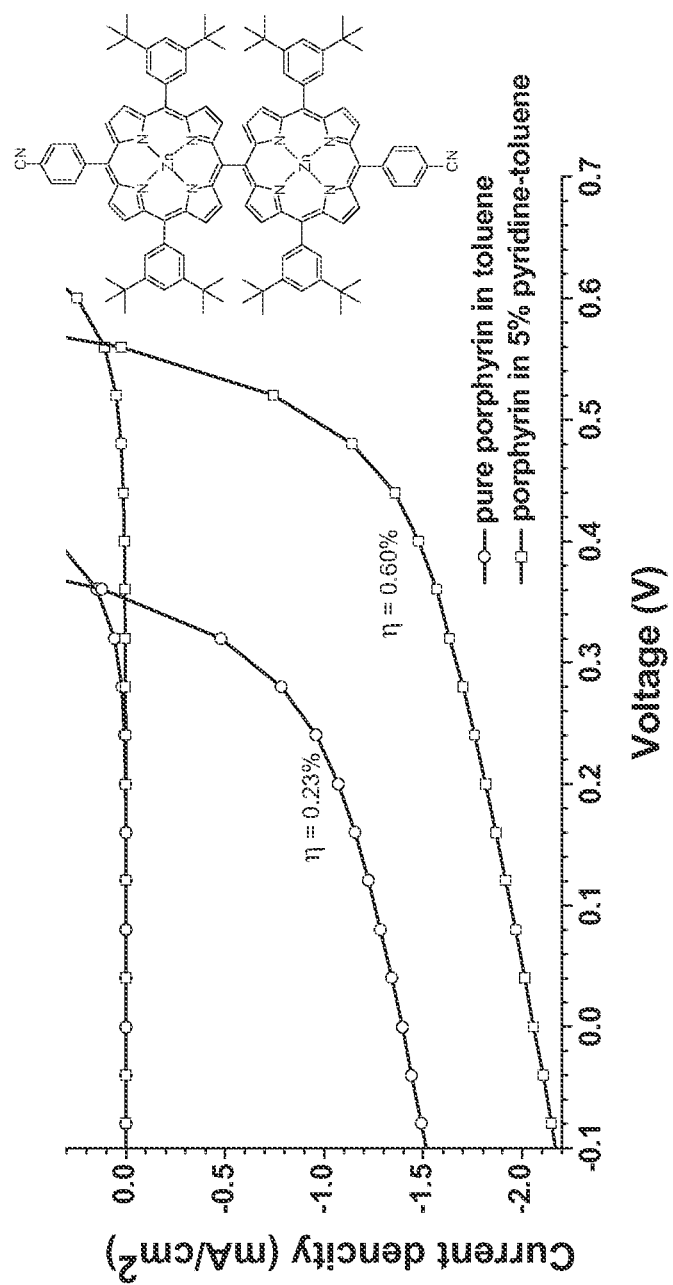
FIG. 16 shows the JV characteristics for cyano-phenyl porphyrin dimer in ITO/porphyrin(100 Å)/C$_{60}$(400 Å)/BCP (100 Å)/Al(1000 Å) devices.
Figure 17:
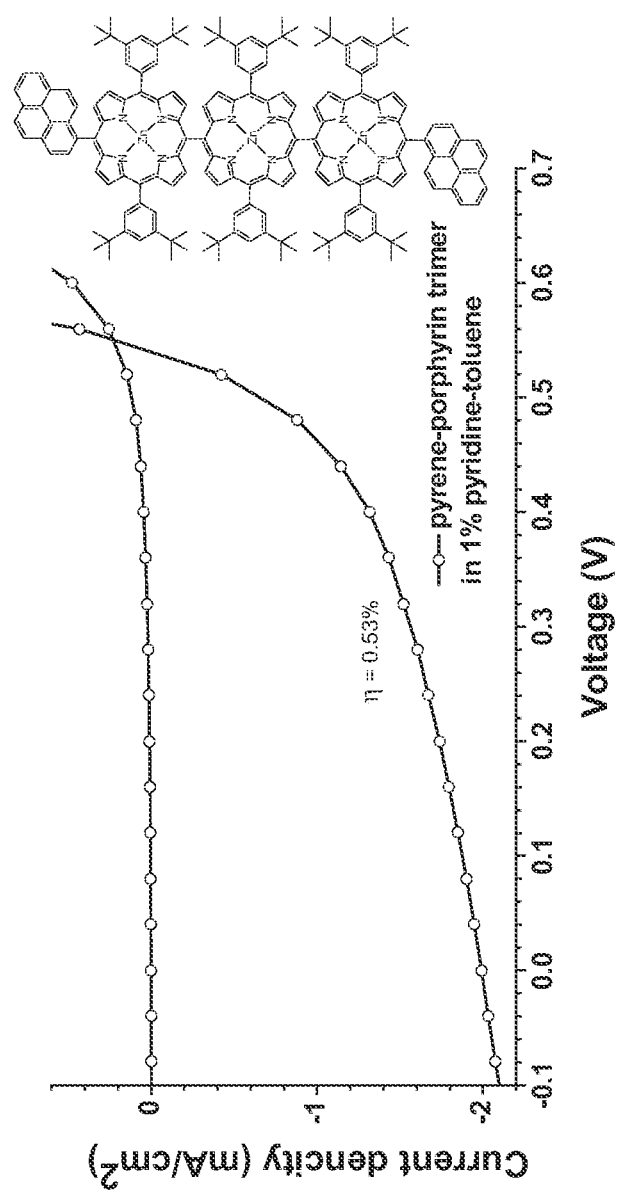
FIG. 17 shows the JV characteristics for pyrene porphyrin trimer in ITO/porphyrin(75 Å)/C$_{60}$(400 Å)/BCP (100 Å)/Al (1000 Å) devices.

Olygoporphyrins singly connected at meso position were never applied to photovoltaic (PV) devices before. Such porphyrin olygomers can be used in PV devices with or without coordinative additives. Such porphyrin olygomers are shown in FIGS. 13-17 and 25. FIG. 13 shows the synthesis of a porphyrin dimer, specifically a cyano-phenyl porphyrin dimer. FIG. 14 shows synthesis of pyrene porphyrin trimer, FIG. 15 shows UV/VIS spectra of ZnBTP, cyano-phenyl porphyrin dimer and porphyrin trimer in the thin film as measured, by the inventors, FIG. 16 shows the JV characteristics for cyano-phenyl porphyrin dimer in ITO/porphyrin(100 Å)/$C_{60}$(400 Å) BCP (100 Å)/Al(1000 Å) devices as measured by the inventors. FIG. 17 shows the JV characteristics for pyrene porphyrin trimer in ITO/porphyrin(75 Å)/$C_{60}$(400 Å)/BCP (100 Å)/Al(1000 Å) devices as measured by the inventors. Photophysical properties of olygoporphyrins are different from monoporphyrins. Some examples are: faster hole hopping from one porphyrin unit to another; and porphyrin units are electronically coupled much stronger than two separate porphyrin units. This causes broadening of absorption spectrum with better overlap with solar spectrum (see FIG. 15). Besides that electronic coupling between porphyrin units should potentially provide better charge transport which is essential for getting materials with larger exciton diffusion length. Some problems involving applications of olygoporphyrins include film morphology (formation of aggregates), poor solubility, etc. The data in FIGS. 16 and 17 shows that olygoporphyrins (dimer, trimer) give photoresponse as donor layers by using spin-casting technique meaning that there is no problems with morphology of thin films, charge separation and charge transport. Therefore, this opens opportunities for their applications in devices with various architecture where olygoporphyrins serve as donor materials. Advantages of olygoporphyrins can be better organization of the thin films together with better overlap with solar spectrum as illustrated by FIG. 15.

According to another aspect of the present disclosure, the use of coordinative additives to porphyrins, pthalocyanines, subphthalocyanines in a donor/acceptor configuration typical with common organic solar cells (i.e. copper phthalocyanine/$C_{60}$) will now be described. In our initial implementation, we used porphyrins, porphyrin oligomers, phthalocyanines and subphthalocyanines with coordinative additives, such as pyridines, as donors and paired them with the acceptor $C_{60}$.

By coordination of the above mentioned macrocycles with coordinative additives containing, for example, basic nitrogen atom gives possibility to change and tune the energy levels of macrocycles as well as change the morphology of the thin films. From the data obtained by the inventors and shown in FIGS. 16-20, it is clear that addition of such representative coordinative compounds as pyridine and 4,4'-bipyridyl, containing one basic nitrogen atom (pyridine) or two basic nitrogen atoms (4,4'-bipyridyl) significantly improves performance of the photovoltaic cells.

Figure 19:
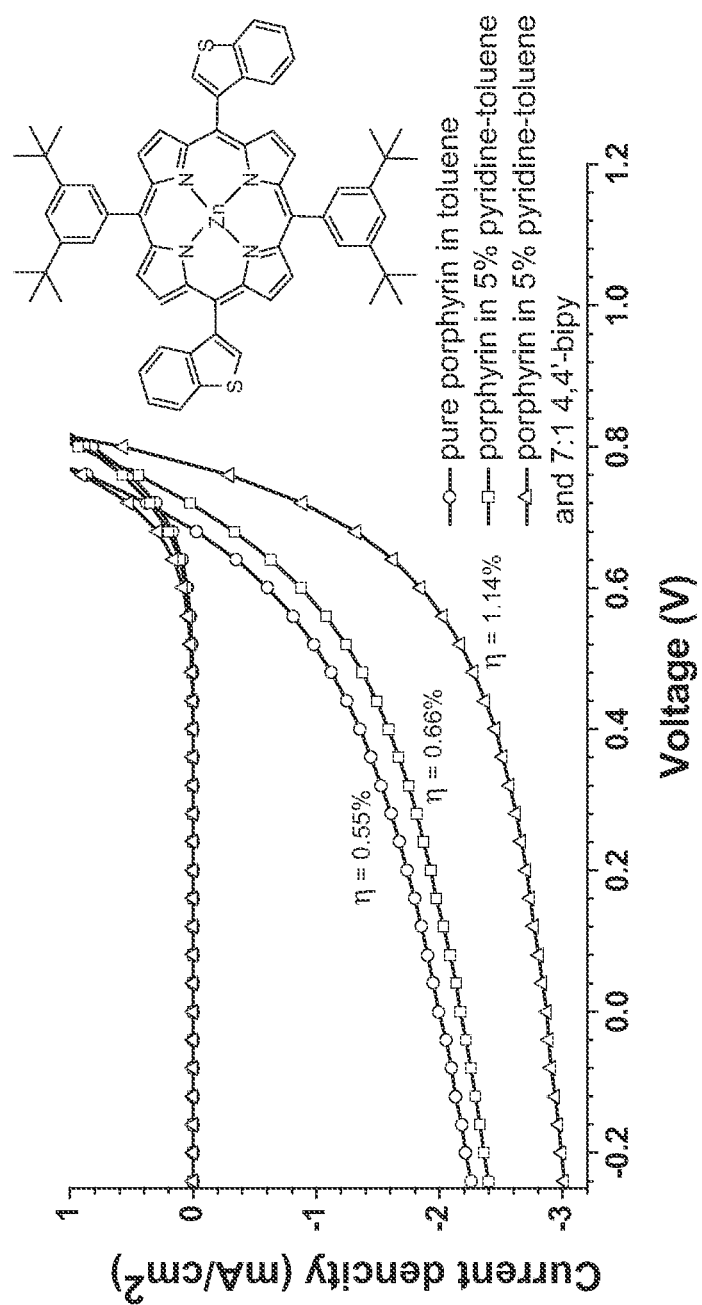
FIG. 19 shows the JV characteristics for ZnBTP in ITO/porphyrin(100 Å)/C$_{60}$(400 Å)/BCP (100 Å)/Al(1000 Å) devices.

First, the addition of coordination additives prevents aggregation giving much better open circuit voltages especially for compounds with pronounced, tendency for aggregation—from 0.3 V to 0.44 V for diphenyl porphyrin (FIG. 20), from 0.35 V to 0.56 V for porphyrin dimer (FIG. 16). Secondly, the addition of coordination additives improves Jsc and fill factor as well. This can be illustrated, for example, by increasing Jsc from 2.17 to 2.87 mA/cm$^2$ and fill factor from 0.42 to 0.51 for benzothiophene substituted porphyrin (FIG. 19). Examples: FIG. 16 shows the JV characteristics for porphyrin dimer as one of the representative members of olygoporphyrins in ITO/porphyrin(100 Å)/$C_{60}$(400 Å)/BCP (100 Å)/Al(1000 Å) devices by using spin-casting method to deposit a porphyrin layer. This demonstrates the utility of olygoporphyrins as donor layers in organic photovoltaic cells. Device performance is significantly improved by using coordination additives, such as 4,4'-bipyridyl, which prevents aggregation and increases open circuit voltage, short circuit current and fill factor. The overall device performance can be improved by more than 2 times.

Figure 18:
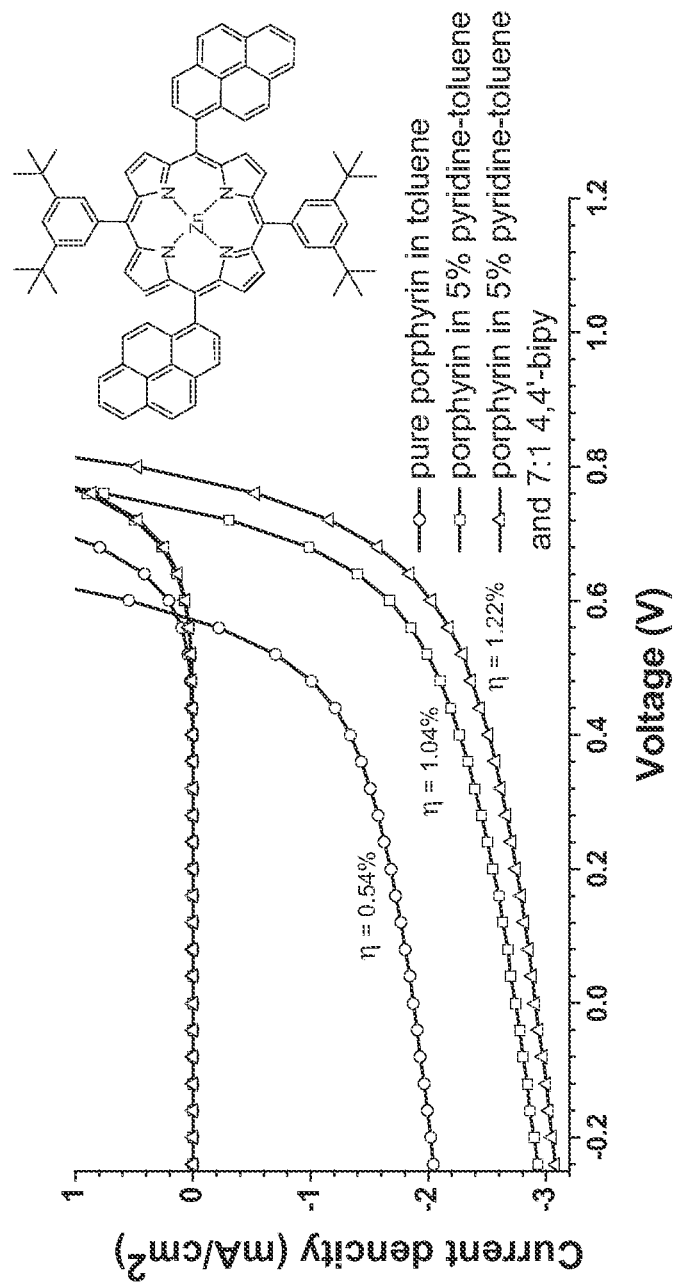
FIG. 18 shows the JV characteristics for bis-pyrene porphyrin in ITO/porphyrin(100 Å)/C$_{60}$(400 Å)/BCP (100 Å)/Al (1000 Å) devices.
Figure 20:
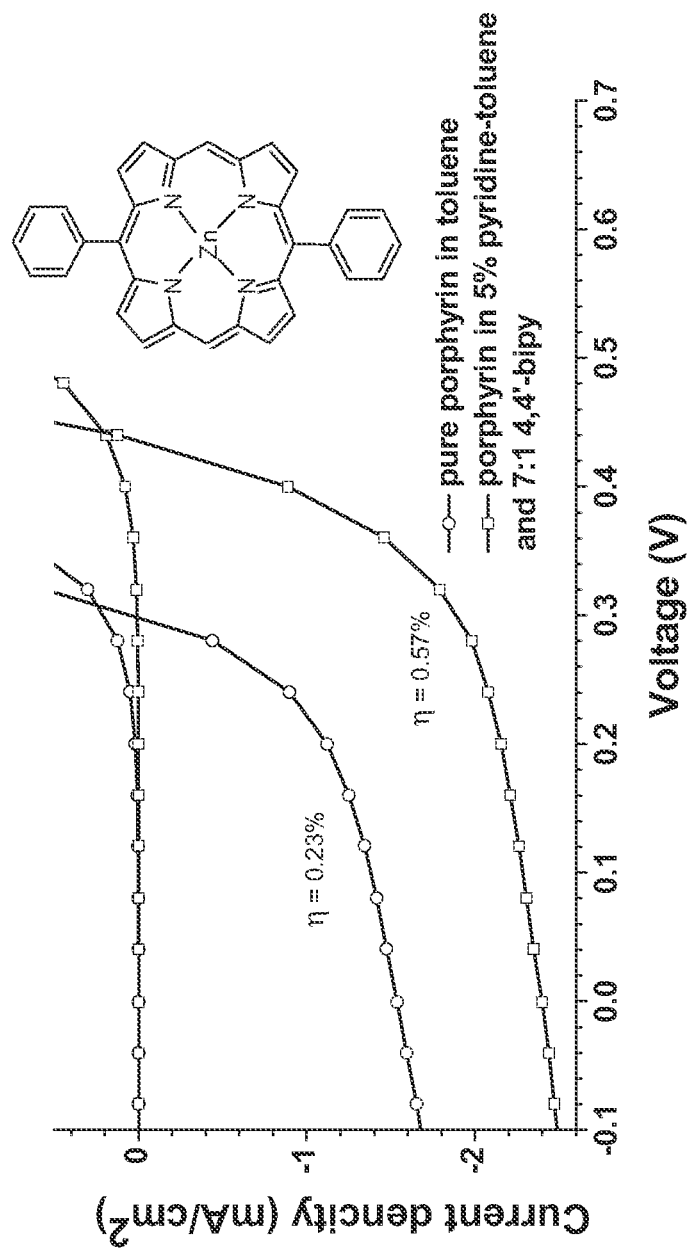
FIG. 20 shows the JV characteristics for diphenyl porphyrin in ITO/porphyrin(100 Å)/C$_{60}$(400 Å)/BCP (100 Å)/Al (1000 Å) devices.

FIG. 18 shows the JV characteristics for bis-pyrene porphyrin ZnBPP in ITO/porphyrin(100 Å)/$C_{60}$(400 Å) BCP (100 Å)/Al(1000 Å) devices by using spin-casting method to deposit the porphyrin layer. Device performance is improved by almost 2 times by using pyridine as a coordination additive and further improved by about 20% by using 4,4'-bipyridyl as a coordination additive. The use of coordination additives increases open circuit voltage, short circuit current and fill factor, and, thus, overall performance by about 2.25 times. FIG. 19 shows the JV characteristics for bis-(3-benzothienyl)-porphyrin in ITO/porphyrin(100 Å)/$C_{60}$(400 Å)/BCP (100 Å)/Al(1000 Å) devices by using spin-casting method to deposit the porphyrin layer. Device performance is improved by about 2 times by using pyridine as a coordination additive and further by using 4,4'-bipyridyl as a coordination additive. The use of coordination additives increases open circuit voltage, short circuit current and fill factor. FIG. 20 shows the JV characteristics for diphenyl porphyrin in ITO/porphyrin(100 Å)/$C_{60}$(400 Å)/BCP (100 Å)/Al(1000 Å) devices by using spin-casting method to deposit the porphyrin layer. Device performance is improved by using pyridine and further by about 2.5 times using 4,4'-bipyridyl as a coordination additive. This result and the results above suggest that such great improvement in device performance by using additives and spin casting method to deposit donor layer has general applications.

All of the fused porphyrin compounds listed above and those depicted in FIGS. 21-24 are a new class of absorption material for application in organoelectronics. The basic structure of the new material can be seen in FIGS. 21(a)-(p) and FIGS. 23(a)-(g). FIGS. 21(a)-(p) show the basis structures of porphyrins fused with polycyclic aromatic hydrocarbons. FIGS. 23(a)-(g) show the basic structures of pophyrins fused with polycyclic heterocyclic rings. In the compositions shown in FIGS. 21 and 23, M is two hydrogen atoms representing free base porphyrins or any element selected from the following group: Mg, Ca, Sr, Ba, Sc, Y, La, Ce, Ti, Nb, Ta, Cr, Mo, W, Mn, Tc, Re, Fe, Ru, Os, Co, Rh, Ir, Ni, Pd, Pt, Cu, Ag, Au, Zn, Cd, Hg, Al, Ga, In, Tl, Si, Ge, Sri, Pb, P, As, Sb, Bi, Pr, Nd, Sm, Eu, Gd, Tb, Dy, Ho, Er, Tm, Yb, Lu, Th, and U. Each of the $R_1$-$R_{54}$ are independently selected, from the group consisting of electron donors and acceptors, such as hydrogen, alkyl, fluoroalkyl, hydroxyl, alkoxy, halo (Cl, Br, I), chalcogens (S, Se, Te), mercapto group, amino, cyano, alkenyl, alkynyl, and aryl. The terms halo, halogen, alkyl, cycloalkyl, alkenyl, alkynyl, heterocyclic group aryl, aromatic group, and heteroaryl are known to the art and are defined, for example, in U.S. Pat. No. 7,279,704 at cols. 31-32, the disclosure of which is incorporated, herein by reference. In FIGS. 23(a)-(g), X is a heteroatom from the following list: O, S, Se, Te, N, P, As, Si, Ge, B. X can have two bonds as depicted or X can have coordination with additional one, two or three bonds with one, two or three ligands.

Figure 21:
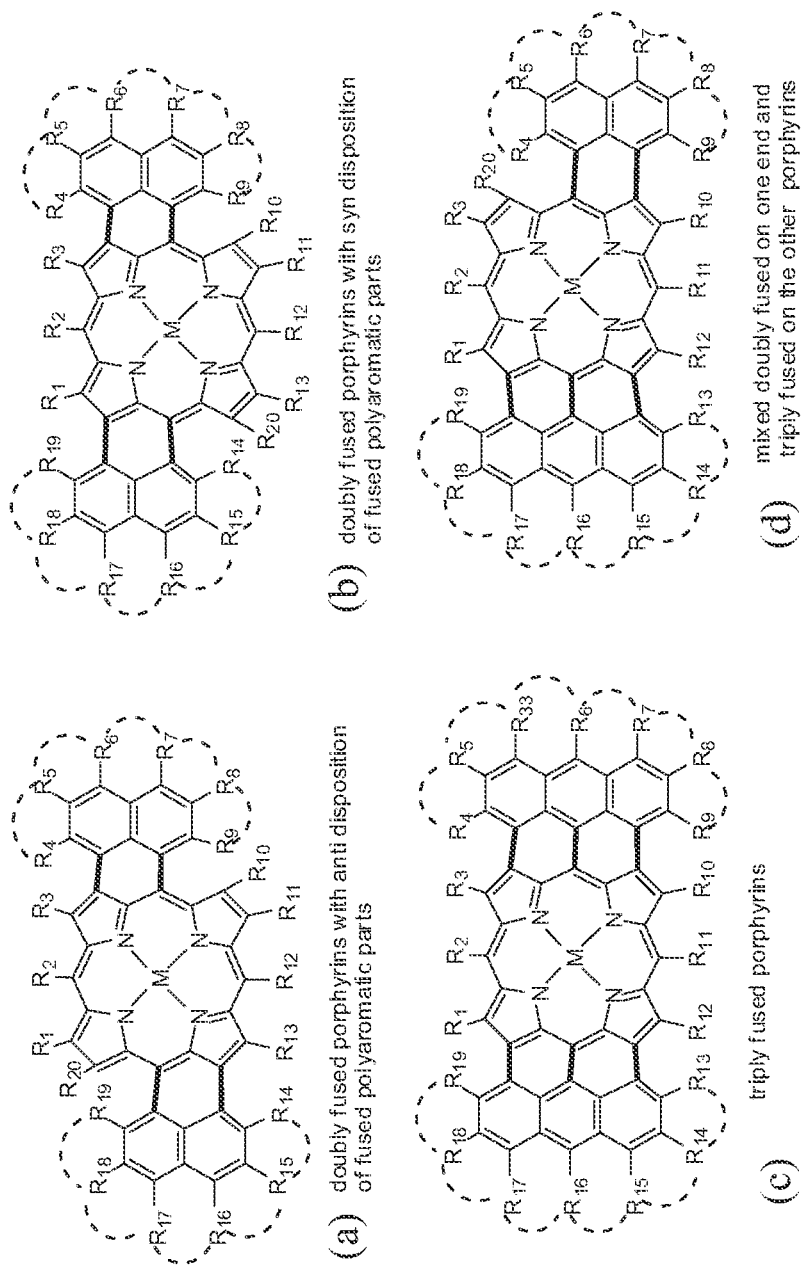
FIGS. 21(a)-21(p) show the various basic structures of porphyrins fused with polycyclic aromatic hydrocarbons according to an embodiment.
Figure 21:
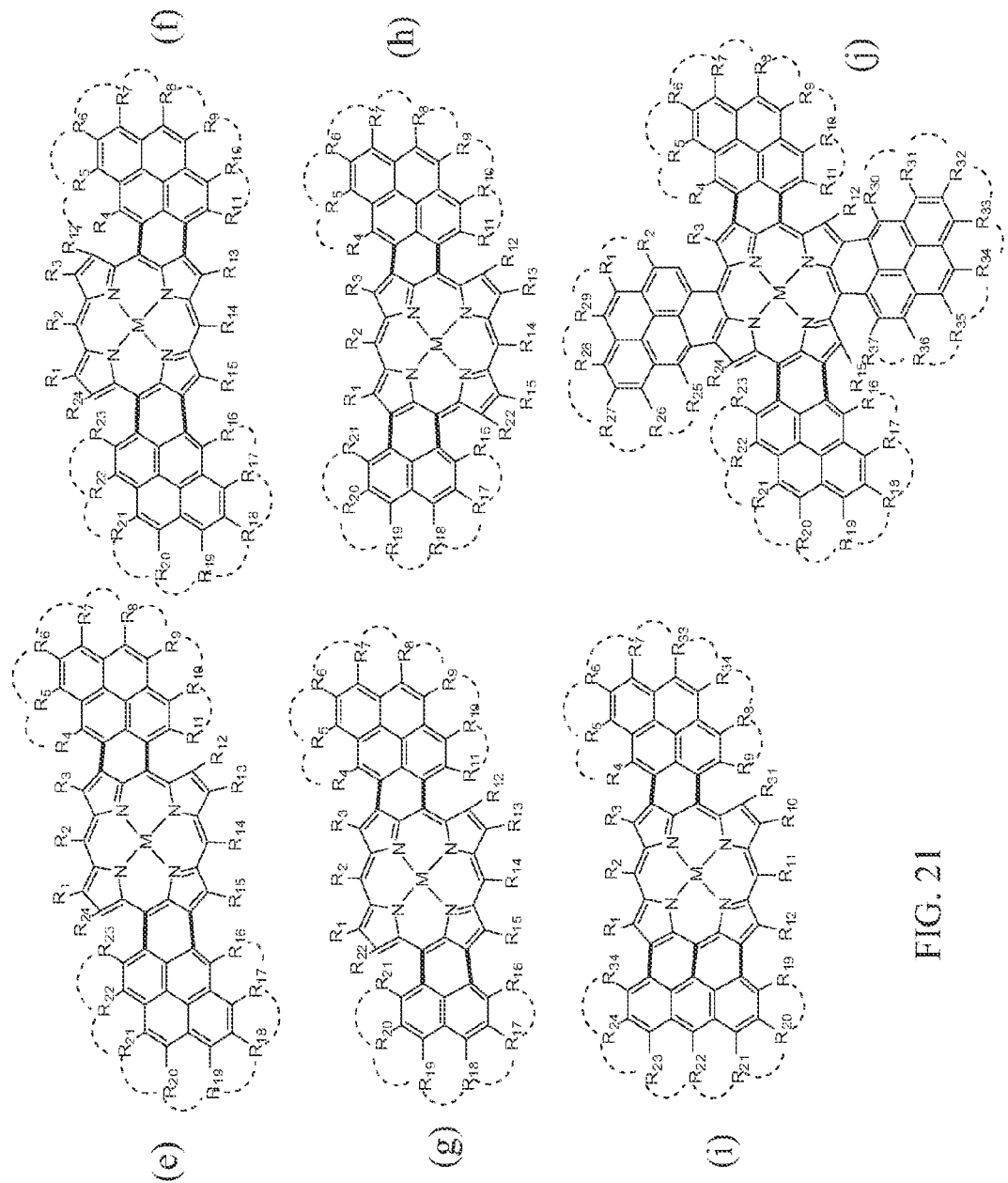
Figure 21:
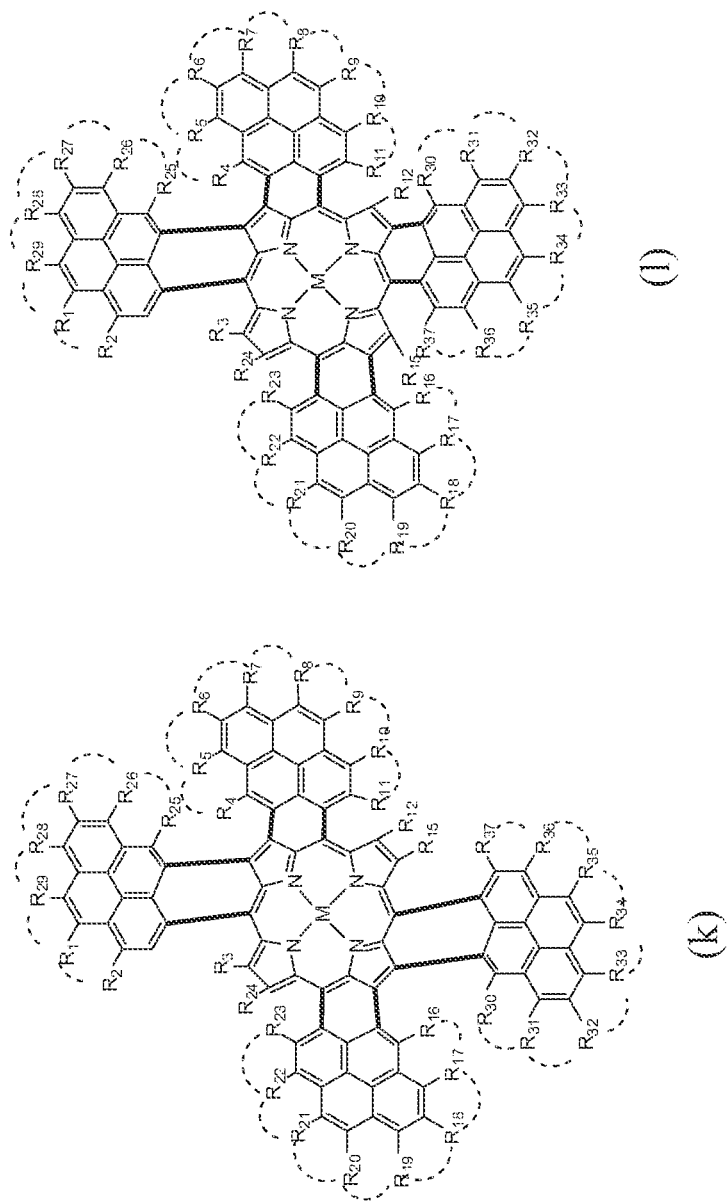
Figure 21:
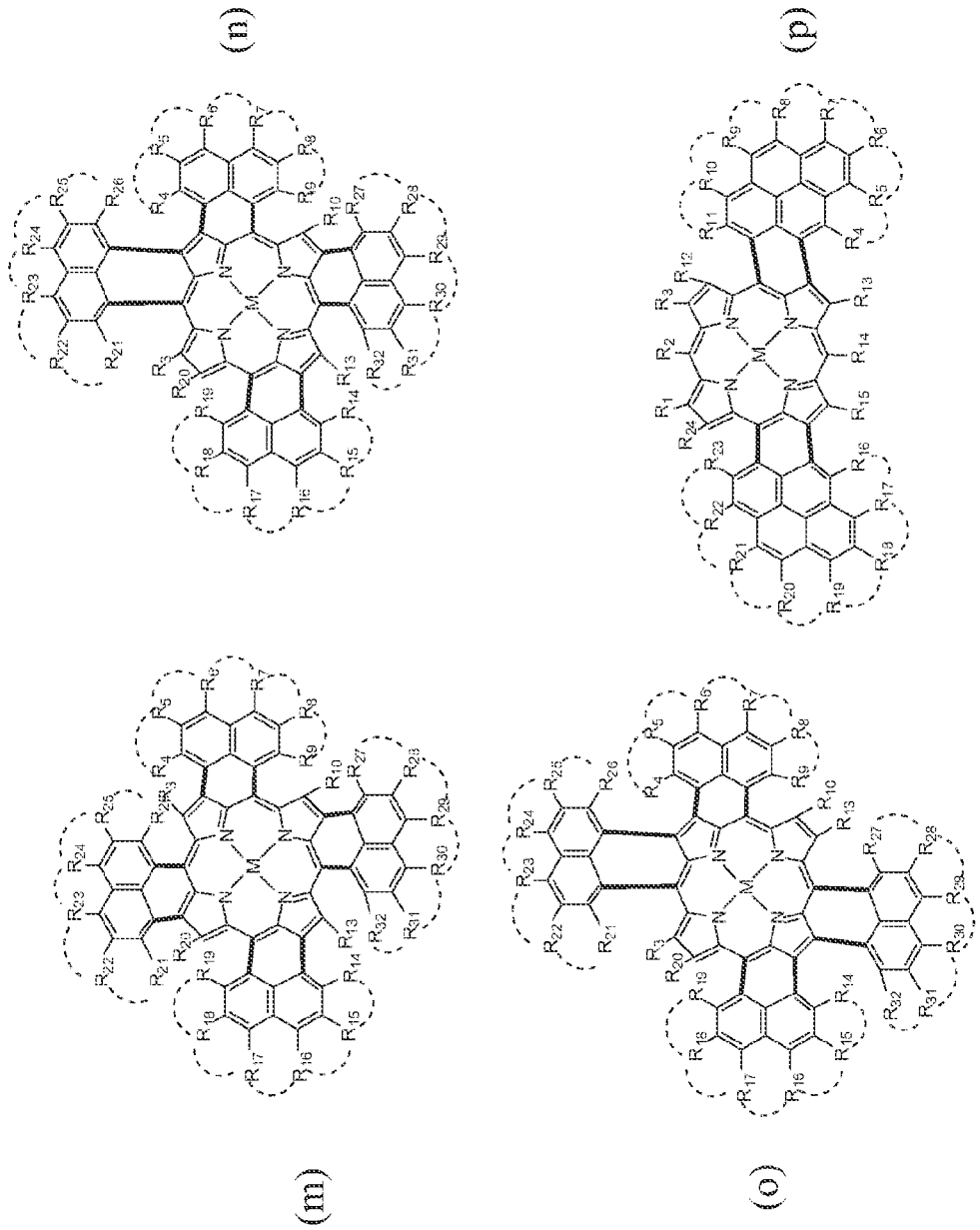
Figure 23:
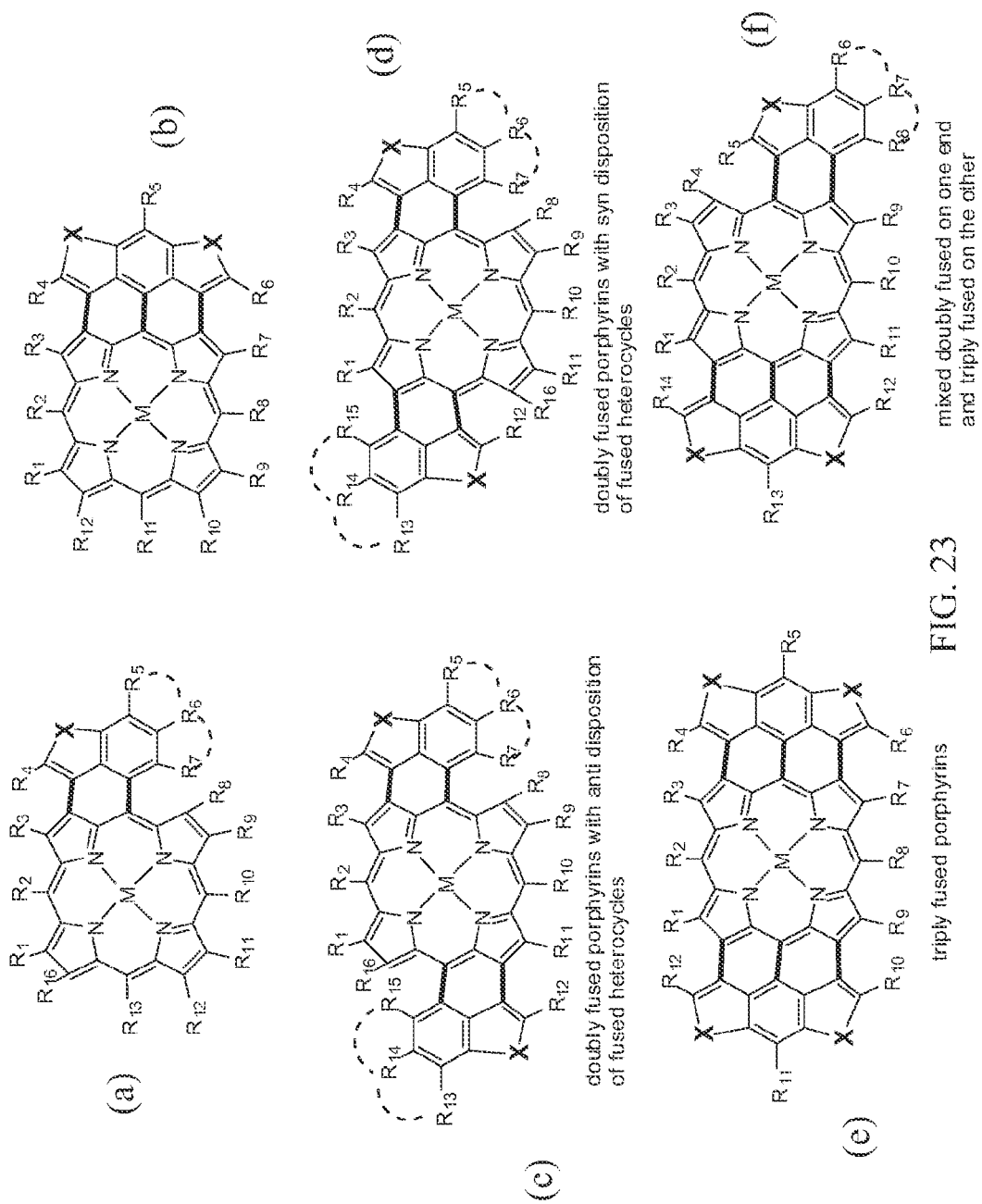
FIGS. 23(a)-(g) show the basic structures of porphyrins fused with polycyclic heterocyclic rings according to another embodiment.
Figure 23:
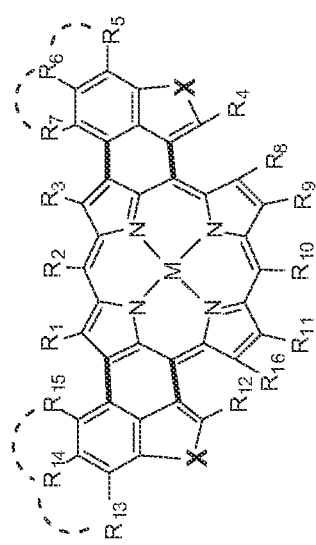

The dotted arcs in the FIGS. 21 and 23 can be all possible combination of fused rings (both aromatic and unsaturated or combination of both aromatic and unsaturated, rings including four, five, six, seven, eight, or nine-membered rings) and all possible combination of fused heterocyclic rings with one or more heteroatoms, including all possible combinations of all heteroatoms in all possible arrangement. Each of the dotted, arc can be the same ring, or different rings (difference by size of rings and composition of rings).

Figure 22:
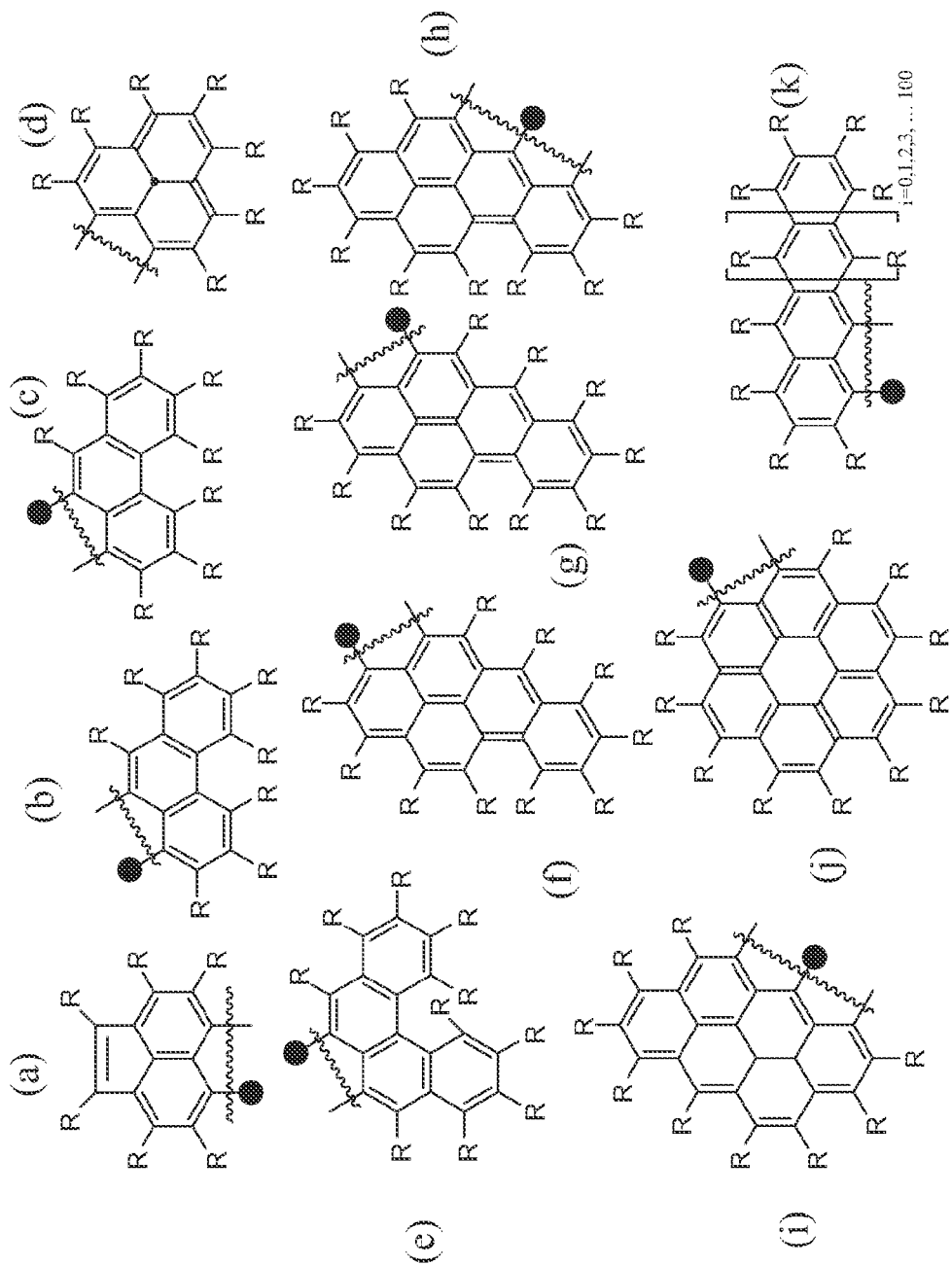
FIGS. 22(a)-22(u) show the basic structures of additional aromatic hydrocarbons that can be fused with porphyrins: acenathphylene (a), phenanthrene (b, c), phenalene (d), coronene (j), acenes (k,l,m), rylenes (m, o, p, q), and pyrene (r).
Figure 22:
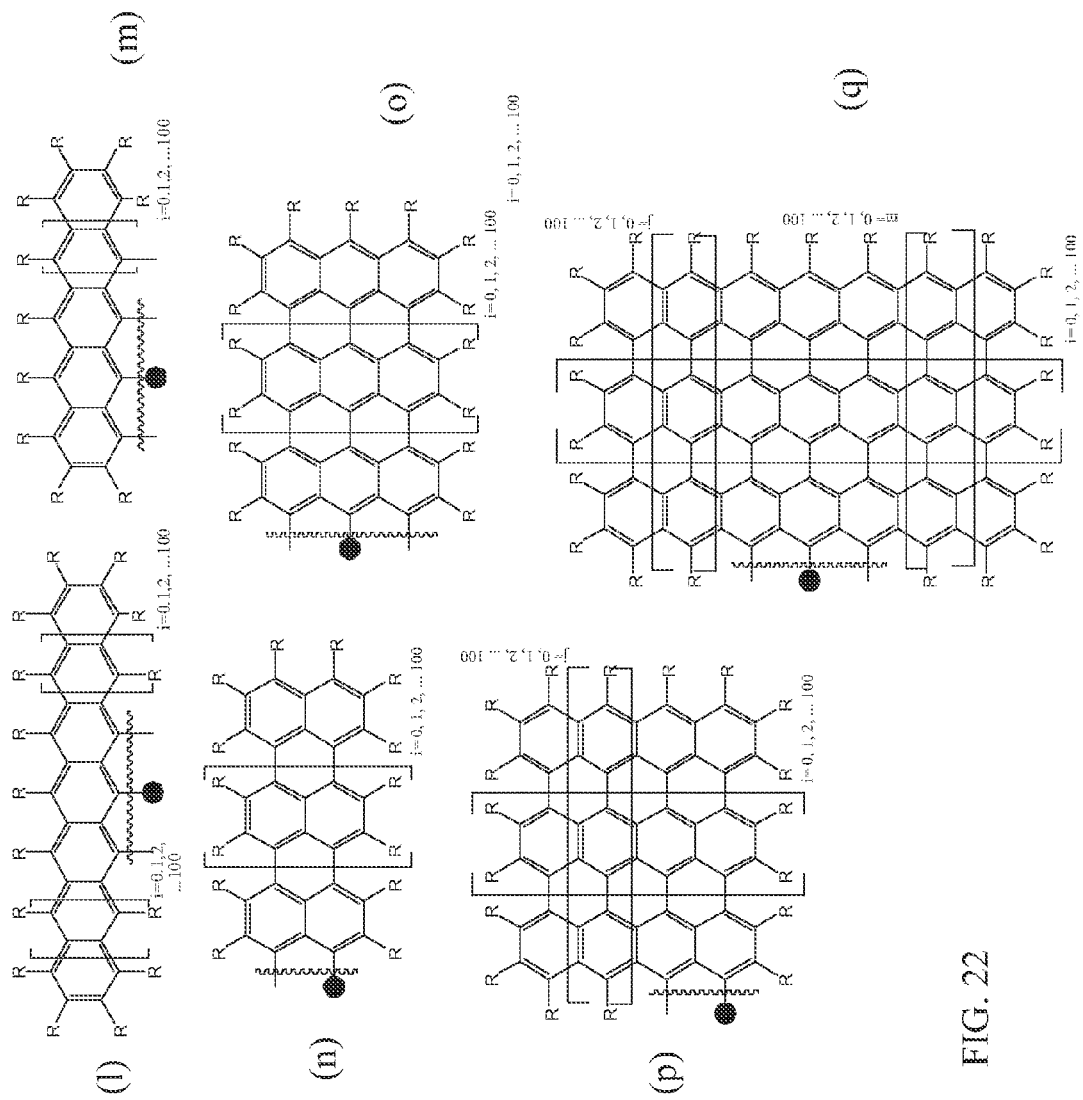
Figure 22:
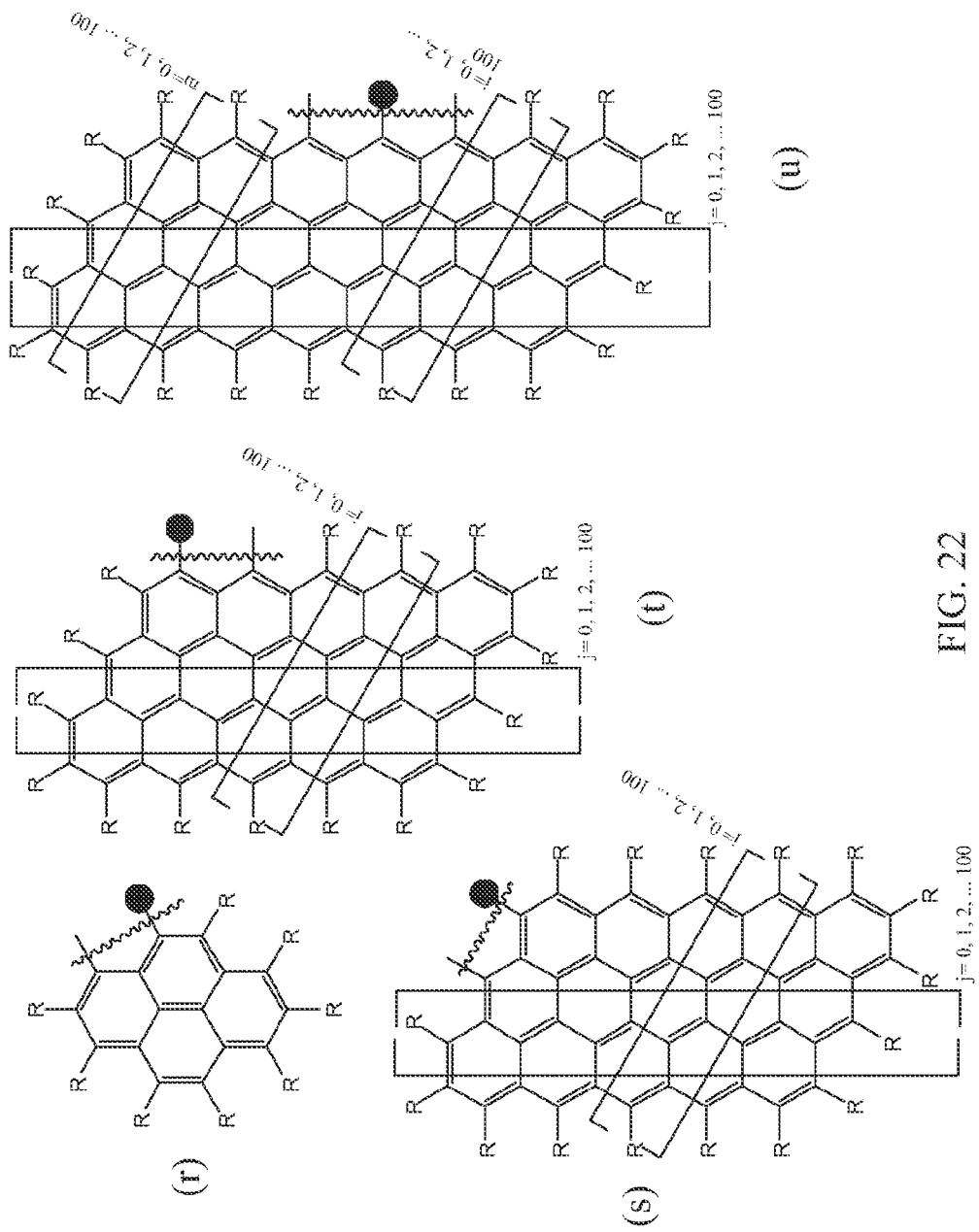
Figure 24:
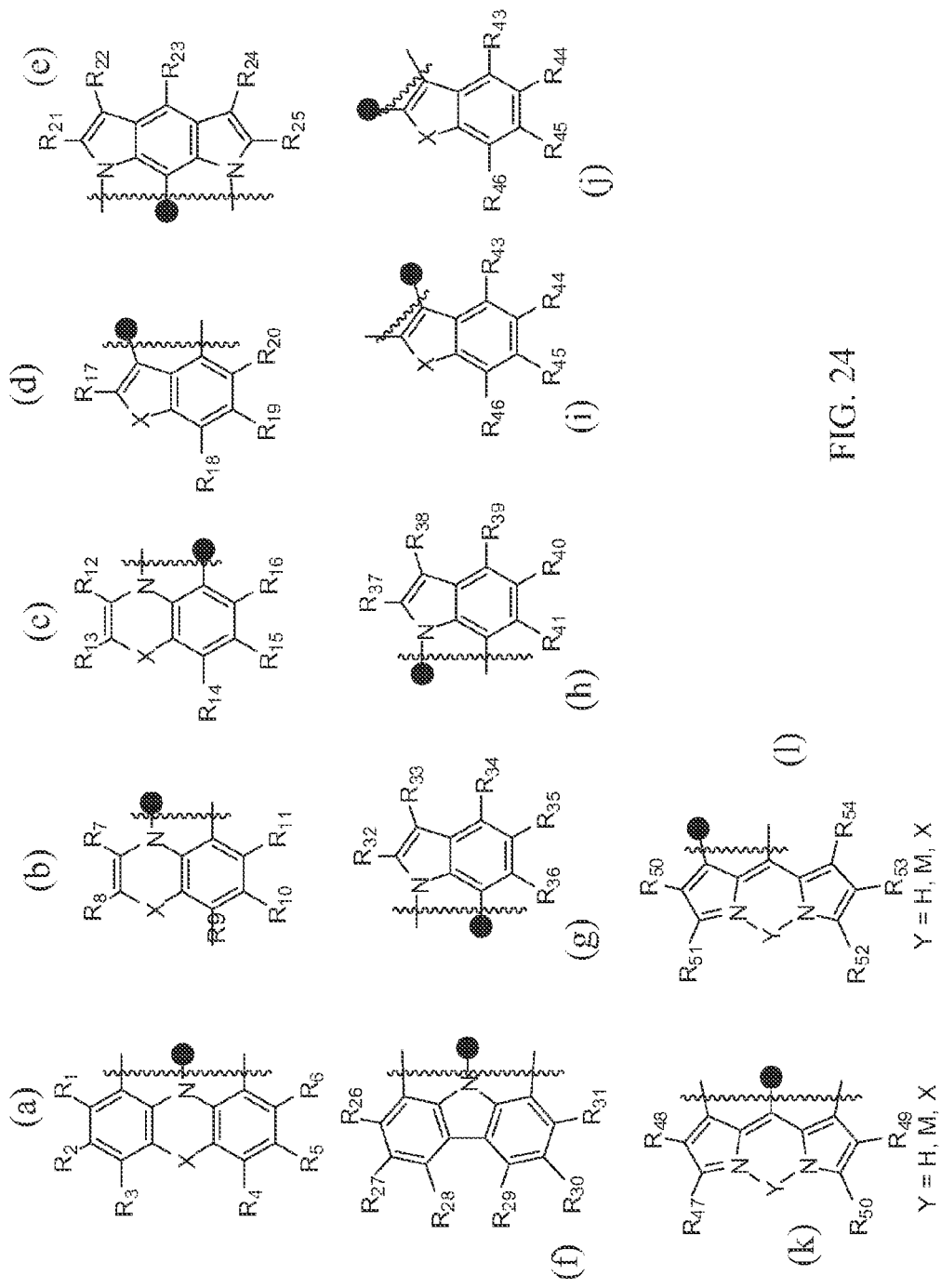
FIGS. 24(a)-(l) show the basic structures of additional heterocyclic rings which can be fused with porphyrins: phenoxazine (a, X=O), phenothiazine (a, X=S), phenoselenazine (a, X=Se), phenotellurazine (a, X=Te), dihydrophenazine (a, X=NH, NR), benzo[b][1,4]oxazine (b,c, X=O), benzo[b][1,4]thiazine (b,c, X=S), benzo[b][1,4]selenazine (b,c, X=Se), benzo[b][1,4]tellurazine (b,c, X=Te), dihydroquinoxaline (b,c, X=NH, NR), benzofurane (d,i,j, X=O), benzothiophene (d,i,j, X=S), benzoselenophene (d,i,j, X=Se), benzotelluraphene (d,i,j, X=Te), indole (d,i,j, X=NH, NR, g,h), carbazole (f), dipyrrin (k,l, Y=BF$_2$, metal).
Figure 25:
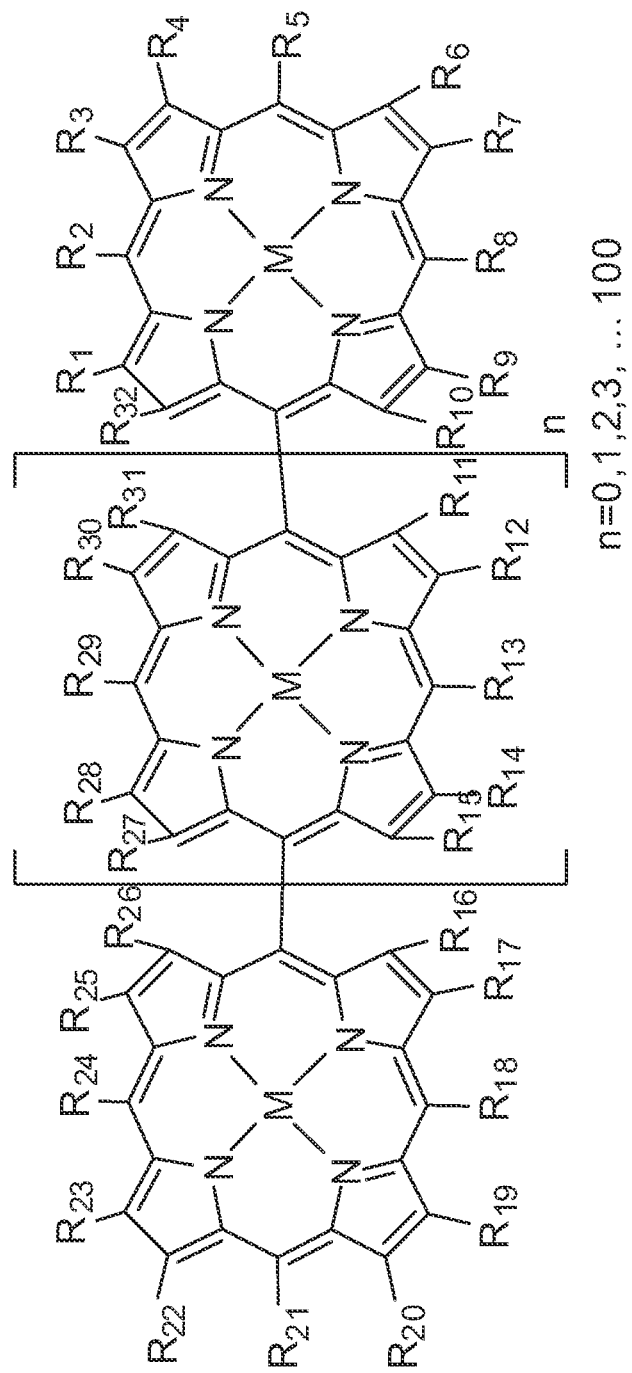
FIG. 25 shows the basic structure of porphyrin olygomers.

Two fused ends of porphyrins can be the same or different. Two fused ends of porphyrins can be naphthalene, anthracene, pyrene and thiophene rings as mentioned above or other polycyclic aromatic rings shown in FIGS. 22 and 24. Specifically, FIGS. 24(a)-(l) show heterocyclic rings. In FIGS. 22 and 24, the fusion position on the polycyclic aromatic rings are marked with a wave-line and the connection with meso position of the porphyrins is marked with a black dot. In FIGS. 22(a)-(u), i, j, and m are each independently 0-100. FIGS. 22(a)-22(u) show the basic structures of additional aromatic hydrocarbons that can be fused with porphyrins: acenathphylene (a), phenanthrene (b, c), phenalene (d), coronene (j), acenes (k,l,m), rylenes (m, o, p, q), pyrene (r).

According to an aspect, of the present disclosure the fused non-activated porphyrins and olygoporphyrins described herein can be incorporated in a donor/acceptor configuration as an optoelectronic material. For example the fused non-activated porphyrins and olygoporphyrins can be paired with acceptor materials to form the donor/acceptor heterojunctions of the photoactive regions in photosensitive devices. Examples of the suitable acceptor materials are $C_{60}$, $C_{70}$, $C_{84}$, $F_{16}$—CuPc, PTCBI, PTCDA, PCBM and PTCDI to name a few.

The donor/acceptor heterojunctions of the photoactive regions utilizing the donor materials of the present disclosure can be formed using any of the known suitable methods. For organic layers, such as the acceptor materials and the donor materials of the present disclosure, preferred methods include vacuum thermal evaporation, ink-jet deposition, such as described in U.S. Pat. Nos. 6,103,982 and 6,087,196, the disclosures of which are incorporated herein by reference in their entireties, organic vapor jet printing (OVJP), such as described in U.S. patent application publication No. 2008/0233287, the disclosure of which is incorporated herein by reference in its entirety. Other suitable deposition methods include solution processing such as spin coating, spray coating, or doctor blading. Solution processes are preferably carried out in nitrogen or other suitable inert atmosphere.

The electrodes such as LiF/Al or BCP/Ag can be deposited by methods known in the art such as vacuum thermal evaporation.

FIG. 27 shows the architecture of an example of a photosensitive device 100 comprising an first electrode 110, a second electrode 130 and a photoactive region 120 disposed between the two electrodes. The first electrode 110 can be an anode typically formed of ITO, the second electrode 130 can be a cathode typically formed from Ag. The photoactive region 120 comprises the donor material based fused non-activated porphyrins as disclosed, herein and an acceptor material.

EXAMPLES

These and other aspects of the present disclosure will be further appreciated upon consideration of the following examples of non-activated porphyrins fused with non-activated polycyclic aromatic rings or heterocyclic rings. These examples are intended to illustrate certain particular embodiments of the invention but are not intended to limit its scope, as defined by the claims.

Example 1

ZnMFBPP and ZnDFBPP

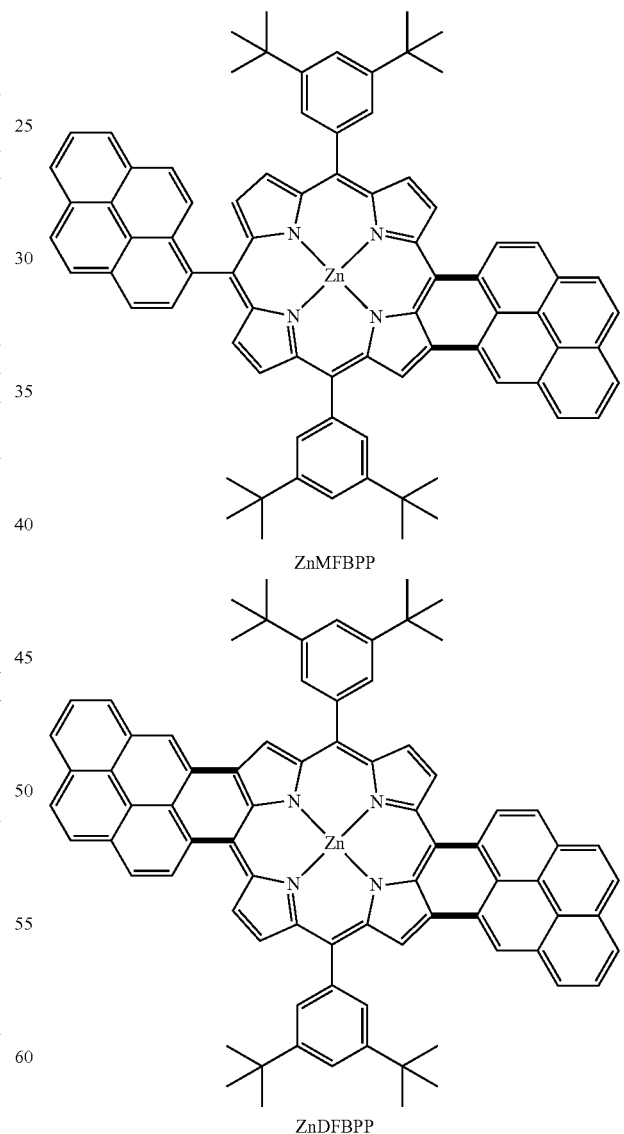

ZnMFBPP

ZnDFBPP 4,4,5,5-tetramethyl-2-(pyren-1-yl)-1,3,2-dioxaborolane. To a approx. 0.1 M solution of 1-bromopyrene in toluene 10 mol % of $Cl_2Pd(PPh_3)_2$, 5 equivalents of picolineborane and 10 equivalents of triethylamine was added. The reaction mixture was degassed with nitrogen and refluxed overnight. The reaction mixture was then quenched with water, toluene was distilled, off and the residue was subjected to column chromatography on silica gel (gradient elution with hexanes-ethyl acetate mixtures from 1:0 to 1000:5) to give 70-80% of 4,4,5,5-tetramethyl-2-(pyren-1-yl)-1,3,2-dioxaborolane.

$^1$H-NMR (CDCl$_3$, 400 MHz): 1.51 (s, 12H), 8.02 (t, 1H, J=7.7 Hz), 8.07-8.24 (m, 6H), 8.56 (d, 1H, J=9.7 Hz), 9.09 (d, 1H, J=9.7 Hz).

MALDI TOF mass spectrometry: 328 (M$^+$), requires 328.16 for C$_{22}$H$_{21}$BO$_2$.

$^{13}$C-NMR (CDCl$_3$, 75 MHz): 31.7, 35.0, 118.9, 120.8, 122.7, 122.8, 124.1, 124.7, 125.2, 125.5, 126.2, 127.4, 127.5, 127.7, 127.9, 129.6, 129.8, 129.9, 130.8, 131.3, 131.8, 132.0, 132.5, 132.6, 132.64, 133.4, 133.5, 137.9, 141.6, 148.6, 150.7, 151.0. UV/VIS (CH$_2$Cl$_2$) λ, nm, (ε): 235 (84899), 243 (120670), 264 (48136), 275 (69032), 308 (34871), 323 (47186), 337 (54350), 427 (432531), 517 (6415), 551 (24905), 590 (5614).

HRMS: 1149.4834 (M$^+$ and MH$^+$), calcd. 1149.4808 for C$_{80}$H$_{69}$N$_4$Zn. MALDI TOF: 1150 (M$^+$ and MH$^+$), requires 1149.48 for C$_{80}$H$_{69}$N$_4$Zn. Elemental analysis for C$_{80}$H$_{68}$N$_4$Zn*MeOH: calcd: C, 82.25; H, 6.14; N, 4.74; found: C, 82.45; H, 6.25; N, 4.65.

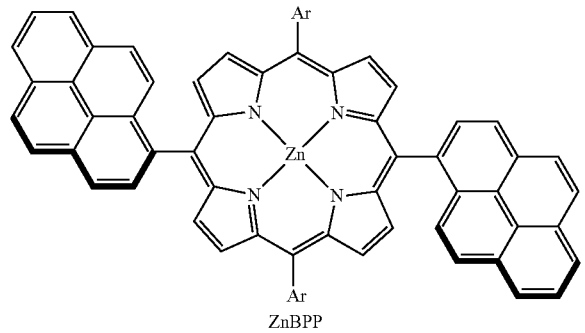

ZnBPP

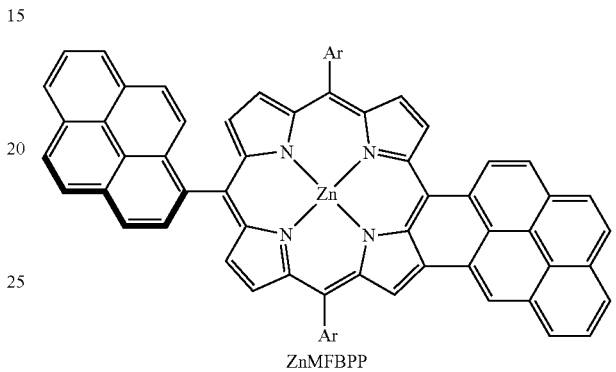

ZnMFBPP

[10,20-Bis(3,5-di-tert-butylphenyl)-5,15-bis-(1-pyrenyl)porphyrinato(2-)-κN$^{21}$,κN$^{22}$,κN$^{23}$,κN$^{24}$]zinc(II) (See FIG. 1, ZnBPP). (A). NBS (5 g, 28 mmol, 2.1 equiv.) was added to a stirred solution of [5,15-Bis(3,5-di-tert-butylphenyl)porphyrinato(2-)-κN$^{21}$,κN$^{22}$,κN$^{23}$,κN$^{24}$]zinc(II) (10 g, 13.33 mmol) in dichloromethane (700 ml) and pyridine (20 ml) at −10° C. (NaCl/ice bath) under nitrogen atmosphere. The reaction mixture was stirred, at the same temperature for 10 minutes, then was allowed to warm to 0° C. in a wafer bath for 5 minutes and was quenched with acetone (20 ml). The crude reaction mixture was passed, through silica gel column, eluting with dichloromethane-pyridine mixture (100:1). All green-purple fractions were collected, solvents were evaporated, the residue was dissolved in dichloromethane-pyridine mixture (95:5, 100 ml) and 200 ml of methanol was added to precipitate bromoporphyrin. All crystals were collected by filtration after 30 minutes to give [10,20-Bis(3,5-di-tert-butylphenyl)-5,15-bis-bromo-porphyrinato(2-)-κN$^{21}$,κN$^{22}$,κN$^{23}$,κN$^{24}$]zinc(II) (7.5 g, 8.26 mmol, 62%).

(B). A mixture of the above dibromoporphyrin (6.33 g, approx. 6.97 mmol), cesium carbonate (23.5 g, 70 mmol, 10 equiv.), Pd(PPh$_3$)$_4$ (800 mg, 10 mol %) and 1-pyrenyl-tetramethyldioxaborolane (5.26 g, 16.03 mmol, 2.3 equiv.) in toluene (800 ml) and pyridine (10 ml) was degassed and refluxed in nitrogen atmosphere for 12 hours. The reaction mixture was cooled and passed consecutively through a pad of celite, silica gel and neutral alumina washing with toluene. Toluene was then distilled off in vacuum and the residue was separated by crystallization from dichloromethane-methanol to afford [10,20-Bis(3,5-di-tert-butylphenyl)-5,15-Bis(1-pyrenyl)porphyrinato(2-)-κN$^{21}$,κN$^{22}$,κN$^{23}$,κN$_{24}$)]zinc(II) (See FIG. 1, ZnBPP, 6 g, 5.2 mmol, 75%).

$^1$H-NMR (CDCl$_3$, 400 MHz): 1.47, 1.477 and 1.481 (s, 36H, atropoisomers), 7.50 (dd, 2H, J=9.3, 10.6 Hz), 7.71-7.74 (m, 4H, atropoisomers), 8.04-8.14 (m, 8H), 8.33 (t, 4H, J=7.2 Hz), 8.42 (d, 2H, J=9.1 Hz), 8.54 (d, 2H, J=7.7 Hz), 8.63 (dd, 4H, J=0.8, 4.7 Hz), 8.86 (dd, 2H, J=2.8, 7.7 Hz), 8.92 (d, 4H, 4.7 Hz).

[10,20-Bis(3,5-di-tert-butylphenyl)-4,5-(1,10-pyrenyl)-15-(1-pyrenyl)porphyrinato(2-)-κN$^{21}$,κN$^{22}$,κN$^{23}$,κN$^{24}$]zinc(II) (See FIG. 1, ZnMFBPP) and [10,20-Bis(3,5-di-tert-butylphenyl)-4,5,14,15-bis-(1,10-pyrenyl)-porphyrinato(2-)-κN$^{21}$,κN$^{22}$,κN$^{23}$,κN$^{24}$]zinc(II) (See FIG. 1, ZnDFBPP). The above bis-pyrenyl-porphyrin ZnBPP*MeOH (550 mg, 0,465 mmol) in a glass tube under nitrogen flow was placed into an oven preheated to 530° C. The oven temperature rose to 530° C. in 1-2 minutes and after additional approx. 1 minute, starting material melted. Heating continued, for 20-30 sec. until the reaction mixture turned into brown color and the first bubbles appeared. The glass tube was cooled to room temperature under nitrogen. Prolonged heating causes reduced yield of the final product ZnDFBPP and mono-fused product completely converted to ZnDFBPP. The crude mixture was dissolved, in dichloromethane (500 ml) with addition of pyridine (5 ml) and passed through a filter filled with silica gel washing with dichloromethane. All purple fractions were collected, solvents evaporated. The residue was redissolved in dichloromethane and passed, through a filter filled with alumina, eluting with dichloromethane to get crude mono-fused product (ZnMFBPP) and with hexanes-dichloromethane-pyridine 700-300-5 mixture to get crude doubly-fused product (ZnDFBPP). The products were subsequently recrystallized from dichloromethane by layered addition of methanol. Yields: ZnMFBPP (50 mg, 9%), ZnDFBPP (190 mg, 36%). [10,20-Bis(3,5-di-tert-butylphenyl)-4,5-(1,10-pyrenyl)-15-(1-pyrenyl)porphyrinato(2-)-κN$^{21}$,κN$^{22}$,κN$^{23}$,κN$^{24}$]zinc(II) (See FIG. 1, ZnMFBPP).

$^1$H-NMR (5%-pyridine-d5 in C$_6$D$_6$, 500 MHz): 1.49, 1.507, 1510 and 1.52 (s, 36H, atropoisomers), 7.39 (d, 1H, J==9.5 Hz), 7.59 (d, 1H, J=9.5 Hz), 7.78-7.85 (m, 3H), 7.94-7.96 (m, 2H), 8.01 (s, 1H), 8.02-8.09 (m, 5H), 8.14 (d, 1H, J=9.5 Hz), 8.24 (d, 1H, J=8 Hz), 8.32 (d, 1H, J=8 Hz), 8.39 (t, 1H, J=1.5 Hz), 8.45 (t, 1H, J=1.5 Hz), 8.53 (d, 1H, J=1.5 Hz), 8.55 (d, 1H, J=4.5 Hz), 8.56 (t, 1H, J=1.5 Hz), 8.63 (d, 1H, J=4.5 Hz), 8.84 (d, U, J=8 Hz), 9.03 (d, 1H, J=4.5 Hz), 9.09 (d, 1H, J=4.5 Hz), 9.13 (s, 1H), 9.22 (d, 1H, J=4.5 Hz), 9.48 (d, 1H, J=8.5 Hz), 9.53 (d, 1H, J=4.5 Hz), 9.98 (s, 1H).

$^{13}$C-NMR (5%-pyridine-d5 in C$_6$D$_6$, 500 MHz, 93.7 MHz): 30.2, 31.85, 31.86, 31.89, 35.18, 35.20, 114.3, 119.0, 121.00, 121.03, 124.3, 124.6, 124.8, 124.9, 125.0, 125.3, 125.4, 125.7, 125.8, 126.3, 126.4, 126.8, 127.4, 127.7, 129.1, 130.7, 130.86, 130.90, 131.0, 131.2, 131.4, 131.6, 131.8, 131.9, 132.2, 132.3, 132.5, 132.69, 132.75, 132.8, 132.9, 133.0, 133.8, 133.9, 137.4, 138.0, 139.0, 143.4, 143.5, 146.8, 149.08, 149.10, 149.23, 149.26, 150.3, 150.5, 150.6, 151.0, 151.8, 152.0, 152.3.

UV/VIS (CH$_2$Cl$_2$) λ, nm, (ε): 706 (43480), 495 (206480), 386 (40296), 339 (45680), 324 (38374), 275 (51790), 264 (44275).

Emission: $\lambda_{max}$, 722 nm; quantum yield, 8%. HRMS: 1146.4581 (M$^+$), calcd. 1146.4573 for C$_{80}$H$_{66}$N$_4$Zn. Elemental analysis for C$_{80}$H$_{66}$N$_4$Zn*MeOH: calcd.: C, 82.39; H, 5.97; N, 4.74; found: C, 82.69; H, 5.91; N, 4.86.

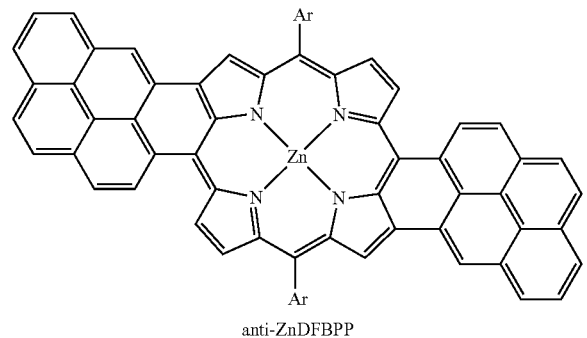

anti-ZnDFBPP

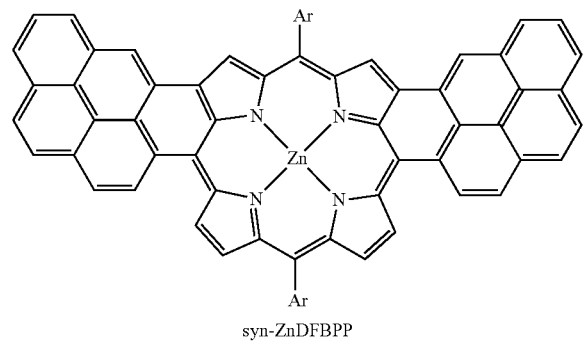

syn-ZnDFBPP

[10,20-Bis(3,5-di-tert-butylphenyl)-4,5,14,15-bis-(1,10-pyrenyl)-porphyrinato(2-)-κN$^{21}$,κN$^{22}$,κN$^{23}$,κN$^{24}$)zinc(II) (See FIG. 1, ZnDFBPP).

$^1$H-NMR (5%-pyridine-d$_5$ in C$_6$D$_6$, 25° C., 500 MHz, two regioisomers): 1.53, 1.59 and 1.61 (s, 36H, regioisomers), 7.81 and 7.82 (d, 2H, J=8 Hz, regioisomers), 7.91-8.03 (m, 8H), 8.1 and 8.17 (t, 2H, J=8.5 Hz, regioisomers), 8.26 and 8.28 (d, 2H, J=8.5 Hz, regioisomers), 8.40, 8.55 and 8.62 (d, 4H, J=1.5 Hz, regioisomers), 9.00 and 9.08 (d, 2H, J=4.5 Hz, regioisomers), 9.07 and 9.12 (s, 2H, regioisomers), 9.28 and 9.36 (d, 2H, J=4.5 Hz, regioisomers), 9.33 and 9.35 (d, 2H, J=8 Hz, regioisomers), 9.78 and 9.84 (s, 2H, regioisomers).

$^1$H-NMR (5%-pyridine-d$_5$ in C$_6$D$_6$, 75° C., 500 MHz, two regioisomers): 1.51, 1.57 and 1.60 (s, 36H regioisomers), 7.08 (t, 2H, J=8 Hz), 7.92 (t, 2H, J=9 Hz), 7.99 (d, 4H, J=8 Hz), 8.04 (s, 2H), 8.06 and 8.15 (d, 2H, regioisomers), 8.02-8.06 (m, 4H), 8.45 and 8.54 (d, 2H, J=1 Hz, regioisomers), 8.90 and 8.93 (d, 2H, J=4.5 Hz, regioisomers), 9.11 and 9.13 (s, 2H, regioisomers), 9.23-9.30 (m, 4H), 9.67 and 9.70 (s, 2H, regioisomers).

$^{13}$C-NMR (5%-pyridine-d$_5$ in C$_6$D$_6$, 25° C., 125 MHz, two regioisomers): 30.1, 31.84, 31.92, 31.94, 35.20, 114.0, 114.2, 121.1, 121.3, 121.4, 122.7, 124.1, 124.2, 124.8, 125.4, 125.41, 125.8, 126.4, 126.9, 127.4, 127.42, 127.5, 128.9, 129.0, 130.3, 130.5, 130.7, 130.8, 131.8, 132.0, 132.9, 133.0, 133.03, 133.3, 133.4, 133.6, 136.5, 136.6, 138.0, 138.4, 143.3, 143.4, 146.7, 147.4, 149.2, 150.1, 150.4, 150.5, 150.8, 151.1.

UV/VIS (CH$_2$Cl$_2$) λ, nm, (ε): 815 (101541), 735 (27675), 651 (9565), 526 (141945), 505 (138669).

Emission (CH$_2$Cl$_2$): $\lambda_{max}$, 815 nm; quantum yield, 10%.

MALDI TOP: 1143.9 (M$^+$), requires 1144.44 for C$_{80}$H$_{64}$N$_4$Zn. HRMS: 1144.4418 (M$^+$), calcd. 1144.4417 for C$_{80}$H$_{64}$N$_4$Zn.

Elemental analysis for C$_{80}$H$_{64}$N$_4$Zn*MeOH: calcd.: C, 82.53; H, 5.81; N, 4.75; found: C, 82.92; H, 5.77; N, 4.78.

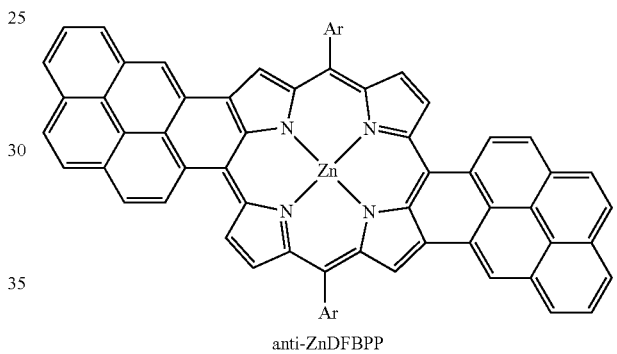

anti-ZnDFBPP

[10,20-Bis(3,5-di-tert-butylphenyl)-5,7,15,17-bis-(1,10-pyrenyl)-porphyrinato(2-)-κN$^{21}$,κN$^{22}$,κN$^{23}$,κN$^{24}$)zinc(II) compound anti-ZnDFBPP. anti-ZnDFBPP can be obtained by separation of a mixture of anti/syn ZnDFBPP using silica gel column (gradient elution with benzene:hexanes—1:5 to 2:3) by collecting first fraction followed by layered crystallization from dichloromethane:methanol mixture. R$_f$=0.42 (hexanes:benzene=1:1).

$^1$H-NMR (5%-pyridine-d$_5$ in C$_6$D$_6$, 25° C., 500 MHz): 1.59 (s, 36H, t-Bu), 7.83 (t, 2H, J=8 Hz, H$_{pyrene}$), 7.93 (d, 2H, J=9 Hz, H$_{pyrene}$), 7.99 (d, 2H, J=9 Hz, H$_{pyren}$), 8.00 (d, 2H, J H Hz, H$_{pyrene}$), 8.05 (d, 2H, J=8 Hz, H$_{pyrene}$), 8.04 (t, 2H, J=1.5 Hz, p-H of Ar), 8.27 (d, 2H, J-9 Hz, H$_{pyrene}$), 8.50-8.51 (m, 2H, o-H of Ar), 8.55 (d, 2H, J=1.5 Hz, o-H of Ar), 9.00 (d, 2H, J=4.5 Hz, β-pyrrolic H$_{porph}$), 9.13 (s, 2H, β-pyrrolic H$_{porph}$), 9.27 (d, 2H, J=4.5 Hz, β-pyrrolic H$_{porph}$), 9.33 (d, 2H, J=8 Hz, H$_{pyrene}$), 9.84 (s, 2H, H$_{pyrene}$).

$^{13}$C-NMR (5%-pyridine-d$_5$ in C$_6$D$_6$, 125 MHz): 32.0, 35.3, 114.3, 121.3, 122.9, 124.4, 124.5, 125.4, 125.9, 126.4, 126.75, 126.81, 127.4, 129.2, 130.5, 130.8, 131.8, 132.0, 133.0, 133.3, 133.5, 136.7, 138.1, 143.4, 146.8, 149.5, 150.2, 150.4, 151.2.

UV/VIS (CH$_2$Cl$_2$) λ, nm, (ε): 815 (81206), 741 (20628), 656 (5045), 559 (54452), 504 (151197). Emission (CH$_2$Cl$_2$): $\lambda_{max}$, 839 nm; quantum yield, 7.7%.

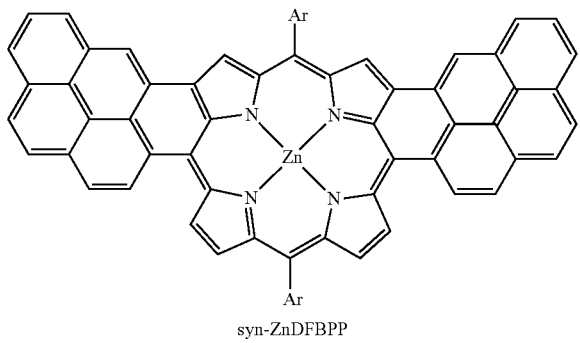

syn-ZnDFBPP

[10,20-Bis(3,5-di-tert-butylphenyl)-3,5,15,17-bis-(1,10-pyrenyl)-porphyrinato(2-)-$\kappa N^{21},\kappa N^{22},\kappa N^{23},\kappa N^{24}$)zinc(II) compound syn-ZnDFBPP. syn-ZnDFBPP can be obtained by separation of a mixture of anti/syn ZnDFBPP using silica gel column (gradient elution with benzene:hexanes—1:5 to 2:3) by collecting the last fractions followed by layered crystallization from dichloromethane-methanol mixture. $R_f$=0.31 (hexanes:benzene=1:1).

$^1$H-NMR (5%-pyridine-$d_5$ in $C_6D_6$, 25° C., 500 MHz): 1.53 (s, 18H, t-Bu), 1.61 (s, 18H, t-Bu), 7.82 (t, 2H, J=8 Hz, $H_{pyrene}$), 7.93 (d, 2H, J=9 Hz, $H_{pyrene}$), 7.99 (d, 2H, J=9 Hz, $H_{pyrene}$), 8.00 (t, 1H, J=1.5 Hz, p-H of Ar), 8.00 (d, 2H, J=8 Hz, $H_{pyrene}$), 8.05 (d, 2H, J=8 Hz, $H_{pyrene}$), 8.17 (t, 1H, J=1.5 Hz, p-H of Ar), 8.27 (d, 2H, J=9 Hz, $H_{pyrene}$), 8.40 (2, 2H, J=1.5 Hz, o-H of Ar), 8.61 (d, 2H, J=1.5 Hz, o-H of Ar), 9.07 (d, 2H, J=4.5 Hz, β-pyrrolic $H_{porph}$), 9.08 (s, 2H, β-pyrrolic $H_{porph}$), 9.36 (d, 2H, J=4.5 Hz, β-pyrrolic $H_{porph}$), 9.37 (d, 2H, J=8 Hz, $H_{pyrene}$), 9.78 (s, 2H, $H_{pyrene}$).

$^{13}$C-NMR (5%-pyridine-$d_5$ in $C_6D_6$, 125 MHz): 30.2, 31.9, 32.0, 114.0, 121.1, 121.4, 122.52, 122.54, 123.3, 123.34, 124.3, 125.0, 125.5, 125.9, 126.3, 126.8, 127.4, 127.5, 128.6, 128.7, 128.8, 129.0, 129.7, 129.85, 129.9, 130.5, 130.80, 130.85, 131.8, 131.9, 132.9, 133.0, 133.7, 136.6, 138.5, 143.3, 143.5, 147.4, 149.2, 149.5, 150.6, 150.8.

UV/VIS ($CH_2Cl_2$) λ, nm, (ε): 811 (91461), 736 (26446), 657 (10865), 527 (145812). Emission ($CH_2Cl_2$): $\lambda_{max}$, 829 nm; quantum yield, 12.8%.

Example 2

ZnQFTPP

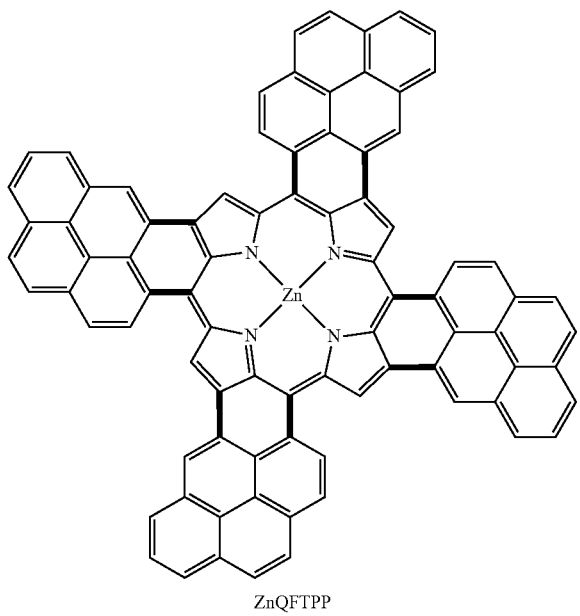

ZnQFTPP 5,15-bis-(1-pyrenyl)porphyrinato(2-)-$\kappa N^{21},\kappa N^{22},\kappa N^{23}$, $\kappa N^{24}$)zinc(II). To a stirred solution of 1-pyrenecarboxaldehyde (3.7 g, 15.92 mmol) and 1,1'-dipyrrolomethane (2.34 g, 15.92 mmol) in dichloromethane (2 L) under nitrogen atmosphere trifluoroacetic acid was added (2 ml) and the reaction mixture was stirred at ambient temperature in dark for 24 hours. After that DDQ (5.36 g) was added and stirring continued for additional 1 hour. The reaction mixture was quenched with triethylamine (10 ml) and passed through filter filled with silica gel washing with dichloromethane. All purple fractions were collected, dichloromethane evaporated and the residue passed through filter filled with alumina washing with dichloromethane. All purple fractions were collected, dichloromethane was evaporated to volume 500 ml. To this solution of the free-base bis-pyrenyl-porphyrin 30 ml of saturated solution of zinc(II) acetate was added and the resulting mixture was stirred for 3 hours at ambient temperature. The reaction mixture was washed with water and dichloromethane solution was passed through filter filled with silica gel washing with dichloromethane. The residue after evaporation of solvent was crystallized from dichloromethane-methanol mixture to give 5,15-bis-(1-pyrenyl)porphyrinato (2-)-$\kappa N^{21},\kappa N^{22},\kappa N^{23},\kappa N^{24}$)zinc(II) (430 mg, 0.56 mmol, 7%).

10,20-bis-bromo-5,15-bis-(1-pyrenyl)porphyrinato(2-)-$\kappa N^{21},\kappa N^{22},\kappa N^{23},\kappa N^{24}$)zinc(II). NBS (194 mg, 1.09 mmol, 2.1 equiv.) was added to a stirred solution of the above 5,15-bis-(1-pyrenyl)porphyrinato(2-)-$\kappa N^{21},\kappa N^{22},\kappa N^{23},\kappa N^{24}$)zinc (II) (402 mg, 0.519 mmol) in dichloromethane (300 ml) and pyridine (5 ml) at −10° C. (NaCl/ice bath) under nitrogen atmosphere. The reaction mixture was stirred at the same temperature for 10 minutes the was allowed to warm to 0° C. in a water bath for 5 minutes and was quenched with acetone (20 ml). The crude reaction mixture was passed through silica gel column, eluting with dichloromethane-pyridine mixture (100:1). All green-purple fractions were collected, solvents were evaporated, the residue was dissolved in dichloromethane-pyridine mixture (95:5, 100 ml) and 200 ml of methanol was added to precipitate brominated porphyrin. All crystals were collected by filtration after 30 min to give 10,20-bis-bromo-5,15-bis-(1-pyrenyl)porphyrinato(2-)-$\kappa N^{21}$, $\kappa N^{22},\kappa N^{23},\kappa N^{24}$)zinc(II) (435 mg, 0.47 mmol, 90%).

$^1$H-NMR (5% pyridine-d5 in $CDCl_3$, 500 MHz): 6.93 (t, 2H, J=8 Hz), 7.19 (d, 2H, J=10 Hz), 7.61 (d, 2H, J=10 Hz), 8.06-8.09 (m, 4H), 8.32-8.36 (m, 4H), 8.42 (d, 2H, J=8 Hz), 8.52 (d, 4H, J=4.5 Hz), 8.79 (d, 2H, J=8 Hz), 9.55 (d, 4H, J=4.5 Hz).

5,10,15,20-tetrakis-(1-pyrenyl)porphyrinato(2-)-$\kappa N^{21}$, $\kappa N^{22},\kappa N^{23},\kappa N^{24}$)zinc(II) ZnTPP. A mixture of the above 10,20-bis-bromo-5,15-bis-(1-pyrenyl)porphyrinato(2-)-$\kappa N^{21},\kappa N^{22},\kappa N^{23},\kappa N^{24}$)zinc(II) (400 mg, 0.429 mmol), cesium carbonate (1.45 g, 10 equiv.), Pd(PPh$_3$)$_4$ (50 mg, 10 mol %) water (0.5 ml) and 1-pyrenylboronic acid (232 mg, 0.95 mmol, 2.2 equiv.) in toluene (150 ml) and pyridine (2 ml) was degassed and reflux in nitrogen atmosphere for 12 hours. The reaction mixture was cooled and passed consecutively through pad of celite, silica gel and neutral alumina washing with toluene. Toluene was distilled off in vacuum, the residue was separated by crystallization from dichloromethane-methanol to afford 5,10,15,20-tetrakis-(1-pyrenyl)porphyrinato(2-)-$\kappa N^{21},\kappa N^{22},\kappa N^{23},\kappa N^{24}$)zinc(II) (260 mg, 0.221 mmol, 52%).

$^1$H-NMR (5% pyridine-d5 in $CDCl_3$, 500 MHz, mixture of atropoisomers): 7.46-7.66 (m, 8H), 7.98-8.07 (m, 8H), 8.13-8.19 (m, 4H), 8.23-8.33 (m, 8H), 8.44-8.48 (m, 8H), 8.76-8.87 (m, 4H). MALDI TOF: 1172.6 (M$^+$), requires 1172.29 for $C_{84}H_{44}N_4Zn$.

4,5,9,10,14,15,19,20-tetrakis-(1,10-pyrenyl)porphyrinato(2-)-κN$^2$),κN$^{22}$,κN$^{23}$,κN$^{24}$)zinc(II) ZnQFTPP. The above tetrakis-pyrenyl-porphyrin ZnTPP*MeOH (48 mg, 0.0399 mmol) in a glass tube under nitrogen flow was placed into oven preheated to 530° C. The oven temperature rose to 530° C. in 1-2 minutes and after additional approx. 1 minute starting material melted. Heating continued for approx. 2 minutes until reaction mixture turned into dark color and the first bubbles appeared. The tube was cooled to room temperature under nitrogen. The crude mixture was dissolved in dichloromethane (500 ml) with addition of pyridine (5 ml) and passed through filter filled with silica gel washing with dichloromethane and then pyridine to wash ZnQFTPP. Yield: 22 mg, 49%.

$^1$H-NMR (dilute solution in 5%-pyridine-d$_5$ in C$_6$D$_6$, 75° C., 600 MHz, signal assignment for possible regioisomers could not be done, longer acquisition time required, signal broadening due to aggregation): 7.63 (d, 4H, J=8 Hz), 7.74-7.84 (m, 12H), 7.88-7.97 (m, 16H), 8.03 (d, 4H, J=9 Hz).

UV/VIS (5% pyridine in CH$_2$Cl$_2$) λ, nm (ε): 1003 (13954), 873 (43861), 813 (30458), 620 (73072), 576 (70842).

MALDI-TOF MS (without matrix): 1164.32 (M$^+$), requires 1164.22 for C$_{84}$H$_{36}$N$_4$Zn. Peak of the molecular ion could not be obtained by using HRMS (ESI/APCI).

$^{13}$H-NMR (5% pyridine-d$_5$ in C$_6$D$_6$, 125 MHz, weak signals): 124.0, 125.07, 125.10, 125.17, 126.10, 126.15, 126.8, 127.4, 127.5, 128.9, 129.6, 129.9, 131.6.

Example 3

ZnFBTP

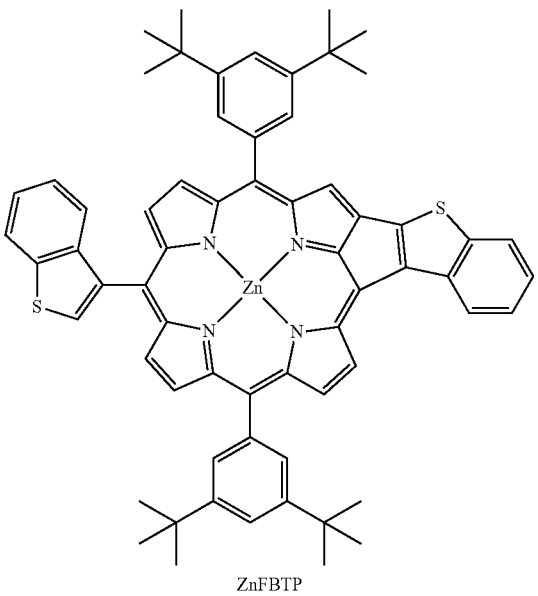

ZnFBTP

[10,20-Bis(3,5-di-tert-butylphenyl)-5,15-bis(3-benzothienyl)porphyrinato(2-)-κN$^{21}$,κN$^{22}$,κN$^{23}$,κN$^{24}$)zinc(II) ZnBTP. A mixture of the above [10,20-Bis(3,5-di-tert-butylphenyl)-5,15-bis-bromo-porphyrinato(2-)-κN$^{21}$,κN$^{22}$, κN$^{23}$,κN$^{24}$)zinc(II) (3.4 g, 3.74 mmol), cesium carbonate (10 g, 70 mmol, 8 equiv.), Pd(PPh$_3$)$_4$ (440 mg, 10 mol %) water (3 ml) and 3-benzothienylboronic acid (1.67 g, 9.38 mmol, 2.5 equiv.) in toluene (600 ml) and pyridine (6 ml) was degassed, and reflux in nitrogen atmosphere for 12 hours. The reaction mixture was cooled and passed consecutively through pad of celite, silica gel and neutral alumina washing with toluene. Toluene was distilled off in vacuum, the residue was separated by crystallization from dichloromethane-methanol to afford [10,20-Bis(3,5-di-tert-butylphenyl)-5,15-bis(3-benzothienyl)porphyrinato(2-)-κN$^{21}$,κN$^{22}$,κN$^{23}$,κN$^{24}$)zinc(II) ZnBTP (3.03 g, 2.99 mmol, 80%).

$^1$H-NMR (CDCl$_3$, 400 MHz): 1.51 (s, 36H), 3.32 (dd, 2H, J=1.6 Hz), 7.19-7.22 (m, 2H), 7.24 (s, 2H), 7.47 (t, 2H, J=7 Hz), 7.78 (t, 2H, J=1.5 Hz), 8.06-8.11 (m, 4H), 8.19 (d, 2H, J=7 Hz), 8.93 (dd, 4H, J=1, 4.5 Hz), 8.96 (dd, 4H, J=1.4.5 Hz).

$^{13}$C-NMR (CDCl$_3$, 75 MHz): 31.7, 35.0, 113.3, 120.8, 122.5, 122.6, 124.46, 124.54, 124.69, 124.7, 129.2, 129.3, 129.7, 129.8, 129.9, 131.5, 132.6, 138.45, 138.50, 141.6, 144.48, 144.49, 148.55, 148.57, 148.59, 150.6, 150.7.

UV/VIS (CH$_2$Cl$_2$) λ, nm, (ε): 589 (4100), 550 (20886), 423 (498623).

MALDI TOF: 1012.77 (M$^+$), requires 1012.36 for C$_{64}$H$_{60}$N$_4$S$_2$Zn.

[10,20-bis(3,5-di-tert-butylphenyl)-3,5-bis(2,3-benzothienyl)-15-(3-benzothienyl)porphyrinato(2-)-κN$^{21}$,κN$^{22}$, κN$^{23}$,κN$^{24}$)zinc(II) ZnFBTP. The above porphyrin ZnBTP (870 mg, 0.86 mmol) and anhydrous iron(III) chloride (2.5 g, 15.4 mmol, 18 equiv.) were stirred in anhydrous dichloromethane (500 ml) under nitrogen atmosphere at 20° C. (water bath) for 2 hours. The reaction mixture was quenched with pyridine (10 ml), washed with water and passed through pad with silica gel eluting with dichloromethane. Solution of zinc(II) acetate dihydrate (300 mg) in methanol (50 ml) was added to the above solution and the mixture was stirred for 2 hours at room temperature. The reaction mixture was washed with water and the residue after evaporation of dichloromethane was subjected to column chromatography on silica gel, eluting with mixture of hexanes and ethyl acetate 1000-3 to 1000-10 ratio. Yield 490 mg (0.48 mmol, 56%). [10,20-bis(3,5-di-tert-butylphenyl)-3,5-bis(2,3-benzothienyl)-15-(3-benzothienyl)porphyrinato(2-)-κN$^{21}$,κN$^{22}$,κN$^{23}$, κN$^{24}$)zinc(II) ZnFBTP.

$^1$H-NMR (5% pyridine-d5 in CDCl$_3$, 400 MHz): 1.48 and 1.51 (s, 36H), 6.94 (t, 1H, J=7.5 Hz), 7.10 (s, 1H), 7.18 (t, 1H, J=7.5 Hz), 7.23 (td, 1H, J=1, 7.5 Hz), 7.36 (d, 1H, J=7.5 Hz), 7.42 (t, 1H, J=7.5 Hz), 7.66 (t, 1H, J=1.5 Hz), 7.69 (t, 1H, J=1.5 Hz), 7.75 (t, 1H, J=1.5 Hz), 7.77 (t, 1H, J=1.5 Hz), 7.80 (t, 1H, J=1.5 Hz), 7.81 (t, 1H, J=1.5 Hz), 7.92 (s, 1H), 7.95 (d, 1H, J=4.5 Hz), 8.00 (d, 1H, J=4.5 Hz), 8.07 (d, 1H, J=4.5 Hz), 8.08 (d, 1H, J=8 Hz), 8.14 (d, 1H, J=7.5 Hz), 8.23 (d, 1H, J=8 Hz), 8.34 (d, 1H, J=4.5 Hz), 8.85 (d, 1H, J=4.5 Hz).

$^{13}$C-NMR (CDCl$_3$, 75 MHz): 29.7, 31.7, 35.0, 115.7, 118.1, 120.9, 121.1, 121.13, 122.5, 122.9, 123.0, 123.4, 124.0, 124.3, 124.5, 124.53, 125.5, 128.4, 128.7, 128.8, 128.9, 129.1, 129.3, 129.5, 131.0, 131.3, 132.6, 134.1, 135.2, 137.2, 138.8, 139.1, 140.7, 142.8, 143.3, 145.4, 148.0, 148.7, 148.8, 149.0, 149.01, 149.6, 150.5, 151.2, 151.4, 153.8, 154.7, 167.7.

UV/VIS (CH$_2$Cl$_2$) λ, nm, (ε): 795 (1347), 682 (1560), 622 (5572), 570 sh (3800), 535 (14801), 498 (85163), 470 (54970), 405 (83963), 325 (28938). MALDI TOF: 1010.8 (M$^+$), requires 1010.34 for C$_{64}$H$_{58}$N$_4$S$_2$Zn.

Example 4

Cyano-Phenyl Porphyrin Dimer

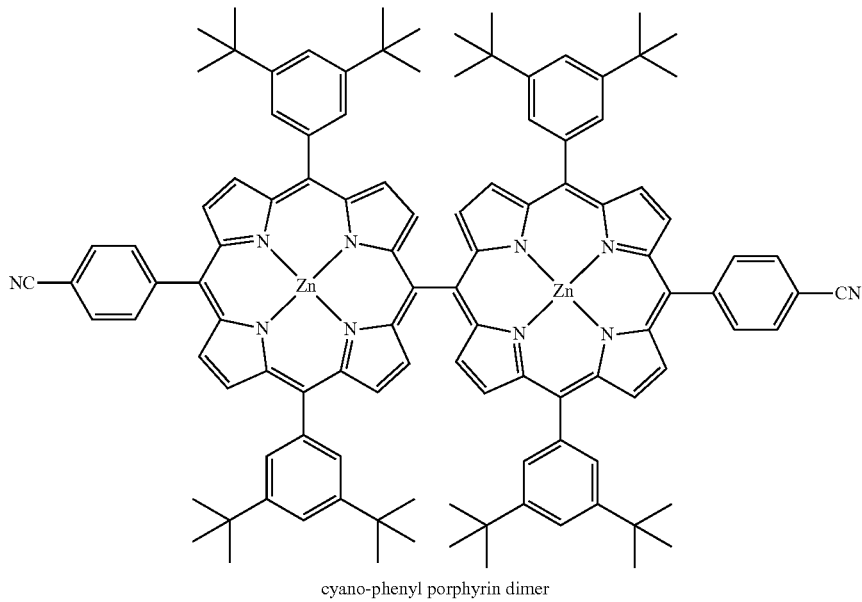

cyano-phenyl porphyrin dimer

[10,20-Bis(3,5-di-tert-butylphenyl)-5(4-cyanophenyl)porphyrinato(2-) $\kappa N^{21},\kappa N^{22},\kappa N^{23},\kappa N^{24}$)zinc(II). (A). NBS (484 mg, 2.72 mmol, 1 equiv.) was added to a stirred solution of bis-(3,5-di-tert-butyl-phenyl)porphyrin (2.034 g, 2.72 mmol) in dichloromethane (280 ml) and pyridine (3.3 ml) at −10° C. (NaCl/ice bath) under nitrogen atmosphere. The reaction mixture was stirred at the same temperature for 10 minutes the was allowed to warm to 0° C. in a water bath for 5 minutes and was quenched with acetone (20 ml). The crude reaction mixture was passed through silica gel column, eluting with dichloromethane-pyridine mixture (100:1). All green-purple tractions were collected, solvents were evaporated, the residue was dissolved in dichloromethane-pyridine mixture (95:5, 100 ml) and 200 ml of methanol was added to precipitate brominated porphyrins. All crystals were collected by filtration after 30 minutes to give a mixture of mono and dibrominated porphyrins (2.39 g). This mixture was used for the next step without further separation.

(B). A mixture of the above mono and dibromoporphyrins (1.68 g, approx. 2.03 mmol), cesium carbonate (4.8 g, 28 mmol), Pd(PPh$_3$)$_4$ (250 mg, 0.22 mmol) and 4-cyanophenyl-tetramethyldioxaborolane 1.0 g, 4.37 mmol, 2.16 equiv.) in toluene (480 ml) was degassed, and refluxed in nitrogen atmosphere for 12 hours. The reaction mixture was cooled and passed consecutively through pad of celite, silica gel and neutral alumina washing with toluene. Toluene was distilled off in vacuum, the residue was separated by column chromatography on silica gel eluting with mixture of hexanes and ethyl acetate to afford [10,20-Bis(3,5-di-tert-butylphenyl)-5-(4-cyanophenyl)porphyrinato(2-)-$\kappa N^{21},\kappa N^{22},\kappa N^{23},\kappa N^{24}$) zinc(II) (0.74 g, 0.87 mmol, 43%).

$^1$H-NMR (CDCl$_3$, 250 MHz): 1.56 (s, 36H), 7.83 (t, 2H, J=1.5 Hz), 8.04 (d, 2H, J=8 Hz), 8.11 (d, 4H, J=1.5 Hz), 8.36 (d, 2H, J=8 Hz), 8.85 (d, 2H, J=4.5 Hz), 9.08 (d, 2H, J=4.5 Hz), 9.15 (d, 2H, J=4.5 Hz), 9.43 (d, 2H, J=4.5 Hz), 9.99 (s, 1H).

{μ-[15,15'-Bis(4-cyanophenyl)-10,10',20,20'-tetrakis(3,5-di-tert-butylphenyl)-5,5'-biporphyrinato(4-)-$\kappa N^{21},\kappa N^{22},\kappa N^{23},\kappa N^{24},\kappa N^{21'},\kappa N^{22'},\kappa N^{23'},\kappa N^{24'}$]}dizinc(II). The above [10,20-Bis(3,5-di-tert-butylphenyl)-5-(4-cyanophenyl)porphyrinato(2-)-$\kappa N^{21},\kappa N^{22},\kappa N^{23},\kappa N^{24}$)zinc(II) (720 mg, 0.85 mmol), DDQ (962 mg, 4.24 mmol, 5 equiv.) and scandium (III) inflate (2.086 mg, 4.24 mmol, 5 equiv.) were dissolved in toluene (500 ml) under nitrogen atmosphere and the mixture was stirred at room temperature for 1 hour and heated at reflux for additional 1 hour. After cooling to room temperature the mixture was passed consecutively through pad with silica gel (2 times) and pad with alumina (elution with dichloromethane-pyridine mixture 100:1). Solvents were evaporated in vacuum, the residue was dissolved in dichloromethane-pyridine mixture (30 ml, 100:1). Fraction 1 contained singly connected porphyrin dimer. Yield 60 mg (0.035 mmol, 8.3%).

$^1$H-NMR (CDCl$_3$, 400 MHz): 1.44 (s, 72H), 7.71 (t, 4H, J=1.5 Hz), 8.08 (d, 8H, J=1.5 Hz), 8.12 (d, 4H, J=8 Hz), 8.44 (d, 4H, J=4.5 Hz), 8.72 (d, 4H, J=4.5 Hz), 8.91 (d, 4H, J=4.5 Hz), 9.06 (d, 4H, J=4.5 Hz).

$^{13}$C-NMR (CDCl$_3$, 75 MHz): 29.7, 31.7, 35.0, 111.6, 118.7, 119.2, 119.9, 120.9, 122.6, 123.7, 129.6, 130.4, 131.1, 132.5, 132.7, 134.0, 134.9, 141.4, 148.2, 148.6, 149.0, 150.3, 151.0, 154.9.

Example 5

Pyrene Porphyrin Trimer

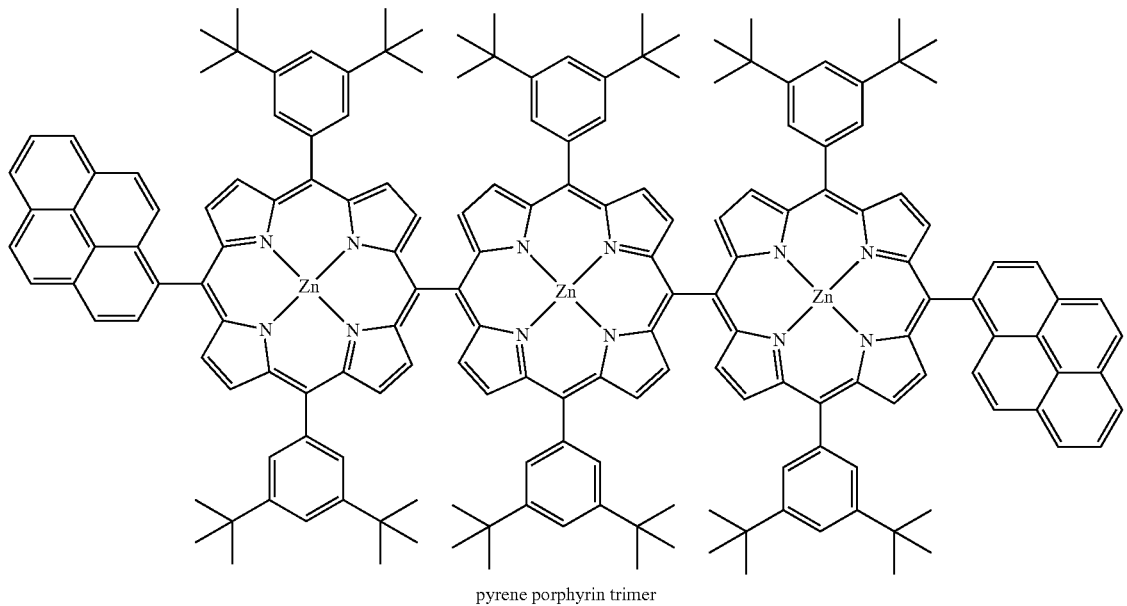

pyrene porphyrin trimer

[10,20-Bis(3,5-di-tert-butylphenyl)-5-(1-pyrenyl)porphyrinato(2-)-κN$^{21}$,κN$^{22}$,κN$^{23}$,κN$^{24}$)zinc(II). (A). NBS (1.54 g, 8.7 mmol, 1.3 equiv.) was added to a stirred solution of bis-(3,5-di-tert-butyl-phenyl) (5 g, 6.7 mmol) in dichloromethane (300 ml) and pyridine (5 ml) at −10° C. (NaCl/ice bath) under nitrogen atmosphere. The reaction mixture was stirred at the same temperature for 10 minutes, then was allowed to warm to 0° C. in a water bath for 5 minutes and was quenched with acetone (20 ml). The crude reaction mixture was passed through silica gel column, eluting with dichloromethane-pyridine mixture (100:1). All green-purple tractions were collected, solvents were evaporated, the residue was dissolved in dichloromethane-pyridine mixture (95:5, 100 ml) and 200 ml of methanol was added to precipitate brominated porphyrins. All crystals were collected by filtration after 30 min to give a mixture of mono and dibrominated porphyrins (ratio 2.3:1, 4.9 g, approx. 85%). This mixture was used for the next step without further separation.

(B). A mixture of the above mono and dibromoporphyrins (ratio of mono- to di-bromoporphyrins 2.3:1, 4 g, approx. 4.7 mmol), cesium carbonate (7.8 g, 24 mmol, 5 equiv.), Pd(PPh3)4 (271 mg, 5 mol %) and 1-pyrenyl-tetramethyl-dioxaborolane (2.32 g, 7.1 mmol) in toluene (700 ml) was degassed and reflux in nitrogen atmosphere for 12 hours. The reaction mixture was cooled and passed consecutively through pad of celite, silica gel and neutral alumina washing with toluene. Toluene was distilled off in vacuum and the residue was separated by fractional crystallization from dichloromethane-methanol and column chromatography on silica gel eluting with mixture of hexanes and ethyl acetate to afford [10,20-Bis(3,5-di-tert-butylphenyl)-5-(1-pyrenyl)porphyrinato(2-)-κN$^{21}$,κN$^{22}$,κN$^{23}$,κN$^{24}$)zinc(II) 2.76 g, 2.9 mmol, 62%) and [10,20-Bis(3,5-di-tert-butylphenyl)-5,15-Bis(1-pyrenyl)porphyrinato(2-)-κN$^{21}$,κN$^{22}$,κN$^{23}$,κN$^{24}$)zinc(II) (0.81 g, 0.71 mmol, 15%).

[10,20-Bis(3,5-di-tert-butylphenyl)-5-(1-pyrenyl)porphyrinato(2-)-κN$^{21}$,κN$^{22}$,κN$^{23}$,κN$^{24}$)zinc(II), $^1$H-NMR (CDCl$_3$, 400 MHz): 1.54 (s, 36H), 7.43 (d, 1H, J=9.3 Hz), 7.67 (d, 1H, J=9.3 Hz), 7.60 (s, 2H), 8.00-8.18 (m, 6H), 8.32 (t, 2H, J=7 Hz), 8.40 (d, 1H, J=9.1 Hz), 8.51 (d, 1H, J=7.7 Hz), 8.63 (d, 2H, J=4.6 Hz), 8.82 (d, 1H, J=7.7 Hz), 8.95 (d, 2H, J=4.6 Hz), 9.18 (d, 2H, J=4.5 Hz), 9.46 (d, 2H, J=4.5 Hz), 10.33 (s, 1H).

MALDI TOF: 950 (M$^+$), requires 948.41 for C$_{64}$H$_{60}$N$_4$Zn.

[10,20-Bis(3,5-di-tert-butylphenyl)-5-(1-pyrenyl)-10-bromoporphyrin. (A). NBS (48 mg, 0.268 mmol, 1 equiv.) was added to a stirred solution of porphyrin VII (255 mg, 0.268 mmol) in dichloromethane (150 ml) and pyridine (2 ml) at −10° C. (NaCl/ice bath) under nitrogen atmosphere. The reaction mixture was stirred at the same temperature for 10 min the was allowed to warm to 0° C. in a water bath for 5 minutes and was quenched with acetone (20 ml). The crude reaction mixture was passed, through silica gel column, eluting with dichloromethane-pyridine mixture (100:1). All green-purple fractions were collected, solvents were evaporated, the residue was dissolved in dichloromethane-pyridine mixture (95:5, 100 ml) and 200 ml of methanol was added to precipitate brominated porphyrin. All crystals were collected by filtration after 30 minutes to give 275 mg (quant) of [10, 20-Bis(3,5-di-tert-butylphenyl)-5-(1-pyrenyl)-10-bromoporphyrinato(2-)-κN$^{21}$,κN$^{22}$,κN$^{23}$,κN$^{24}$)zinc(II): $^1$H-NMR (CDCl$_3$, 400 MHz): 1.48 and 1.49 (2, 36H), 7.54 (d, 1H, J=14 Hz), 7.74 (t, 2H, J=1.5 Hz), 7.98-8.03 (m, 6H), 8.23-8.28 (m, 2H), 8.34 (d, 1H, J=9 Hz), 8.42 (d, 2H, J=4.5 Hz), 8.45 (s, 1H), 8.75 (d, 2H, J=4.5 Hz), 8.76 (2, 1H, j 8 Hz), 8.96 (d, 2H, J=4.5 Hz), 9.72 (d, 2H, J=4.5 Hz).

(B). To a stirring solution of the above bromo-pyrene substituted porphyrin in 100 ml of dichloromethane concentrated aq. Hydrochloric acid (2 ml) was added and the reaction mixture was vigorously stirred for 3 minutes. After that reaction mixture was quenched with pyridine (5 ml) and the resulting solution was passed, through a filter with silica gel eluting with dichloromethane. The residue after evaporation of solvents in vacuum is pure free-base porphyrin.

$^1$H-NMR (CDCl$_3$, 400 MHz): 1.55 and 1.56 (2, 36H), 7.40 (d, 1H, J=9 Hz), 7.63 (d, 1H, J=9 Hz), 7.75 (t, 2H, J=1.5 Hz), 7.97-8.03 (m, 6H), 8.22-8.26 (m, 1H), 8.31 (d, 1H, J=9 Hz), 8.40 (d, 2H, J=4.5 Hz), 8.42 (d, 1H, J=8 Hz), 8.69-8.71 (m, 3H), 8.92 (d, 2H, J=4.5 Hz), 9.66 (d, 2H, J=4.5 Hz).

[10,20-Bis(3,5-di-tert-butylphenyl)-5,15-bis(4,4,5,5-tetramethyl-[1,3,2]-dioxaborolanyl)porphyrinato(2-)-κN$^{21}$, κN$^{22}$,κN$^{23}$,κN$^{24}$)zinc(II). (A). NBS (2.61 g, 14.7 mmol, 2.2 equiv.) was added to a stirred solution of porphyrin I (5 g, 6.7 mmol) in dichloromethane (500 ml) and pyridine (5 ml) at −10° C. (NaCl/ice bath) under nitrogen atmosphere. The reaction mixture was stirred at the same temperature for 10 minutes, then was allowed to warm to 0° C. in a water bath for 5 minutes and was quenched with acetone (20 ml). The crude reaction mixture was passed, through silica gel column, eluting with dichloromethane-pyridine mixture (100:1). All green-purple fractions were collected, solvents were evaporated, the residue was dissolved in dichloromethane-pyridine mixture (95:5, 100 ml) and 200 ml of methanol was added to precipitate dibromoporphyrin. All crystals were collected by filtration after 30 minutes to give [10,20-Bis(3,5-di-tert-butylphenyl)-5,15-bis-bromo-porphyrinato(2-)-κN$^{21}$,κN$^{22}$, κN$^{23}$,κN$^{24}$)zinc(II) (4.76 g, 5.23 mmol, 78%).

$^1$H-NMR (5%-pyridine-d$_5$ in CDCl$_3$, 400 MHz): 1.46 (s, 36H), 7.30 (t, 2H, J=1.5 Hz), 7.91 (d, 4H, J=1.5 Hz), 8.83 (d, 4H, J=4.5 Hz), 9.58 (d, 4H, J=4.5 Hz).

(B). A mixture of dibromoporphyrin (1.05 g, 1.15 mmol), pinacoleborane (5 ml) Cl$_2$—Pd(PPh$_3$)$_2$ (170 mg, 0.26 mmol) triethylamine (3 ml) and pyridine (3 ml) in toluene (200 ml) was degassed and reflux in nitrogen atmosphere for 1 hour. The reaction mixture was cooled and quenched carefully with water (10 ml drop wise). Toluene was distilled off in vacuum, the residue was separated by column chromatography on silica gel eluting with mixture of hexanes and ethyl acetate to afford [10,20-Bis(3,5-di-tert-butylphenyl)-5,15-bis(4,4,5,5-tetramethyl-[1,3,2]dioxaborolanyl)porphyrinato(2-)-κN$^{21}$, κN$^{22}$,κN$^{23}$,κN$^{24}$)zinc(II) (Fraction 3, 0.3 g).

$^1$H-NMR (CDCl$_3$, 400 MHz): 1.63 (s, 36H), 1.90 (s, 24H), 7.89 (t, 2H, J=1.5 Hz), 8.17 (d, 4H, J=1.51 Hz), 9.20 (d, 4H, J=4.5 Hz), 9.99 (d, 4H, J=4.5 Hz).

{μ$_3$-[10,10″-Bis(1-pyrenyl)-5,5′5″,15,15′15′-hexakis(3,5-di-tert-butylphenyl)-tetracyclo-2,2′:8′2″-terporphyrinato(6-)-κN$^{21}$,κN$^{22}$,κN$^{23}$,κN$^{24}$:κN$^{23'}$,κN$^{22'}$,κN$^{23'}$,κN$^{24'}$:□N$^{21''}$, κN$^{21''}$,κN$^{22''}$,κN$^{23''}$,κN$^{24''}$]}trizinc(II) pyrene porphyrin trimer. (A). A mixture of porphyrin VI (118 mg, 0.118 mmol), porphyrin VIII (250 mg, 2.2 equiv.), Pd(PPh$_3$)$_4$ (27 mg, 0.26 mmol) and cesium carbonate (197 mg, 0.588 mmol) in toluene (20 ml) and DMF (10 ml) was degassed and heated to 90° C. in nitrogen atmosphere for 20 hours. The reaction mixture was cooled and washed with water (3×100 ml). Toluene was distilled off in vacuum and the residue was subjected to GPC column first (BioRad polystyrene-divinylbenzene copolymer beads, toluene). The first fraction was collected and subjected to column with silica gel eluting with hexanes-ethyl acetate mixtures. The first fraction was collected and the residue after evaporation of solvents was crystallized from dichloromethane-methanol mixture to give 30 mg (0.012 mmol, 10%) of {μ$_3$-[10,10″-Bis(1-pyrenyl)-5,5′,5″,15,15′15″-hexakis(3,5-di-tert-butylphenyl)-tetracyclo-2,2′:8′2″-terporphyrinato(6-)-κN$^{21'}$,κN$^{22'}$,κN$^{23'}$,κN$^{24'}$]}zinc(II).

$^1$H-NMR (CDCl$_3$, 400 MHz): −1.87 (s, 4H), 1.26 (s 36H), 1.38 (t, 18H, J=3 Hz), 1.44 (d, 36H, J=3 Hz), 1.54 (s, 36H), 7.61 (d, 2H, J=9 Hz), 7.63 (t, 2H, J=1.5 Hz), 7.70 (t, 4H, J=1.5 Hz), 7.79 (d, 2H, J=9 Hz), 8.10-8.15 (m, 14H), 8.20 (d, 4H, J=4.5 Hz), 8.30 (t, 4H, J=4.5 Hz), 8.35-8.38 (m, 4H), 8.45 (d, 2H, J=9 Hz), 8.58-8.60 (m, 6H), 8.70 (d, 4H, J=4.5 Hz), 8.79 (t, 4H, J=4.5 Hz), 8.84 (d, 4H, J=4.5 Hz), 8.92 (d, 4H, J=4.5 Hz).

$^{13}$C-NMR (CDCl$_3$, 75 MHz): 29.7, 31.7, 35.0, 105.0, 118.2, 118.9, 119.5, 120.9, 121.0, 122.5, 122.8, 124.2, 124.7, 125.3, 125.6, 126.3, 127.4, 127.7, 127.8, 128.0, 129.3, 129.6, 129.8, 130.9, 131.5, 131.8, 132.4, 132.6, 133.5, 134.0, 137.3, 140.9, 141.5, 148.4, 148.7, 150.6, 153.8, 154.8.

UV/VIS (CH$_2$Cl$_2$) λ, nm, (ε): 243 (118450), 264 (60690), 275 (76840), 323 (58970), 338 (66590), 417 (264100), 475 (234730), 523 (74990), 562 (68250), 597 (29200), 705 (2000).

(B). To a solution of the above porphyrin trimer (20 mg) in dichloromethane (100 ml) solution of zinc(II) acetate (100 mg) in methanol (5 ml) was added and reaction mixture was kept at room temperature for 12 hours. After that solvents were removed in vacuum, the residue was passed through filter with silica gel eluting with dichloromethane. The final product was crystallized from dichloromethane-methanol mixture to afford {μ$_3$-[10,10″-Bis(1-pyrenyl)-5,5′5″,15,15′15″-hexakis(3,5-di-tert-butylphenyl)-tetracyclo-2,2′:8′2″-terporphyrinato(6-)-κN$^{21}$,κN$^{22}$,κN$^{23}$,κN$^{24}$:κN$^{21'}$,κN$^{22'}$, κN$^{23'}$,κN$^{24'}$:κN$^{21''}$,κN$^{22''}$,κN$^{23''}$,κN$^{24''}$]}trizinc(II) pyrene porphyrin trimer.

$^1$H-NMR (CDCl$_3$, 400 MHz): 1.26 (s, 36H), 1.38 (t, 36H, J=3 Hz), 1.44 and 1.45 (s, 36H), 7.58 (d, 2H, J=9 Hz), 7.62 (1, 2H, J=1.5 Hz, 7.70 (t, 4H, J=1.5 Hz), 7.78 (d, 2H, J=9 Hz), 8.09-8.16 (m, 14H), 8.25 (d, 2H, J=4.5 Hz), 8.29 (d, 2H, J=4.5 Hz), 8.31 (d, 4H, J=4.5 Hz), 8.35-8.38 (m, 4H), 8.46 (d, 2H, J=9 Hz), 8.59 (d, 2H, J=9 Hz), 8.69 (d, 4H, J=4.5 Hz), 8.78-8.81 (m, 4H), 8.81 (d, 4H, J=4.5 Hz), 8.94 (d, 2H, J=9 Hz), 8.96 (d, 4H, J=4.5 Hz).

$^{13}$C-NMR (CDCl$_3$, 75 MHz): 28.7, 30.6, 33.9, 118.2, 118.8, 119.2, 119.8, 121.7, 122.4, 123.0, 123.2, 123.7, 124.2, 124.4, 125.2, 126.5, 126.7, 126.9, 128.4, 128.5, 128.6, 129.8, 130.4, 130.8, 131.0, 131.1, 131.3, 131.5, 132.5, 132.9, 136.9, 140.5, 147.4, 147.5, 149.3, 149.5, 149.89, 149.93, 153.8, 153.9.

Examples of photovoltaic (PV) devices: PV cells were grown on ITO-coated glass substrates that were solvent cleaned and treated in UV-ozone for 10 minutes immediately prior to loading into high vacuum chamber (base pressure 1-3×10$^{-6}$ Torr). The following organic materials were purchased from commercial sources: C$_{60}$ (MTR Limited), 2,9-dimethyl-4,7-diphenyl-1,10-phenanthroline (BCP) (Aldrich) and were purified by sublimation prior to use. Metal cathode material (Al) were used as received (Alfa Aesar). Materials were sequentially grown by vacuum thermal evaporation at the following rates: C$_{60}$ (2 A/sec), BCP (2 A/sec), Al (3-5 A/sec). The cathode was evaporated through a shadow mask with 1 mm diameter openings. For solution processed donor, the layers were spin coated for 40 sec. at 2000 rpm for a final thickness of 100 Å. Current-voltage (1-V) characteristics of the PV cells were measured under simulated AM1.5G solar illumination (Oriel Instruments) using a Keithley 2420 3A Source Meter. Donor layer thicknesses and amount of additives were experimentally modified for highest power conversion efficiency.

The foregoing description and examples have been set forth merely to illustrate the invention and are not intended to be limiting. Each of the disclosed, aspects and embodiments of the present disclosure may be considered individually or in combination with other aspects, embodiments, and variations of the invention. In addition, unless otherwise specified, none of the steps of the methods of the present disclosure are confined to any particular order of performance. Modifications of the disclosed embodiments incorporating the spirit and substance of the invention may occur to persons skilled in the art and such modifications are within the scope of the present invention.
We claim:
1. A compound comprising a non-activated porphyrin fused with one or more non-activated polycyclic aromatic rings, said compound having a formula selected from the group consisting of:
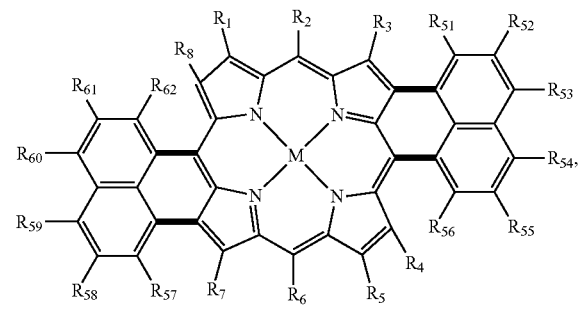
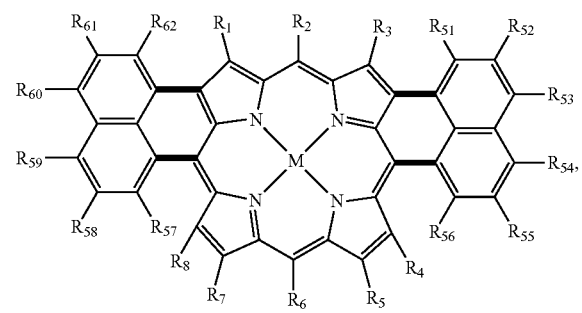
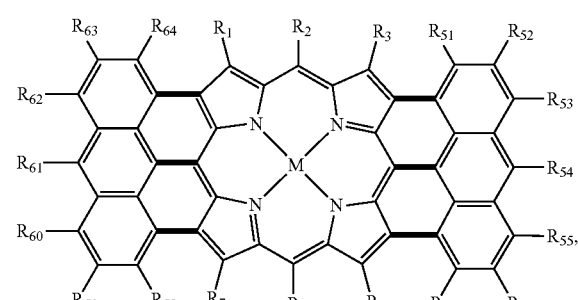
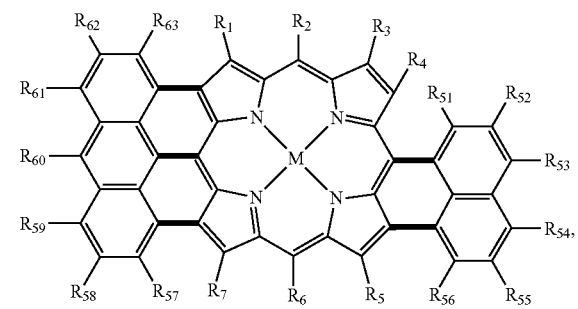
-continued
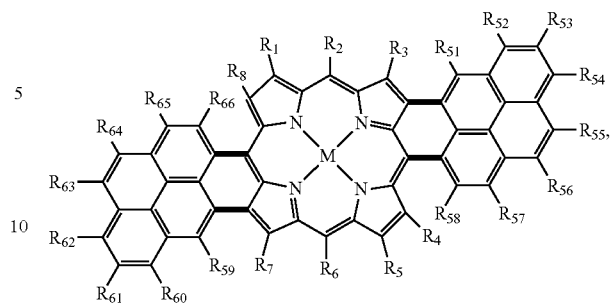
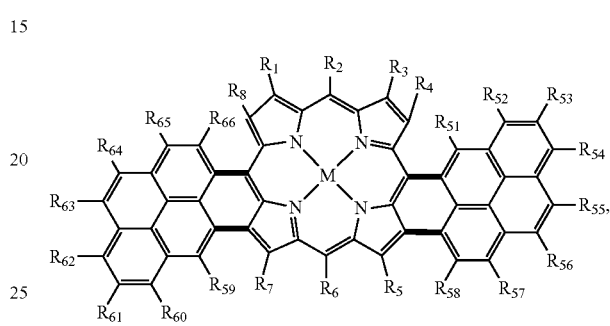
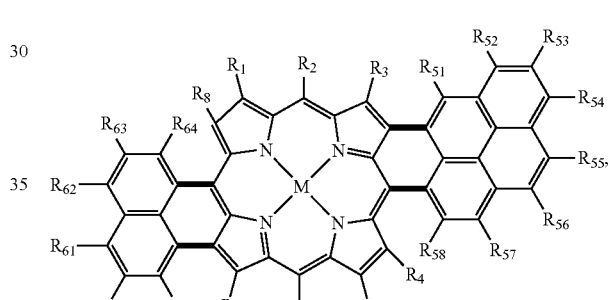
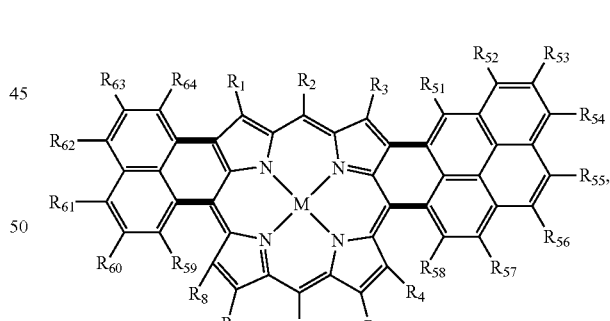
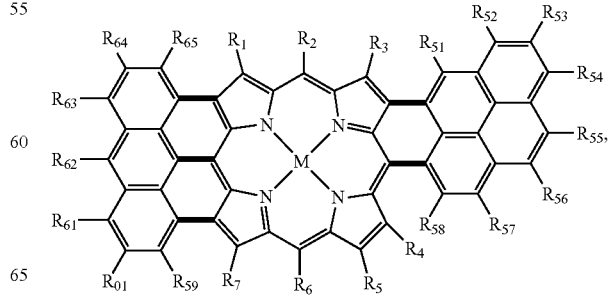

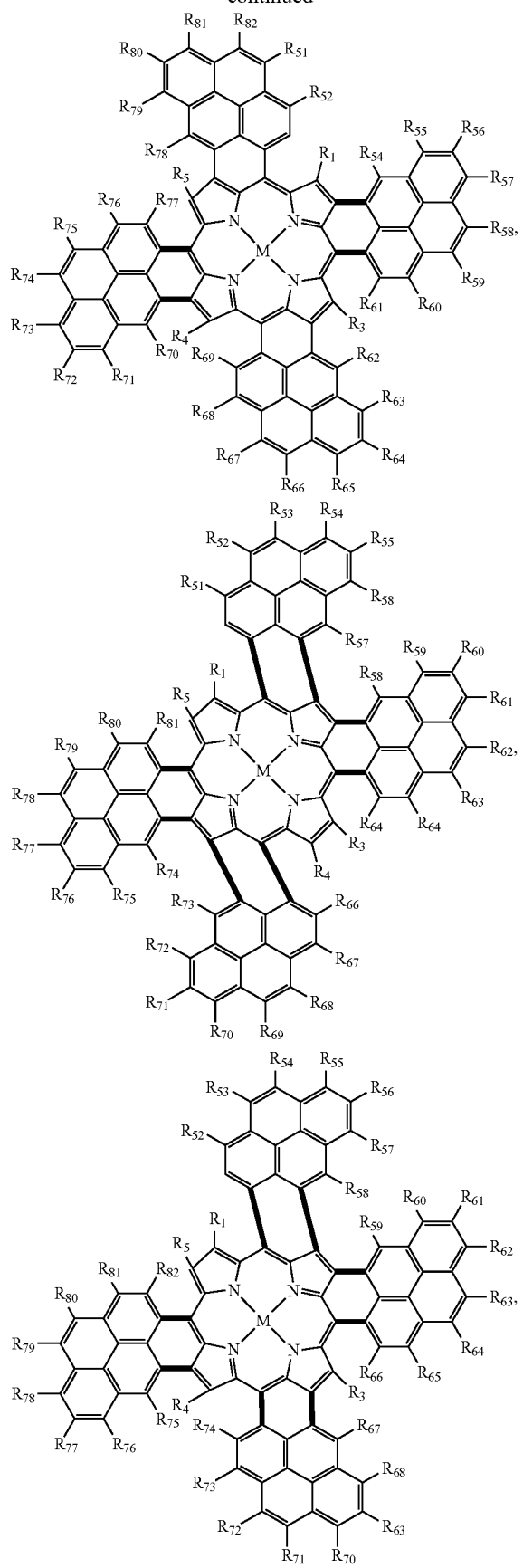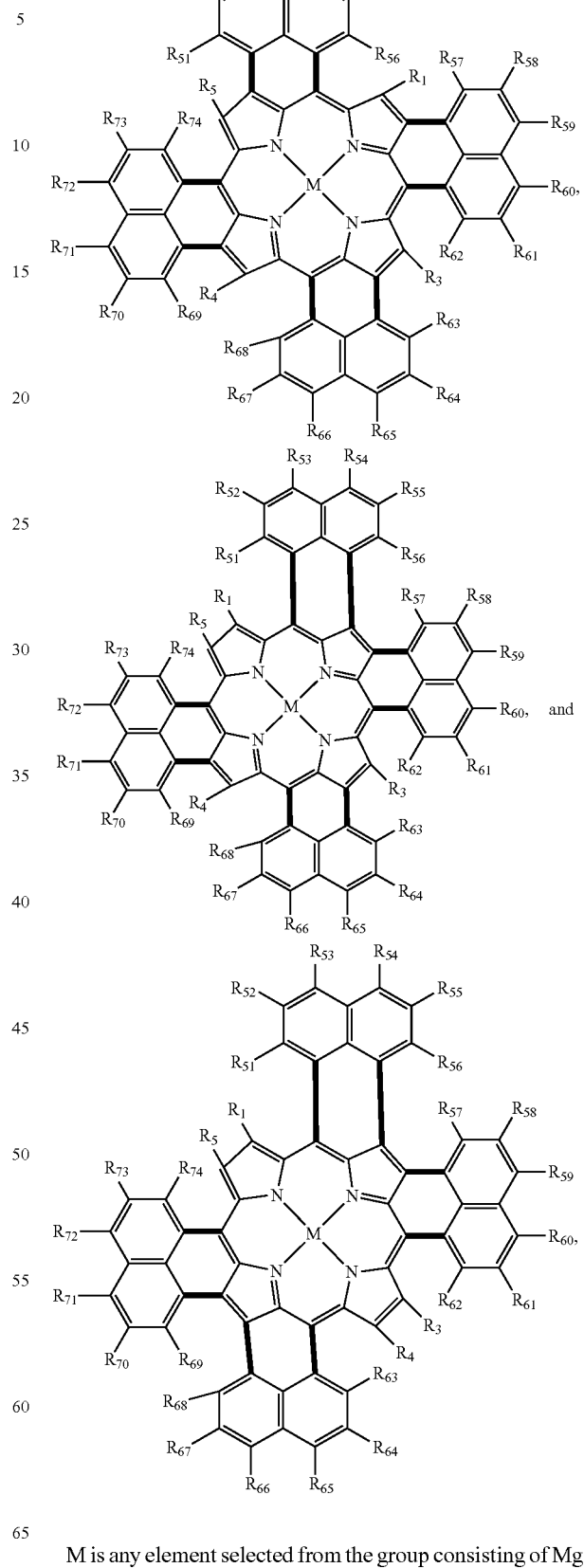
M is any element selected from the group consisting of Mg, Ca, Sr, Ba, Sc, Y, La, Ce, Ti, Nb, Ta, Cr, Mo, W, Mn, Tc, Re, Fe, Ru, Os, Co, Rh, Ir, Ni, Pd, Pt, Cu, Ag, Au, Zn, Cd, Hg, Al, Ga, In, Ti, Si, Ge, Sn, Pb, P, As, Sb, Bi, Pr, Nd, Sm, Eu, Gd, Tb, Dy, Ho, Er, Tm, Yb, Lu, Th, and U;

wherein $R_1$, $R_3$-$R_5$, $R_7$-$R_8$ and $R_{51}$-$R_{82}$ are independently selected from the group consisting of hydrogen, alkyl, fluoroalkyl, hydroxyl, halo, mercapto group, amino, cyano, alkenyl, alkynyl, and aryl, wherein $R_2$ and $R_6$ are independently selected from the group consisting of hydrogen, alkyl, fluoroalkyl, hydroxyl, alkoxy, halo, mercapto group, amino, cyano, alkenyl, alkynyl, 3,5-di-tert-butylphenyl, and aryl, and wherein adjacent substituents $R_{51}$-$R_{82}$ optionally form fused rings, wherein the fused rings are aromatic, unsaturated, or combinations of both aromatic and unsaturated rings, including four, five, six, seven, eight, or nine-membered rings, wherein the fused rings can include one or more heteroatoms independently selected from the group consisting of O, S, Se, Te, N, P, As, Si, Ge, and B.

2. The compound of claim 1, having a formula selected from the group consisting of:

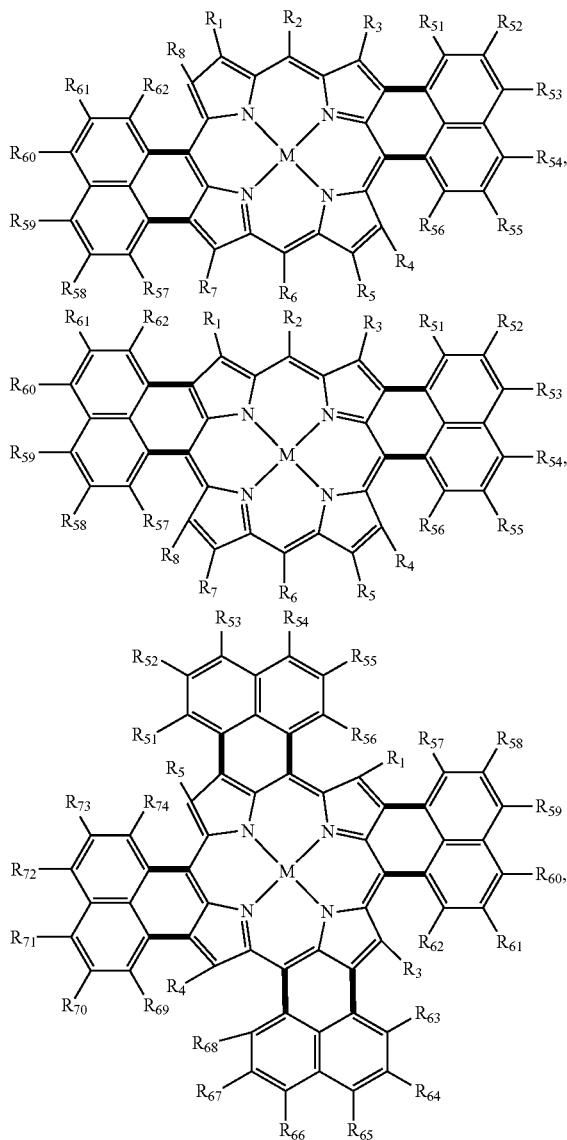

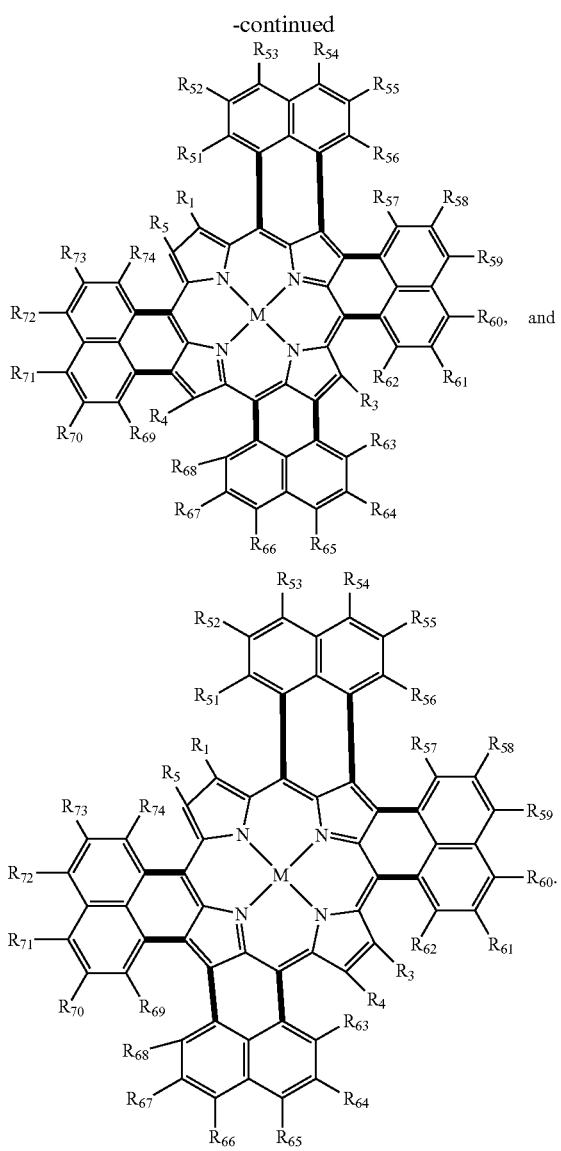

3. The compound of claim 1, wherein $R_1$, $R_3$-$R_5$, $R_7$-$R_8$, and $R_{51}$-$R_{82}$ are independently selected from the group consisting of hydrogen, $C_1$-$C_{15}$ alkyl, fluoroalkyl, hydroxyl, halo, mercapto group, amino, cyano, $C_2$-$C_{15}$ alkenyl, $C_2$-$C_{15}$ alkynyl, and aryl, wherein $R_2$ and $R_6$ are independently selected from the group consisting of hydrogen, $C_1$-$C_{15}$ alkyl, fluoroalkyl, hydroxyl, alkoxy, halo, mercapto group, amino, cyano, $C_2$-$C_{15}$ alkenyl, $C_2$-$C_{15}$ alkynyl, 3,5-di-tert-butylphenyl, and aryl.

4. The compound of claim 1, wherein $R_1$, $R_3$-$R_5$, $R_7$-$R_8$, and $R_{51}$-$R_{82}$ are independently selected from the group consisting of hydrogen, $C_1$-$C_{15}$ alkyl, $C_2$-$C_{15}$ alkenyl, $C_2$-$C_{15}$ alkynyl, and aryl, wherein $R_2$ and $R_6$ are independently selected from the group consisting of hydrogen, $C_1$-$C_{15}$ alkyl, $C_2$-$C_{15}$ alkenyl, $C_2$-$C_{15}$ alkynyl, 3,5-di-tert-butylphenyl, and aryl.

5. The compound of claim 1, wherein the one or more non-activated polycyclic aromatic rings are selected from the group consisting of:

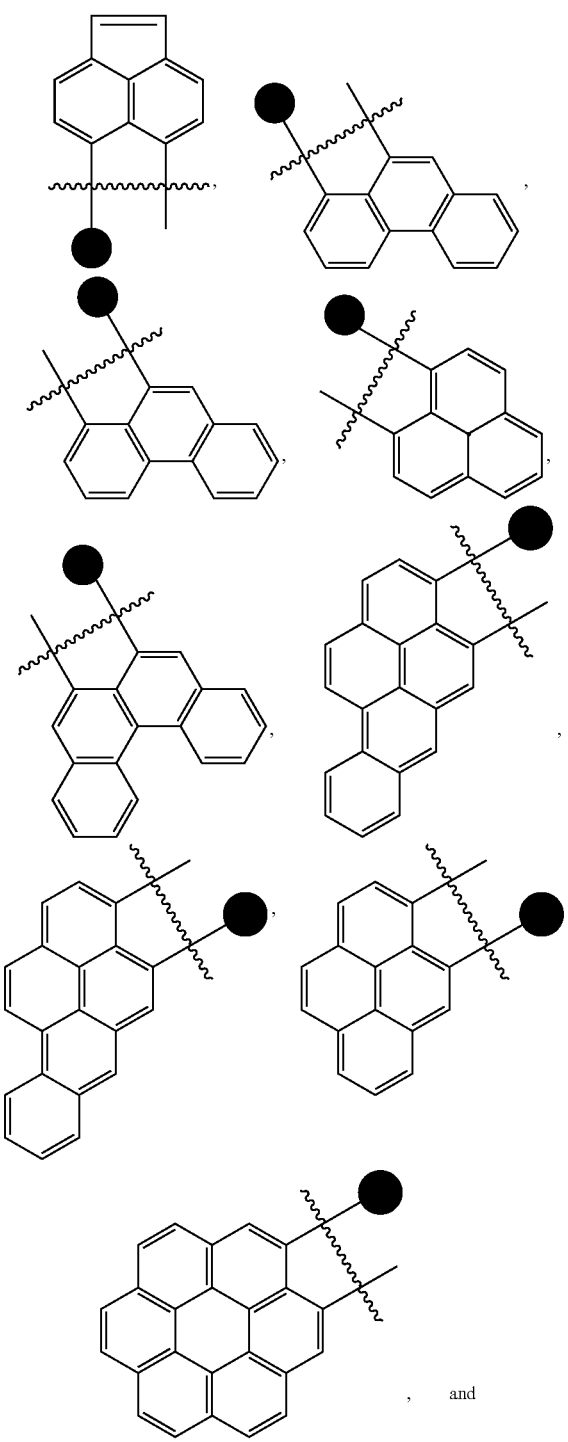

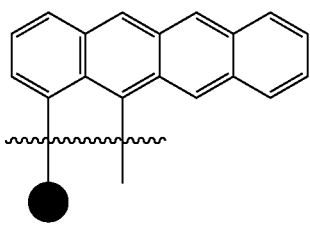
-continued wherein the wave-line represents the fusion position of the polycyclic aromatic rings to the porphyrin; and wherein the dot represents the point where the polycyclic aromatic rings are connected to the mesa position of the porphyrin.

6. The compound of claim 1, wherein, when present, each one of $R_{51}$-$R_{82}$ is hydrogen.

7. The compound of claim 1, wherein the compound is

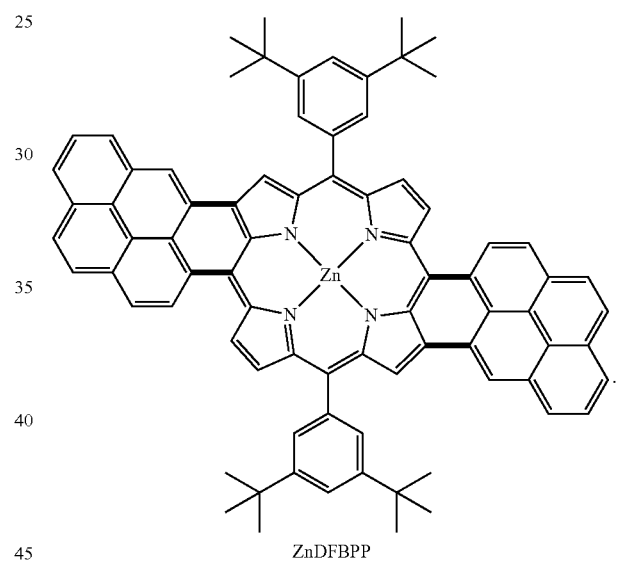

ZnDFBPP

8. The compound of claim 1, wherein the porphyrin and at least one of the polycyclic aromatic rings are fused in meso,β mode.

9. The compound of claim 1, wherein the porphyrin and at least one of the polycyclic aromatic rings are fused in β,meso,β mode.

* * * * *

UNITED STATES PATENT AND TRADEMARK OFFICE
CERTIFICATE OF CORRECTION

PATENT NO. : 9,113,535 B2  
APPLICATION NO. : 12/985439  
DATED : August 18, 2015  
INVENTOR(S) : Mark E. Thompson et al.

It is certified that error appears in the above-identified patent and that said Letters Patent is hereby corrected as shown below:

IN THE SPECIFICATION

Column 10, Line 14, delete "effusing" and insert -- of fusing --.

Column 13, Line 50, delete "d/s-pyrenyl" and insert -- bis-pyrenyl --.

Column 16, Line 7, delete "effused" and insert -- of fused --.

Column 16, Line 34, delete "fission" and insert -- fusion --.

Column 33, Line 42, delete "tractions" and insert -- fractions --.

Signed and Sealed this  
Fifth Day of January, 2016

Michelle K. Lee  
*Director of the United States Patent and Trademark Office*